United States Patent
Kwon et al.

(10) Patent No.: US 11,623,934 B2
(45) Date of Patent: Apr. 11, 2023

(54) INFRARED ABSORBERS, INFRARED ABSORBING/BLOCKING FILMS AND PHOTOELECTRIC DEVICES, SENSORS, AND ELECTRONIC DEVICES

(71) Applicant: Samsung Electronics Co., Ltd., Suwon-si (KR)

(72) Inventors: Ohkyu Kwon, Seoul (KR); Hwang Suk Kim, Suwon-si (KR); Dong-Seok Leem, Seongnam-si (KR); Rae Sung Kim, Hwaseong-si (KR); Hyesung Choi, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 32 days.

(21) Appl. No.: 17/334,106

(22) Filed: May 28, 2021

(65) Prior Publication Data

US 2021/0380607 A1 Dec. 9, 2021

(30) Foreign Application Priority Data

May 29, 2020 (KR) .................. 10-2020-0065157

(51) Int. Cl.
*C07D 519/00* (2006.01)
*H01L 51/44* (2006.01)
(Continued)

(52) U.S. Cl.
CPC ........... *C07D 519/00* (2013.01); *G02B 5/208* (2013.01); *G02B 5/223* (2013.01); *H10K 30/87* (2023.02)

(58) Field of Classification Search
CPC ...... C07D 519/00; G02B 5/208; G02B 5/223; H01L 51/42–50
See application file for complete search history.

(56) References Cited

U.S. PATENT DOCUMENTS 10,738,240 B2   8/2020  Kirsch et al.
2014/0303379 A1* 10/2014 Santarelli .............. C09B 57/00
                                                 548/121
(Continued)

FOREIGN PATENT DOCUMENTS

KR   2018-0002824 A    1/2018
WO   WO-2016177449 A1  11/2016

OTHER PUBLICATIONS

Gang Qian et al. "Synthesis and Application of Thiadiazoloquinoxaline-Containing Chromophores as Dopants for Efficient Near-Infrared Organic Light-Emitting Diodes" *J. Phys. Chem. C* 2009, 113, 1589-1595.
(Continued)

*Primary Examiner* — Golam Mowla
(74) *Attorney, Agent, or Firm* — Harness, Dickey & Pierce, P.L.C.

(57) ABSTRACT

An infrared absorber includes a compound represented by Chemical Formula

[Chemical Formula 1]

(Continued)

In Chemical Formula 1, $Ar^1$, $Ar^2$, $X^1$, $L^1$, $L^2$, $R^1$, $R^2$, $R^3$, and $R^4$ are the same as defined in the detailed description.

30 Claims, 13 Drawing Sheets

(51) Int. Cl.
  *G02B 5/22* (2006.01)
  *G02B 5/20* (2006.01)

(56) References Cited

U.S. PATENT DOCUMENTS

2018/0142153 A1* 5/2018 Kirsch ................. C09K 19/52
2019/0067608 A1   2/2019 Wang et al.

OTHER PUBLICATIONS

Karen Strassel et al. "Squaraine Dye for a Visibly Transparent All-Organic Optical Upconversion Device with Sensitivity at 1000 nm" ACS Appl. Mater. Interfaces 2018, 10, 11063?11069.

Ji Qi et al. "Highly Stable Organic Small Molecular Nanoparticles as an Advanced and Biocompatible Phototheranostic Agent of Tumor in Living Mice" ACS Nano 2017, 11, 7177?7188.

M. L. Keshtov et al. "New low bandgap near-IR conjugated D-A copolymers for BHJ polymer solar cell applications" *Phys. Chem. Chem. Phys.*, 2016, 18, 8389—8400.

Gang Qian et al. "Simple and Efficient Near-Infrared Organic Chromophores for Light-Emitting Diodes with Single Electroluminescent Emission above 1000nm" Adv. Mater. 2009, 21, 111-116.

Cunbin An et al. "Thiadizoloquinoxaline-Based Low-Bandgap Conjugated Polymers as Ambipolar Semiconductors for Organic Field Effect Transistors" Chem. Mater. 2014, 26, 5923?5929.

* cited by examiner

… (1) …

INFRARED ABSORBERS, INFRARED ABSORBING/BLOCKING FILMS AND PHOTOELECTRIC DEVICES, SENSORS, AND ELECTRONIC DEVICES

CROSS-REFERENCE TO RELATED APPLICATION

This application claims priority to and the benefit under 35 U.S.C. § 119 of Korean Patent Application No. 10-2020-0065157 filed in the Korean Intellectual Property Office on May 29, 2020, the entire contents of which are incorporated herein by reference.

BACKGROUND

(a) Field

Infrared (NIR) absorbers, Infrared absorbing/blocking films, photoelectric devices, sensors, and electronic devices are disclosed.

(b) Description of the Related Art

An imaging device is used in a digital camera and a camcorder, etc., to capture an image and to store it as an electrical signal, and the imaging device includes a sensor separating incident light according to a wavelength and converting each component to an electrical signal.

SUMMARY

Some example embodiments provide an infrared absorber having improved infrared light absorption characteristics.

Some example embodiments provide a film including the infrared absorber.

Some example embodiments provide a photoelectric device including the infrared absorber. Such photoelectric device may provide improved sensitivity of a sensor in a low-illumination environment and/or may be used as a biometric device.

Some example embodiments provide a sensor including the infrared absorber or the photoelectric device.

Some example embodiments provide an electronic device including the photoelectric device or the sensor.

According to some example embodiments, an infrared absorber including a compound represented by Chemical Formula 1 is provided.

[Chemical Formula 1]

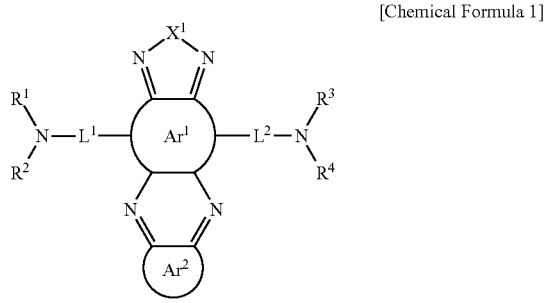

In Chemical Formula 1, $Ar^1$ may be a substituted or unsubstituted C6 to C30 aromatic ring, a substituted or unsubstituted C3 to C30 heteroaromatic ring, or a combination thereof, $Ar^2$ may be a substituted or unsubstituted C6 to C30 aromatic ring, a substituted or unsubstituted C3 to C30 heteroaromatic ring, or a combination thereof, $X^1$ may be O, S, Se, Te, S(=O), S(=O)$_2$, NR$^a$, CR$^b$R$^c$, or SiR$^d$R$^e$, wherein R$^a$, R$^b$, R$^c$, R$^d$, and R$^e$ may each independently be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, $R^1$, $R^2$, $R^3$, and $R^4$ may each independently be hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, $R^1$ and $R^2$ each independently exist or are linked to each other to form a first ring, and $R^3$ and $R^4$ each independently exist or are linked to each other to form a second ring, and $L^1$ may be represented by Chemical Formula 1A or Chemical Formula 1B, and $L^2$ may be represented by Chemical Formula 1C or Chemical Formula 1D.

[Chemical Formula 1A]

[Chemical Formula 1B]

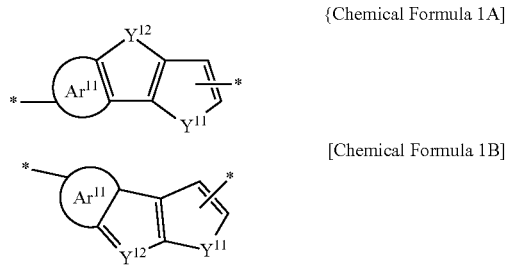

wherein, in Chemical Formula 1A and Chemical Formula 1B, $Y^{11}$ and $Y^{12}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Ar^{11}$ may be a substituted or unsubstituted C6 to C30 aromatic ring, a substituted or unsubstituted C3 to C30 heteroaromatic ring, or a combination thereof, and

* on a left side of Chemical Formula 1A and Chemical Formula 1B is a portion that is bound to N of —N(R$^1$)(R$^2$) of Chemical Formula 1, and * on a right side of Chemical Formula 1A and Chemical Formula 1B is a portion that is bound to $Ar^1$ of Chemical Formula 1,

[Chemical Formula 1C]

[Chemical Formula 1D]

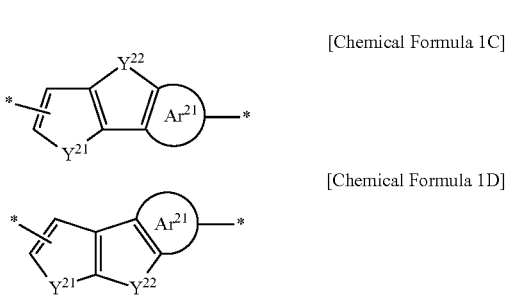

wherein, in Chemical Formula 1C and Chemical Formula 1D, $Y^{21}$ and $Y^{22}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, Ar$^{21}$ may be a substituted or unsubstituted C6 to C30 aromatic ring, a substituted or unsubstituted C3 to C30 heteroaromatic ring, or a combination thereof, and

* on a left side of Chemical Formula 1C and Chemical Formula 1D is a portion that is bound to Ar$^1$ of Chemical Formula 1, and * on a right side of Chemical Formula 1C and Chemical Formula 1D is a portion that is bound to N of —N(R$^3$)(R$^4$) of Chemical Formula 1.

In Chemical Formula 1, Ar$^1$ may be benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, Ar$^1$ may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

In Chemical Formula 1, Ar$^1$ may be one moiety of a set of moieties represented by represented by Chemical Formula A-1, each moiety including at least one aromatic ring and left and right linking groups.

In Chemical Formula A-1, hydrogen of each aromatic ring may be replaced by deuterium, a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—X$^1$—N-containing pentagonal ring of Chemical Formula 1 and an N-containing hexagonal ring of Chemical Formula 1, and

*'s of the left and right linking groups are linking portions linked to separate, respective ones of L$^1$ and L$^2$ of Chemical Formula 1.

In Chemical Formula 1, Ar$^1$ may be one moiety of a set of moieties represented by Chemical Formula A-2, each moiety including at least one aromatic ring and left and right linking groups.

[Chemical Formula A-2]

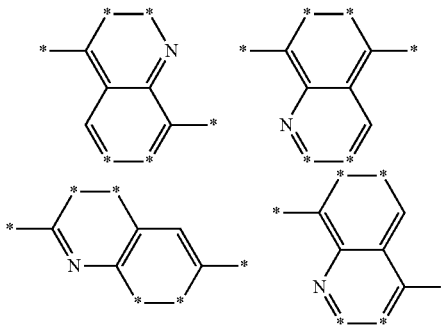

[Chemical Formula A-1]

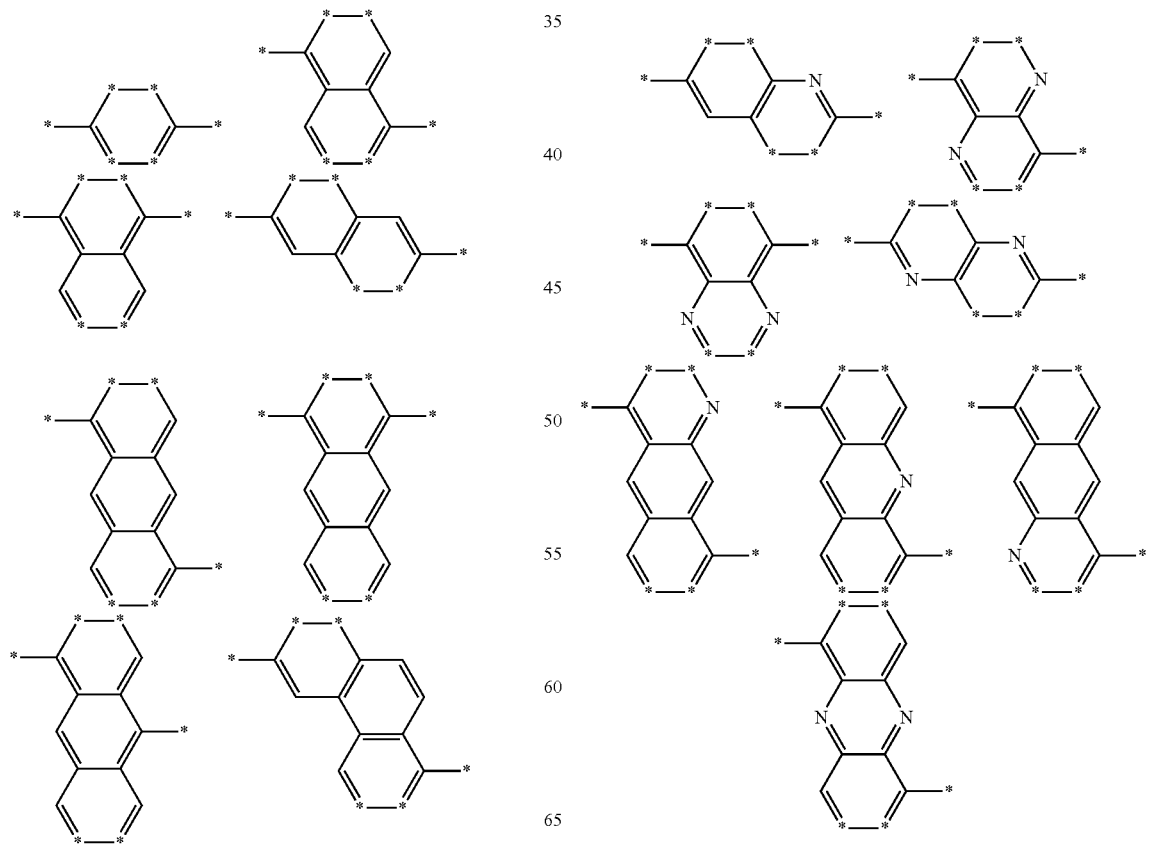

In Chemical Formula A-2, hydrogen of each aromatic ring may be replaced by deuterium, a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and

*'s of the left and right linking groups are linking portions linked to separate, respective ones of $L^1$ and $L^2$ of Chemical Formula 1.

In Chemical Formula 1, $Ar^2$ may be a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, $Ar^2$ may be a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

In Chemical Formula 1, $Ar^2$ may be one moiety of a set of moieties represented by Chemical Formula B-1, each moiety including at least one aromatic ring.

[Chemical Formula B-1]

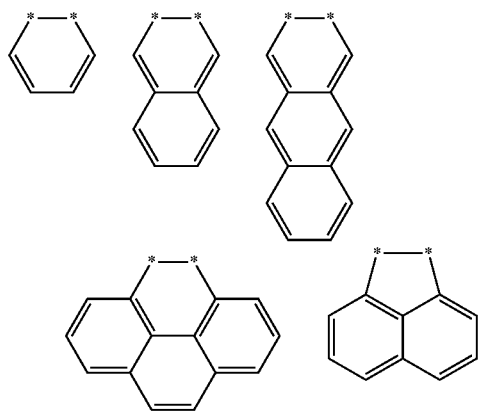

In Chemical Formula B-1, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and adjacent pairs of *'s inside the at least one aromatic ring are linking portions with an N-containing hexagonal ring of Chemical Formula 1.

In Chemical Formula 1, $Ar^2$ may be one moiety of a set of moieties represented by Chemical Formula B-2, each moiety including at least one aromatic ring.

[Chemical Formula B-2]

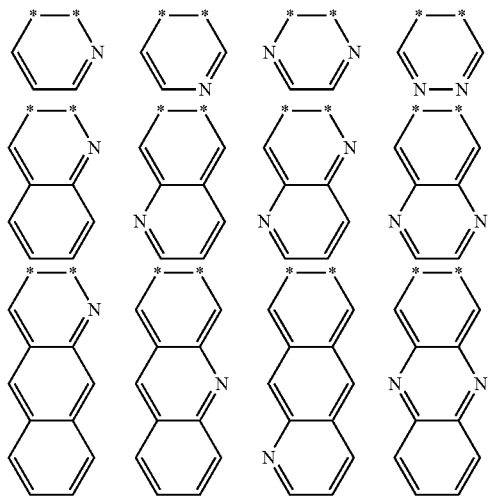

In Chemical Formula B-2, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and adjacent pairs of *'s inside the at least one aromatic ring are linking portions with an N-containing hexagonal ring of Chemical Formula 1.

In Chemical Formula 1, $Ar^2$ may be one moiety of a set of moieties represented by Chemical Formula B-3-1 or Chemical Formula B-3-2, each moiety including at least one aromatic ring.

[Chemical Formula B-3-1]

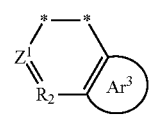

[Chemical Formula B-3-2]

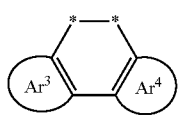

In Chemical Formula B-3-1 and Chemical Formula B-3-2, $Ar^3$ and $Ar^4$ may each independently be a substituted or unsubstituted C6 to C30 arene group or a substituted or unsubstituted C3 to C30 heteroarene group, in Chemical Formula B-3-1, $Z^1$ and $Z^2$ may each independently be $CR^a$ or N, wherein $R^a$ may be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, and adjacent pairs of *'s inside the at least one aromatic ring are linking portions with an N-containing hexagonal ring of Chemical Formula 1.

The moiety represented by Chemical Formula B-3-1 may be one moiety of a set of moieties represented by Chemical Formula B-3-11.

[Chemical Formula B-3-11]

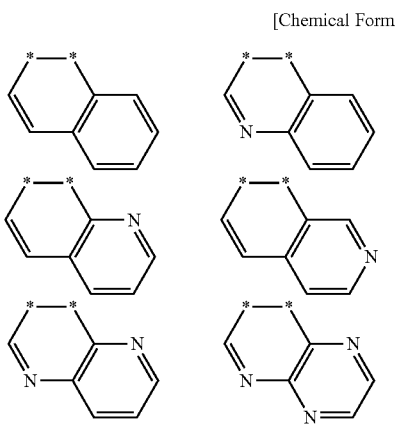

In Chemical Formula B-3-11,
hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and
adjacent pairs of *'s inside the at least one aromatic ring are linking portions with an N-containing hexagonal ring of Chemical Formula 1.

The moiety represented by Chemical Formula B-3-2 may be one moiety of a set of moieties represented by Chemical Formula B-3-21.

[Chemical Formula B-3-21]

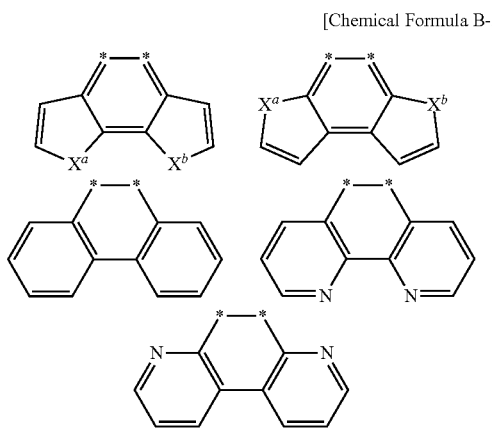

In Chemical Formula B-3-21,
hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group,
adjacent pairs of *'s inside the at least one aromatic ring may be linking portions with an N-containing hexagonal ring of Chemical Formula 1, and
$X^a$ and $X^b$ may each independently be —O—, —S—, —Se—, —Te—, —NR$^a$—, —SiR$^b$R$^c$— or —GeR$^d$R$^e$—, wherein R$^a$, R$^b$, R$^c$, R$^d$, and R$^e$ may each independently be hydrogen, deuterium, a halogen, a substituted or unsubstituted C1 to C10 alkyl group, or a substituted or unsubstituted C6 to C10 aryl group.

$L^1$ may be represented by Chemical Formula 1A-1 or Chemical Formula 1B-1.

[Chemical Formula 1A-1]

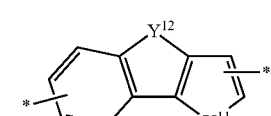
(1A-1a)

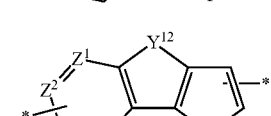
(1A-1b)

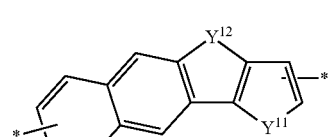
(1A-1c)

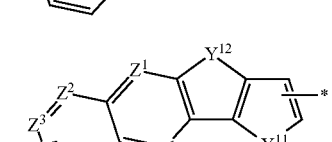
(1A-1d)

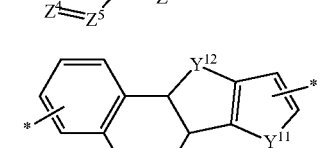
(1A-1e)

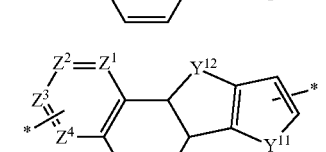
(1A-1f)

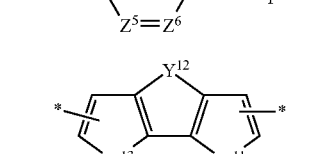
(1A-1g)

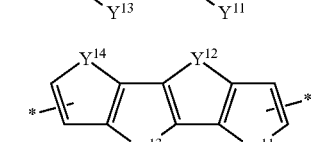
(1A-1h)

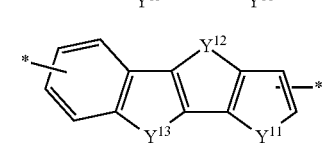
(1A-1i)

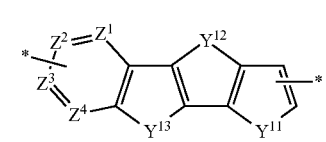
(1A-1j)

In Chemical Formula 1A-1,
hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group,
$Y^{11}$, $Y^{12}$, $Y^{13}$, and $Y^{14}$ may each independently be O, S, Se, Te, S(=O), S(=O)$_2$, NR$^a$, or SiR$^b$R$^c$, wherein R$^a$, R$^b$, and $R^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or $CR^X$, wherein $R^x$ may be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1A-1b and Chemical Formula 1A-1j is N, and at least one of $Z^1$ to $Z^6$ in Chemical Formula 1A-1d and Chemical Formula 1A-1 f is N, and

* on a left side of Chemical Formula 1A-1 is a portion that is bound to N of —N($R^1$)($R^2$) of Chemical Formula 1, and * on a right side of Chemical Formula 1A-1 is a portion that is bound to $Ar^1$ of Chemical Formula 1.

[Chemical Formula 1B-1]

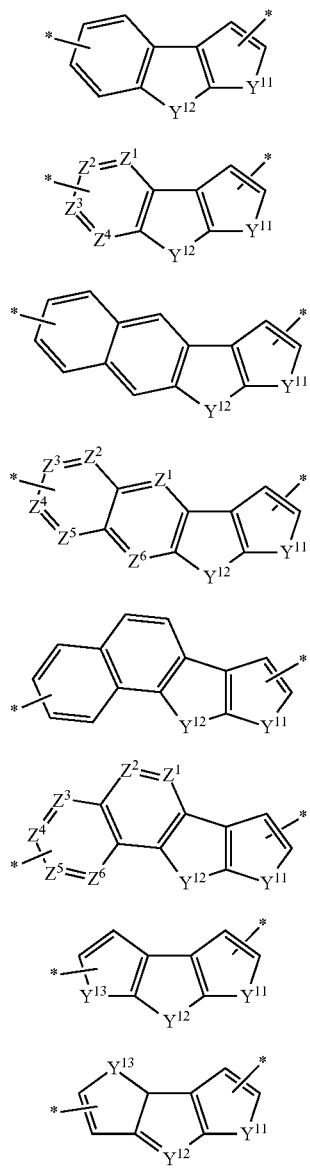

In Chemical Formula 1B-1, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{11}$, $Y^{12}$, and $Y^{13}$ may each independently be O, S, Se, Te, S(=O), S(=O)$_2$, $NR^a$, or $SiR^bR^c$, wherein $R^a$, $R^b$, and $R^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or $CR^X$, wherein $R^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1B-1 b and Chemical Formula 1B-1 j may be N, and at least one of $Z^1$ to $Z^6$ in Chemical Formula 1B-1 d and Chemical Formula 1B-1 f may be N, and

* on a left side of Chemical Formula 1B-1 is a portion that is bound to N of —N($R^1$)($R^2$) of Chemical Formula 1, and * on a right side of Chemical Formula 1B-1 is a portion that is bound to $Ar^1$ of Chemical Formula 1.

$L^2$ may be represented by Chemical Formula 1C-1 or Chemical Formula 1D-1.

[Chemical Formula 1C-1]

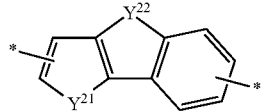

(1C-1a)

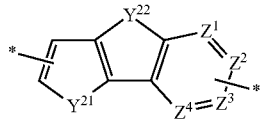

(1C-1b)

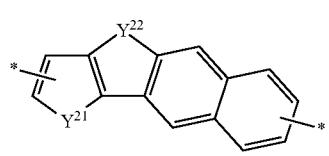

(1C-1c)

-continued

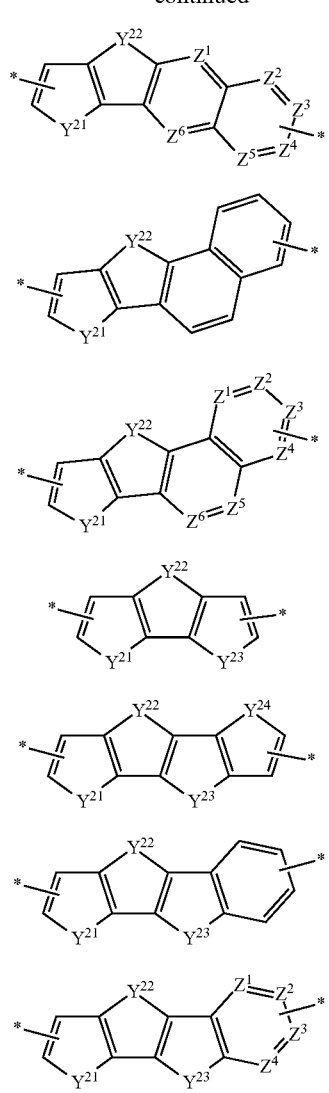

(1C-1d)
(1C-1e)
(1C-1f)
(1C-1g)
(1C-1h)
(1C-1i)
(1C-1j)

In Chemical Formula 1C-1, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, $Y^{23}$, and $Y^{24}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or CR$^x$, wherein R$^x$ may be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1C-1b and Chemical Formula 1C-1 j may be N, and at least one of $Z^1$ to $Z^6$ in Chemical Formula 1C-1d and Chemical Formula 1C-1 f may be N, and

* on a left side of Chemical Formula 1C-1 is a portion that is bound to Ar$^1$ of Chemical Formula 1, and * on a right side of Chemical Formula 1C-1 is a portion that is bound to N of —N(R$^3$)(R$^4$) of Chemical Formula 1.

[Chemical Formula 1D-1]

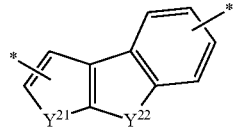 (1D-1a)

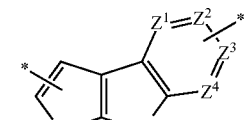 (1D-1b)

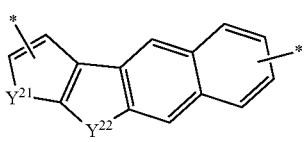 (1D-1c)

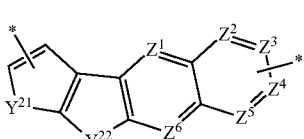 (1D-1d)

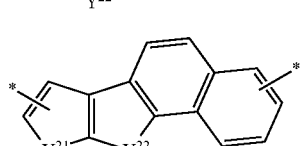 (1D-1e)

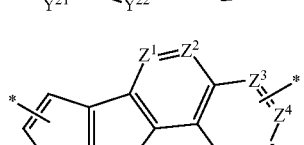 (1D-1f)

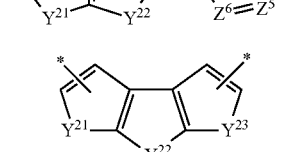 (1D-1g)

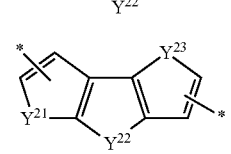 (1D-1h)

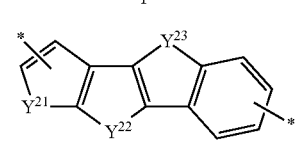 (1D-1i)

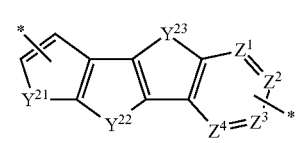 (1D-1j)

In Chemical Formula 1 D-1, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, and $Y^{23}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or CR$^x$, wherein R$^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1D-1 b and Chemical Formula 1 D-1 j is N and $Z^1$ to $Z^6$ in Chemical Formula 1D-1d and Chemical Formula 1 D-1 f is N, and

* on a left side of Chemical Formula 1 D-1 is a portion that is bound to Ar$^1$ of Chemical Formula 1, and * on a right side of Chemical Formula 1 D-1 is a portion that is bound to N of —N(R$^3$)(R$^4$) of Chemical Formula 1.

In Chemical Formula 1, *—N(R$^1$)(R$^2$) and *—N(R$^3$)(R$^4$) may each independently be represented by Chemical Formula D.

[Chemical Formula D]

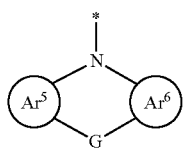

In Chemical Formula D,

Ar$^5$ and Ar$^6$ may each independently be a substituted or unsubstituted C6 to C30 arene group or a substituted or unsubstituted C3 to C30 heteroarene group, G may be a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and

* is a linking point with Chemical Formula 1.

Chemical Formula D may be represented by one of Chemical Formula D-1 to Chemical Formula D-5.

[Chemical Formula D-1]

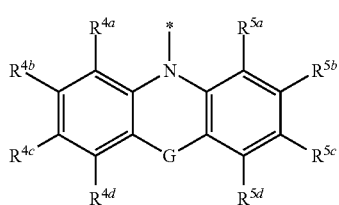

In Chemical Formula D-1,

G may be a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and $R^{4a}$ to $R^{4d}$ and $R^{5a}$ to $R^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, two adjacent to each other of $R^{4a}$ to $R^{4d}$ may be linked to each other to provide a five-membered aromatic ring or a six-membered aromatic ring and optionally two adjacent to each other of $R^{5a}$ to $R^{5d}$ may linked to each other to provide a five-membered aromatic ring or a 6-membered aromatic ring.

[Chemical Formula D-2]

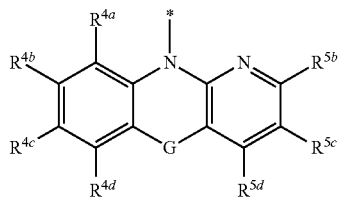

In Chemical Formula D-2,

G may be a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and $R^{4a}$ to $R^{4d}$ and $R^{5b}$ to $R^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, two adjacent to each other of $R^{4a}$ to $R^{4d}$ may be linked to each other to provide a five-membered aromatic ring or a six-membered aromatic ring, and optionally two adjacent to each other of $R^{5b}$ to $R^{5d}$ may linked to each other to provide a five-membered aromatic ring or a 6-membered aromatic ring.

[Chemical Formula D-3]

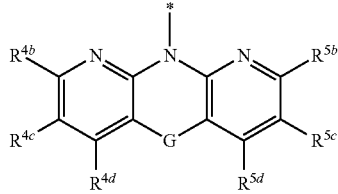

In Chemical Formula D-3,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4b}$ to R$^{4d}$ and R$^{5b}$ to R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4b}$ to R$^{4d}$ may be linked to each other to provide a five-membered aromatic ring or a six-membered aromatic ring, and optionally two adjacent to each other of R$^{5b}$ to R$^{5d}$ may linked to each other to provide a five-membered aromatic ring or a 6-membered aromatic ring.

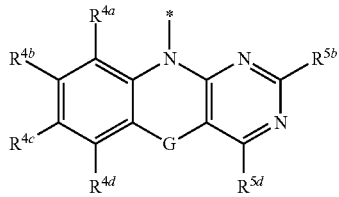

[Chemical Formula D-4]

In Chemical Formula D-4,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5b}$ and R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may linked to each other to provide a five-membered aromatic ring or a 6-membered aromatic ring.

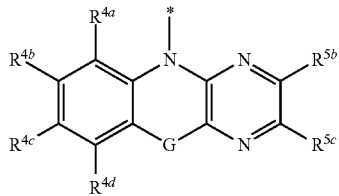

[Chemical Formula D-5]

In Chemical Formula D-5,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5b}$ and R$^{5c}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may be linked to each other to provide a five-membered aromatic ring or a six-membered aromatic ring, and optionally two adjacent to each other of R$^{5b}$ and R$^{5c}$ may linked to each other to provide a five-membered aromatic ring or a 6-membered aromatic ring.

A peak absorption wavelength of the infrared absorber may be in a wavelength region of about 750 nm to about 3000 nm.

According to some example embodiments, an infrared absorbing and/or blocking film including the infrared absorber is provided.

According to some example embodiments, a photoelectric device may include a first electrode and a second electrode facing each other, and a photoactive layer between the first electrode and the second electrode, wherein the photoactive layer includes an infrared absorber including the compound represented by Chemical Formula 1.

According to some example embodiments, a sensor including the photoelectric device is provided.

According to some example embodiments, an electronic device including the photoelectric device or the sensor is provided.

According to some example embodiments, a photoelectric device may include a first electrode and a second electrode facing each other, a photoactive layer between the first electrode and the second electrode, and a charge auxiliary layer between the photoactive layer and the first electrode, or the photoactive layer and the second electrode, wherein at least one of the photoactive layer or the charge auxiliary layer includes the infrared absorber includes the compound represented by Chemical Formula 1.

The photoactive layer may further include the infrared absorber.

According to some example embodiments, an image sensor may include a semiconductor substrate, a first photoelectric device on the semiconductor substrate, the first photoelectric device configured to selectively absorb light in a first infrared wavelength region, and an additional sensor configured to selectively absorb light in a separate wavelength region that is different from the first infrared wavelength region. The first photoelectric device may include an infrared absorber that includes the compound represented by Chemical Formula 1.

The additional sensor may be an infrared light sensor at least partially embedded within the semiconductor substrate, and the separate wavelength region may be a separate infrared wavelength region that is different from the first infrared wavelength region. The first photoelectric device and the infrared light sensor may overlap in a vertical direction that is perpendicular to an upper surface of the semiconductor substrate.

The additional sensor may include a plurality of photodiodes at least partially embedded within the semiconductor substrate, the plurality of photodiodes configured to selectively absorb light in separate visible wavelength regions. The first photoelectric device and the plurality of photodiodes may overlap in a vertical direction that is perpendicular to an upper surface of the semiconductor substrate.

The additional sensor may include at least one additional photoelectric device vertically stacked between the first photoelectric device and the semiconductor substrate, each separate photoelectric device of the at least one additional photoelectric device including a separate photoelectric conversion layer and configured to selectively absorb light in a separate, respective wavelength region that is different from the first infrared wavelength region.

The first photoelectric device may include a first electrode and a second electrode facing each other, and a photoactive layer between the first electrode and the second electrode, wherein the photoactive layer includes the infrared absorber.

The first photoelectric device may include a first electrode and a second electrode facing each other, a photoactive layer between the first electrode and the second electrode, and a charge auxiliary layer between the photoactive layer and the first electrode, or the photoactive layer and the second electrode. The charge auxiliary layer may include the infrared absorber.

The infrared absorber may exhibit good light absorption properties in the infrared region and thus may be effectively used for photoelectric devices and/or sensors.

DETAILED DESCRIPTION

Figure 1:
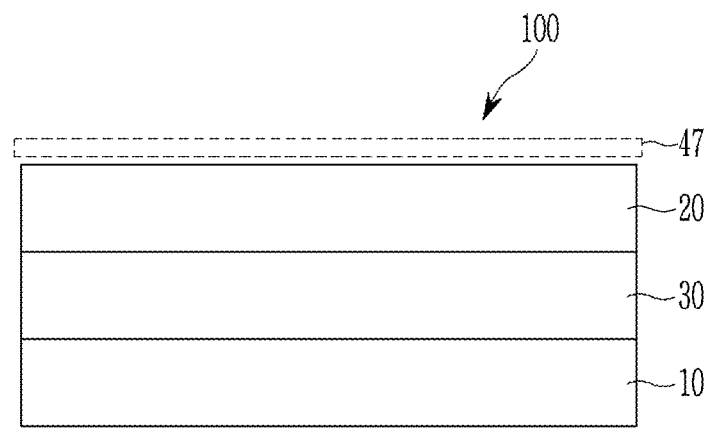
FIG. 1 is a cross-sectional view showing a photoelectric device according to some example embodiments.

Hereinafter, example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, parts having no relationship with the description are omitted for clarity of some example embodiments, and the same or similar constituent elements are indicated by the same reference numeral throughout the specification.

Hereinafter, "combination" includes a mixture of two or more, inter-substitution, and a laminate structure of two or more.

As used herein, when specific definition is not otherwise provided, "substituted" refers to replacement of a hydrogen of a compound or a functional group by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when specific definition is not otherwise provided, "'hetero" refers to one including 1 to 4 heteroatoms selected from N, O, S, Se, Te, Si, and P.

As used herein, when a definition is not otherwise provided, "aromatic ring" refers to a functional group in which all atoms in the cyclic functional group have a p-orbital, and wherein these p-orbitals are conjugated and "heteroaromatic ring" refers to the aromatic ring including a heteroatom. The "aromatic ring" refers to a C6 to C30 arene group, for example a C6 to C20 arene group or a C6 to C30 aryl group, for example a C6 to C20 aryl group. The "heteroaromatic ring" refers to a C3 to C30 heteroarene group, for example a C3 to C20 heteroarene group or a C6 to C30 heteroaryl group, for example a C6 to C20 heteroaryl group.

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. The heteroarene group means an arene group including 1 to 3 heteroatoms selected from N, O, S, Se, Te, P, and Si in the ring.

As used herein, when a definition is not otherwise provided, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heteroaryl group" refers to an aryl group including at least one heteroatom selected from N, O, S, Se, Te, P, and Si instead of carbon (C) in the ring. When the heteroaryl group is a fused ring, at least one of the rings of the heteroaryl group may have a heteroatom or each ring may have a heteroatom.

As used herein, when a definition is not otherwise provided, "ring" refers to an aromatic ring, a non-aromatic ring, a heteroaromatic ring, a hetero non-aromatic ring, a fused ring thereof, and/or a combination thereof. The aromatic ring are the same as described above and the non-aromatic ring may be a C3 to C30 cycloalkyl group, a C3 to C30 cycloalkenyl group, or a C3 to C30 cycloalkynyl group.

As used herein, when a definition is not otherwise provided, "halogen" may be one of F, Cl, Br, or I and the haloalkyl group may be an alkyl group in which at least one hydrogen is replaced by a halogen and may be, for example, a perfluoroalkyl group such as $-CF_3$.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is replaced by a cyano group. The cyano-containing group also refers to a divalent group such as $=CR^{x'}-(CR^xR^y)_p-CR^{y'}(CN)_2$ wherein $R^x$, $R^y$, $R^{x'}$, and $R^{y'}$ are independently hydrogen or a C1 to C10 alkyl group and p may be an integer of 0 to 10 (or 1 to 10). Specific examples of the cyano-containing group may be a dicyanomethyl group, a dicyanovinyl group, a cyanoethynyl group, and the like.

As used herein, when a definition is not otherwise provided, the "infrared wavelength region" includes a near-infrared/infrared wavelength region with a wavelength region of about 750 nm to about 3000 nm.

hereinafter, an infrared absorber according to some example embodiments is provided. The infrared absorber may be referred to herein interchangeably as an "infrared absorbing compound."

The infrared absorber may include a compound represented by Chemical Formula 1.

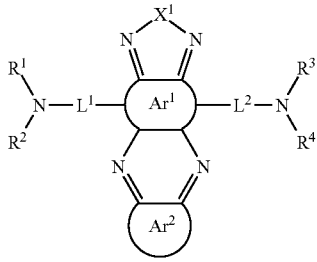

[Chemical Formula 1]

In Chemical Formula 1, $Ar^1$ may be a substituted or unsubstituted C6 to C30 aromatic ring, a substituted or unsubstituted C3 to C30 heteroaromatic ring, or a combination thereof, $Ar^2$ may be a substituted or unsubstituted C6 to C30 aromatic ring, a substituted or unsubstituted C3 to C30 heteroaromatic ring, or a combination thereof, $X^1$ may be O, S, Se, Te, S(=O), S(=O)$_2$, NR$^a$, CR$^b$R$^c$, or SiR$^d$R$^e$, wherein R$^a$, R$^b$, R$^c$, R$^d$, and R$^e$ may each independently be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, $R^1$, $R^2$, $R^3$, and $R^4$ may each independently be hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, $R^1$ and $R^2$ may each independently exist (e.g., are not linked to each other independently of $L^1$, $L^2$, and $Ar^1$) or be linked to each other (e.g., independently of $L^1$, $L^2$, and $Ar^1$) to form a ring (e.g., a first ring), and $R^3$ and $R^4$ may each independently exist or be linked to each other to form a ring (e.g., a second ring), and $L^1$ may be represented by Chemical Formula 1A or Chemical Formula 1B, and $L^2$ may be represented by Chemical Formula 1C or Chemical Formula 1D.

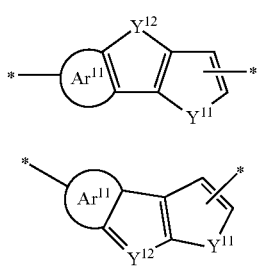

[Chemical Formula 1A]

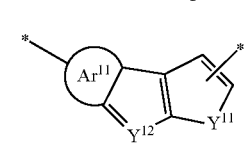

[Chemical Formula 1B]

In Chemical Formula 1A and Chemical Formula 1B, $Y^{11}$ and $Y^{12}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Ar^{11}$ may be a substituted or unsubstituted C6 to C30 aromatic ring (e.g., a substituted or unsubstituted C6 to C20 aromatic ring or a substituted or unsubstituted C6 to C10 aromatic ring), a substituted or unsubstituted C3 to C30 heteroaromatic ring (e.g., a substituted or unsubstituted C3 to C20 heteroaromatic ring or a substituted or unsubstituted C3 to C20 heteroaromatic ring), or a combination thereof, and

* on the left (e.g., on a left side of Chemical Formula 1A and Chemical Formula 1B) may be a portion that is bound to N of —N(R$^1$)(R$^2$) of Chemical Formula 1, and * on the right (e.g., on a right side of Chemical Formula 1A and Chemical Formula 1B) may be a portion that is bound to $Ar^1$ of Chemical Formula 1.

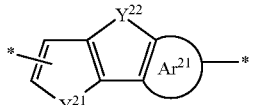

[Chemical Formula 1C]

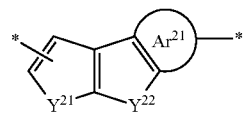

[Chemical Formula 1D]

In Chemical Formula 1C and Chemical Formula 1D, $Y^{21}$ and $Y^{22}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Ar^{21}$ may be a substituted or unsubstituted C6 to C30 aromatic ring (e.g., a substituted or unsubstituted C6 to C20 aromatic ring or a substituted or unsubstituted C6 to C10 aromatic ring), a substituted or unsubstituted C3 to C30 heteroaromatic ring (e.g., a substituted or unsubstituted C3 to C20 heteroaromatic ring or a substituted or unsubstituted C3 to C20 heteroaromatic ring), or a combination thereof, and

* on the left (e.g., on a left side of Chemical Formula 1C and Chemical Formula 1D) may be a portion that is bound to $Ar^1$ of Chemical Formula 1, and * on the right (e.g., on a right side of Chemical Formula 1C and Chemical Formula 1D) may be a portion that is bound to N of —N(R$^3$)(R$^4$) of Chemical Formula 1.

The infrared absorber represented by Chemical Formula 1 has a donor-acceptor-donor structure in which amine groups (*—N(R$^1$)(R$^2$) and *—N(R$^3$)(R$^4$)) having electron donating properties are linked to the core (N—X$^1$—N-containing pentagonal ring and N-containing hexagonal ring in Chemical Formula 1) of a conjugated structure having electron-accepting properties) by L$^1$ and L$^2$, and thus it may have strong charge transfer characteristics and low bandgap energy, result in effectively absorbing the light in the infrared wavelength region.

In Chemical Formula 1, $L^1$ and $L^2$ are linkers including three or more aromatic rings, and two or more heteroaromatic rings ($Y^{11}$-containing pentagonal ring and $Y^{12}$-containing pentagonal ring, $Y^{21}$-containing pentagonal ring, and $Y^{22}$-containing pentagonal ring) of these aromatic rings, a heteroatom included in the ring may enhance charge transfer characteristics, reduce the bandgap energy, and shift the absorption wavelength to a long wavelength region.

In Chemical Formula 1, $Ar^1$ may be a substituted or unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, $Ar^1$ may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

In Chemical Formula 1, $Ar^1$ may be one of the moieties (e.g., one moiety of a set of moieties) represented by Chemical Formula A-1, each moiety including at least one aromatic ring and left and right linking groups.

*'s of the left and right linking groups are portions that are bound to $L^1$ and $L^2$ of Chemical Formula 1 (e.g., *'s of the left and right linking groups are linking portions linked to separate, respective ones of $L^1$ and $L^2$ of Chemical Formula 1).

In Chemical Formula 1, $Ar^1$ may be one moiety of a set of moieties represented by Chemical Formula A-2, each moiety including at least one aromatic ring and left and right linking groups.

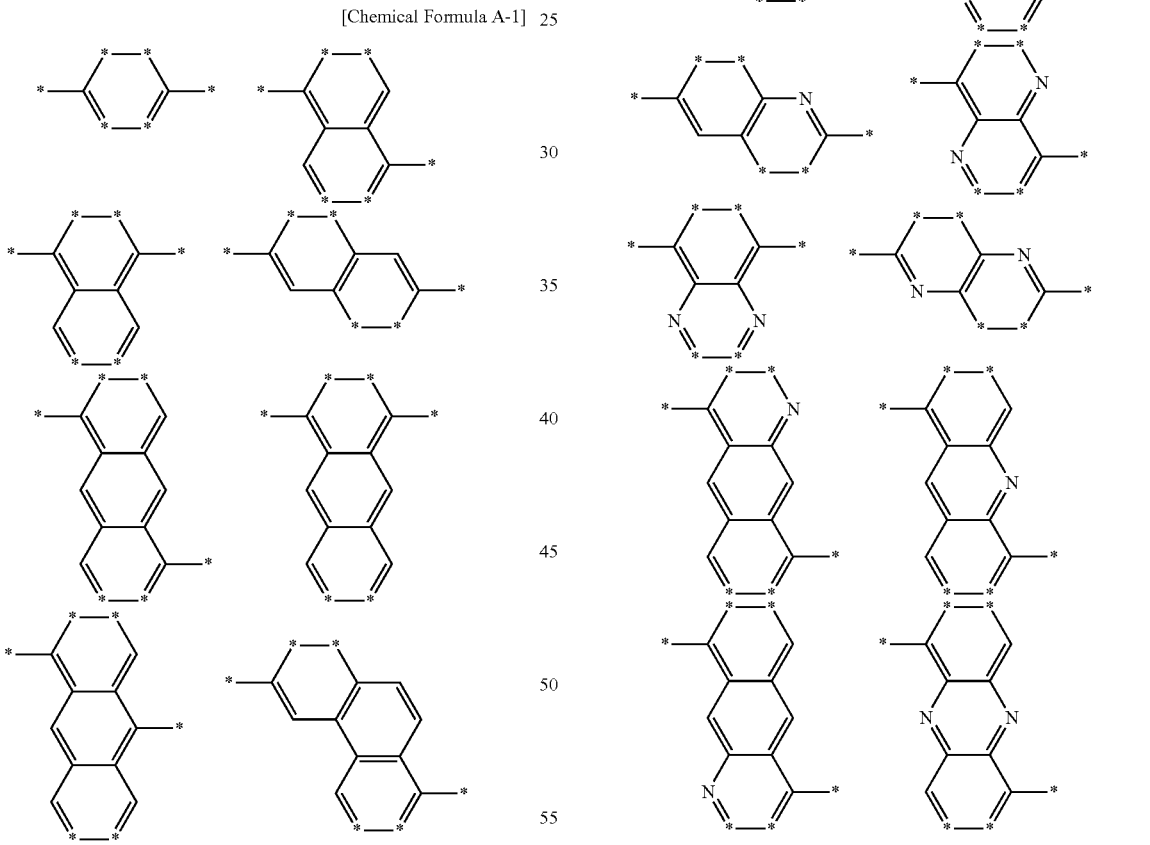

[Chemical Formula A-1]

[Chemical Formula A-2]

In Chemical Formula A-1,
hydrogen of each aromatic ring may be replaced by deuterium, a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and In Chemical Formula A-2,
hydrogen of each aromatic ring may be replaced by deuterium, a halogen, a cyano group, a C1 to C10 alkyl group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and

*'s of the left and right linking groups are portions that are bound to $L^1$ and $L^2$ of Chemical Formula 1 (e.g., *'s of the left and right linking groups are linking portions linked to separate, respective ones of $L^1$ and $L^2$ of Chemical Formula 1).

In Chemical Formula 1, $Ar^2$ may be a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene, or a substituted or unsubstituted pyrene ring.

In Chemical Formula 1, $Ar^2$ may be a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

In Chemical Formula 1, $Ar^2$ may be one moiety of a set of moieties represented by Chemical Formula B-1, each moiety including at least one aromatic ring.

[Chemical Formula B-1]

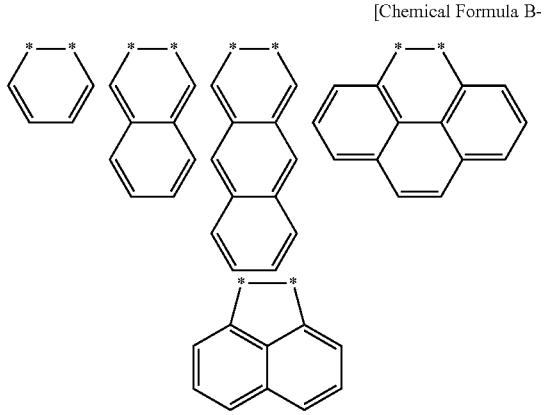

In Chemical Formula B-1, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and adjacent pairs of *'s inside the at least one aromatic ring are linking portions with an N-containing hexagonal ring of Chemical Formula 1.

In Chemical Formula 1, $Ar^2$ may be one moiety of a set of moieties represented by Chemical Formula B-2, each moiety including at least one aromatic ring.

[Chemical Formula B-2]

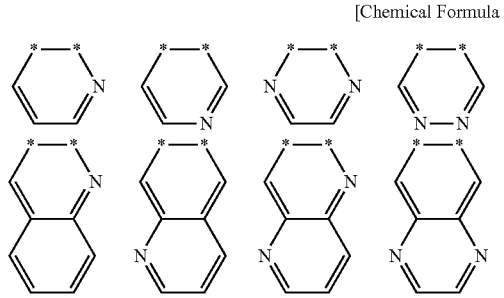

-continued

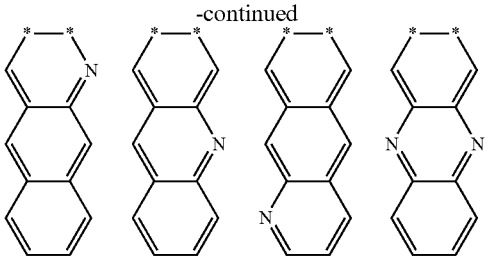

In Chemical Formula B-2, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and adjacent pairs of *'s inside the at least one aromatic ring may be linking portions with an N-containing hexagonal ring of Chemical Formula 1.

In Chemical Formula 1, $Ar^2$ may be one moiety of a set of moieties represented by Chemical Formula B-3-1 or Chemical Formula B-3-2, each moiety including at least one aromatic ring.

[Chemical Formula B-3-1]

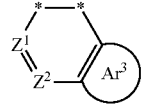

[Chemical Formula B-3-2]

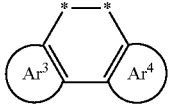

In Chemical Formula B-3-1 and Chemical Formula B-3-2, $Ar^3$ and $Ar^4$ may each independently be a substituted or unsubstituted C6 to C30 arene group or a substituted or unsubstituted C3 to C30 heteroarene group, In Chemical Formula B-3-1, $Z^1$ and $Z^2$ may each independently be $CR^a$ or N, wherein $R^a$ may be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, and adjacent pairs of *'s inside the at least one aromatic ring may be linking portions with an N-containing hexagonal ring of Chemical Formula 1.

A moiety represented by Chemical Formula B-3-1 may be one moiety of a set of moieties represented by Chemical Formula B-3-11.

[Chemical Formula B-3-11]

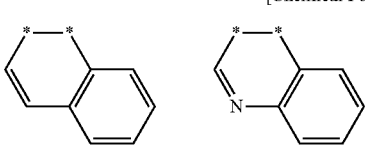

-continued

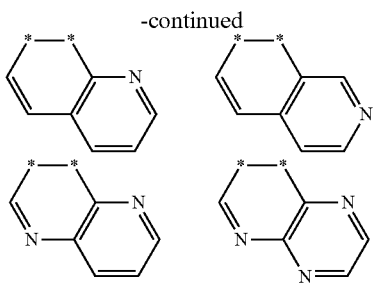

In Chemical Formula B-3-11, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and adjacent pairs of *'s inside the at least one aromatic ring may be linking portions with an N-containing hexagonal ring of Chemical Formula 1.

A moiety represented by Chemical Formula B-3-2 may be one moiety of a set of moieties represented by Chemical Formula B-3-21.

[Chemical Formula B-3-21]

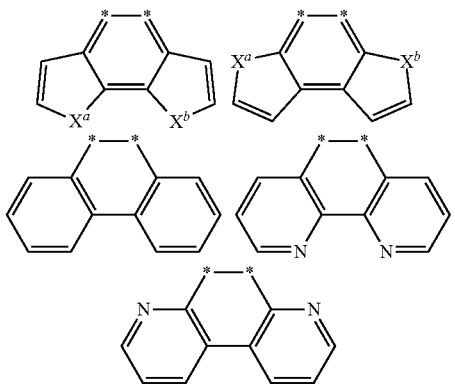

In Chemical Formula B-3-21, hydrogen of each aromatic ring may be replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, adjacent pairs of *'s inside the at least one aromatic ring may be linking portions with an N-containing hexagonal ring of Chemical Formula 1, and $X^a$ and $X^b$ may each independently be —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ may each independently be hydrogen, deuterium, a halogen, a substituted or unsubstituted C1 to C10 alkyl group, or a substituted or unsubstituted C6 to C10 aryl group.

For example, in Chemical Formula B-3-11 and Chemical Formula B-3-21, the halogen may be any one of F, Cl, Br or I, and the haloalkyl group may be, for example, an alkyl group in which at least one hydrogen is replaced by a halogen, such as —CF$_3$.

In Chemical Formula 1A, $Y^{11}$ may be O, S, Se or Te, and $Y^{12}$ may be NR$^a$.

In Chemical Formula 1B, $Y^{11}$ may be O, S, Se or Te, and $Y^{12}$ may be NR$^a$, where R$^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1C, $Y^{21}$ may be O, S, Se or Te, and $Y^{22}$ may be NR$^a$, where R$^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1D, $Y^{21}$ may be O, S, Se or Te, and $Y^{22}$ may be NR$^a$, where R$^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

$L^1$ may be represented by Chemical Formula 1A-1 or Chemical Formula 1B-1.

[Chemical Formula 1A-1]

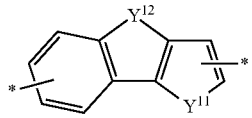 (1A-1a)

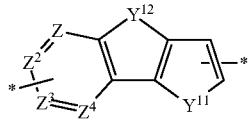 (1A-1b)

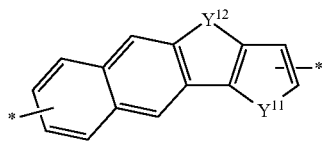 (1A-1c)

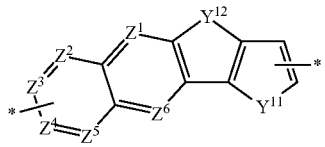 (1A-1d)

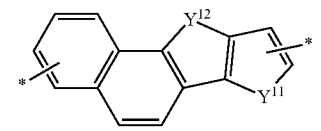 (1A-1e)

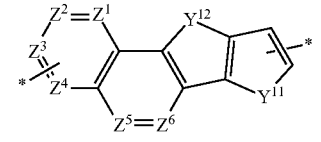 (1A-1f)

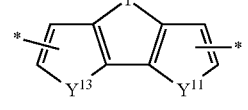 (1A-1g)

-continued (1A-1h)
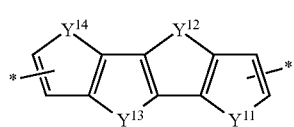

(1A-1i)
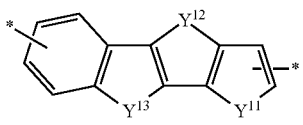

(1A-1j)
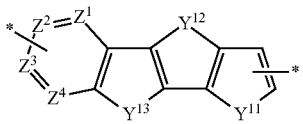

In Chemical Formula 1A-1, hydrogen of each aromatic ring may be optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{11}$, $Y^{12}$, $Y^{13}$, and $Y^{14}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or CR$^x$, wherein R$^x$ may be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1A-1b and Chemical Formula 1A-1j is N, and at least one of $Z^1$ to $Z^6$ in Chemical Formula 1A-1d and Chemical Formula 1A-1 f is N,

* on the left (e.g., on a left side of Chemical Formula 1A-1) may be a portion that is bound to N of —N(R$^1$)(R$^2$) of Chemical Formula 1, and * on the right (e.g., on a right side of Chemical Formula 1A-1) may be a portion that is bound to Ar$^1$ of Chemical Formula 1.

In Chemical Formula 1A-1, $Y^{11}$ may be O, S, Se or Te, and $Y^{12}$ may be NR$^a$, where R$^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1A-1g to Chemical Formula 1A-1 i, $Y^{11}$ and $Y^{12}$ may each independently be O, S, Se or Te, and $Y^{13}$ may be NR$^a$, where R$^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

[Chemical Formula 1B-1]

(1B-1a)
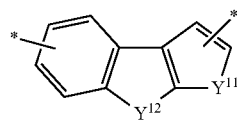

(1B-1b)
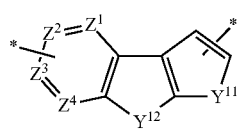

(1B-1c)
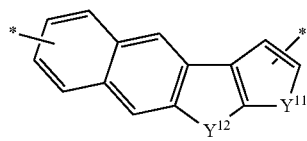

(1B-1d)
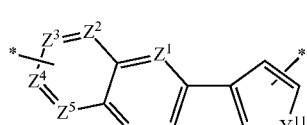

(1B-1e)
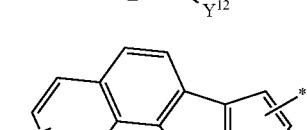

(1B-1f)
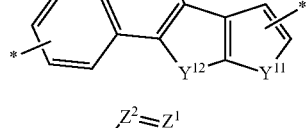

(1B-1g)
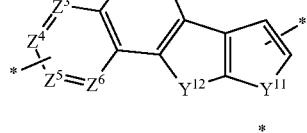

(1B-1h)
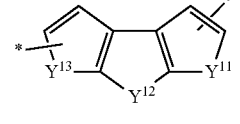

(1B-1i)
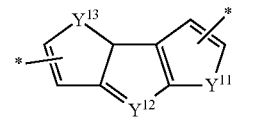

(1B-1j)
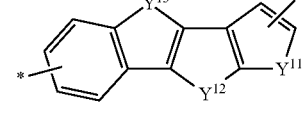

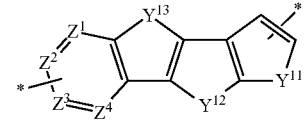

In Chemical Formula 1B-1, hydrogen of each aromatic ring may be optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{11}$, $Y^{12}$, and $Y^{13}$ may each independently be O, S, Se, Te, S(=O), S(=O)$_2$, NR$^a$, or SiR$^b$R$^c$, wherein R$^a$, R$^b$, and R$^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or $CR^X$, wherein $R^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1B-1 b and Chemical Formula 1B-1 j may be N, and at least one of $Z^1$ to $Z^6$ in Chemical Formula 1B-1 d and Chemical Formula 1B-1 f may be N, and

* on the left (e.g., on a left side of Chemical Formula 1B-1) may be a portion that is bound to N of —N($R^1$)($R^2$) of Chemical Formula 1, and * on the right (e.g., on a right side of Chemical Formula 1B-1) may be a portion that is bound to $Ar^1$ of Chemical Formula 1.

In Chemical Formula 1B-1, $Y^{11}$ may be O, S, Se, or Te, and $Y^{12}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1B-1 g to Chemical Formula 1B-1 i, $Y^{11}$ and $Y^{12}$ may each independently be O, S, Se, or Te, and $Y^{13}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

$L^2$ may be represented by Chemical Formula 1C-1 or Chemical Formula 1D-1.

[Chemical Formula 1C-1]

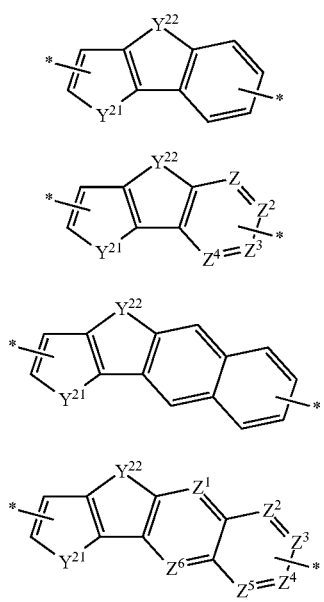

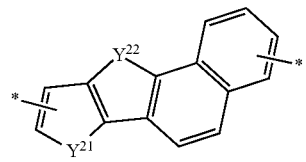

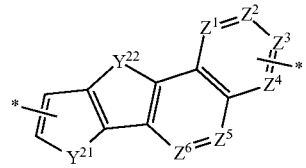

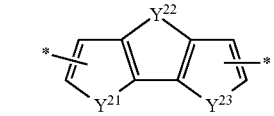

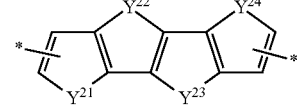

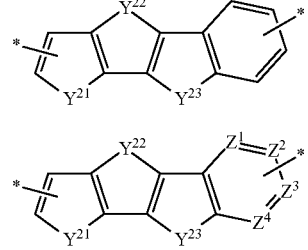

In Chemical Formula 1C-1, hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, $Y^{23}$, and $Y^{24}$ may each independently be O, S, Se, Te, S(=O), S(=O)$_2$, $NR^a$, or $SiR^bR^c$, wherein $R^a$, $R^b$, and $R^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or $CR^X$, wherein $R^x$ may be hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1C-1b and Chemical Formula 1C-1 j may be N, and at least one of $Z^1$ to $Z^6$ in Chemical Formula 1C-1d and Chemical Formula 1C-1 f may be N, and

* on the left (e.g., on a left side of Chemical Formula 1C-1) may be a portion that is bound to $Ar^1$ of Chemical Formula 1, and * on the right (e.g., on a right side of Chemical Formula 1C-1) may be a portion that is bound to N of —N($R^3$)($R^4$) of Chemical Formula 1.

In Chemical Formula 1C-1, $Y^{21}$ may be O, S, Se, or Te, and $Y^{22}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1C-1 g to Chemical Formula 1C-1 i, $Y^{21}$ and $Y^{22}$ may each independently be O, S, Se, or Te, and $Y^{23}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

[Chemical Formula 1D-1]

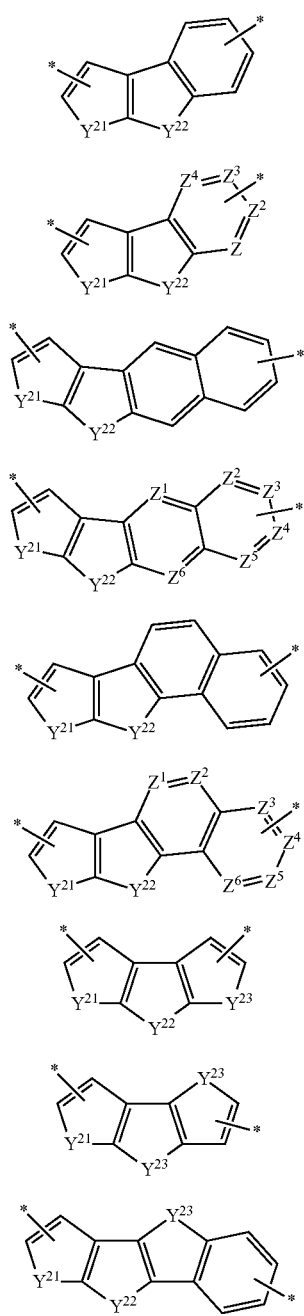

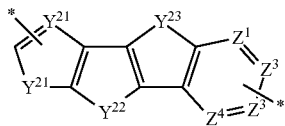

In Chemical Formula 1D-1, hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, and $Y^{23}$ may each independently be O, S, Se, Te, S(=O), S(=O)$_2$, $NR^a$, or $SiR^bR^c$, wherein $R^a$, $R^b$, and $R^c$ may each independently be hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ may each independently be N or $CR^x$, wherein $R^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1B-1 b and Chemical Formula 1B-1 j may be N, and at least one of $Z^1$ to $Z^6$ in Chemical Formula 1B-1 d and Chemical Formula 1B-1 f may be N, and \* on the left (e.g., on a left side of Chemical Formula 1D-1) may be a portion that is bound to $Ar^1$ of Chemical Formula 1, and \* on the right (e.g., on a right side of Chemical Formula 1D-1) may be a portion that is bound to N of —N(R$^3$)(R$^4$) of Chemical Formula 1.

In Chemical Formula 1D-1, $Y^{21}$ may be O, S, Se or Te, and $Y^{22}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

In Chemical Formula 1D-1 g to Chemical Formula 1D-1 i, $Y^{21}$ and $Y^{22}$ may each independently be O, S, Se, or Te, and $Y^{23}$ may be $NR^a$, where $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof.

The $L^1$ and $L^2$ may be linked at a symmetric position with respect to $Ar^1$ or may be linked at an asymmetric position.

In Chemical Formula 1, *—N(R$^1$)(R$^2$) and *—N(R$^3$)(R$^4$) may each independently be represented by Chemical Formula D.

[Chemcial Formula D]

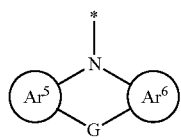

In Chemical Formula D,

Ar$^5$ and Ar$^6$ may each independently be a substituted or unsubstituted C6 to C30 arene group or a substituted or unsubstituted C3 to C30 heteroarene group, G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and

* is a linking point with Chemical Formula 1.

Chemical Formula D may be represented by one of Chemical Formula D-1 to Chemical Formula D-5.

[Chemical Formula D-1]

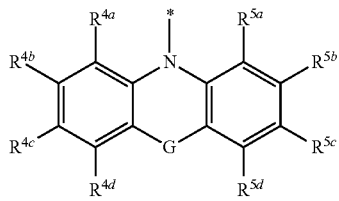

In Chemical Formula D-1,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5a}$ to R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may be linked to each other to provide a five-membered aromatic ring or a six-membered aromatic ring, and optionally two adjacent to each other of R$^{5a}$ to R$^{5d}$ may linked to each other to provide a five-membered aromatic ring or a 6-membered aromatic ring.

[Chemical Formula D-2]

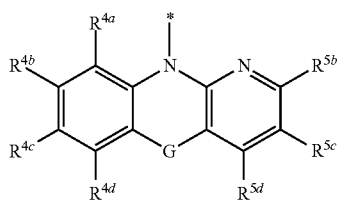

In Chemical Formula D-2,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5b}$ to R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may be linked to each other to provide a five-membered aromatic ring or a six-membered aromatic ring, and optionally two adjacent to each other of R$^{5b}$ to R$^{5d}$ may linked to each other to provide a five-membered aromatic ring or a 6-membered aromatic ring.

[Chemical Formula D-3]

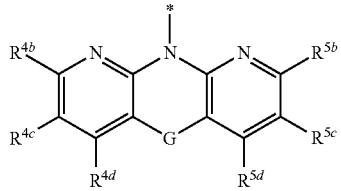

In Chemical Formula D-3,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4b}$ to R$^{4d}$ and R$^{5b}$ to R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4b}$ to R$^{4d}$ may be linked to each other to provide a five-membered aromatic ring or a six-membered aromatic ring, and optionally two adjacent to each other of R$^{5b}$ to R$^{5d}$ may linked to each other to provide a five-membered aromatic ring or a 6-membered aromatic ring.

[Chemical Formula D-4]

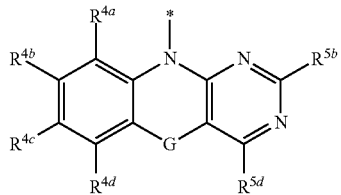

In Chemical Formula D-4,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5b}$ and R$^{5d}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may linked to each other to provide a five-membered aromatic ring or a 6-membered aromatic ring.

[Chemical Formula D-5]

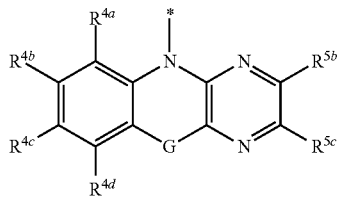

In Chemical Formula D-5,

G may be a single bond, —O—, —S—, —Se—, —Te—, —N═, —NR$^a$—, —SiR$^b$R$^c$—, —GeR$^d$R$^e$—, —(CR$^f$R$^g$)$_n$—, or —(C(R$^h$)═C(R$^i$))—, wherein R$^a$, R$^b$, R$^c$, R$^d$, R$^e$, R$^f$, R$^g$, R$^h$, and R$^i$ may each independently be hydrogen, deuterium, a halogen, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ may each independently exist or may be linked to each other to provide a ring, and n of —(CR$^f$R$^g$)$_n$— is an integer of 1 or 2, and R$^{4a}$ to R$^{4d}$ and R$^{5b}$ and R$^{5c}$ may each independently be hydrogen, deuterium, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, R$^{4a}$ to R$^{4d}$ may be linked to each other to provide a five-membered aromatic ring or a six-membered aromatic ring, and optionally two adjacent to each other of R$^{5b}$ and R$^{5c}$ may linked to each other to provide a five-membered aromatic ring or a 6-membered aromatic ring.

The infrared absorber may absorb light in an infrared wavelength region and the infrared absorber may have a peak absorption wavelength (λmax) of, for example, greater than or equal to about 750 nm, greater than or equal to about 780 nm, greater than or equal to about 790 nm, greater than or equal to about 800 nm, greater than or equal to about 810 nm, greater than or equal to about 820 nm, greater than or equal to about 830 nm, greater than or equal to about 840 nm, or greater than or equal to about 850 nm. The infrared absorber may have a peak absorption wavelength ($λ_{max}$) of, for example, less than or equal to about 3000 nm, less than or equal to about 2900 nm, less than or equal to about 2800 nm, less than or equal to about 2700 nm, less than or equal to about 2600 nm, less than or equal to about 2500 nm, less than or equal to about 2400 nm, less than or equal to about 2300 nm, less than or equal to about 2200 nm, or less than or equal to about 2100 nm.

The infrared absorber may exhibit good charge transfer characteristics, and thus, it has good photoelectric conversion characteristics that absorb (e.g., selectively absorb) light and/or convert it (e.g., photoelectrically convert it) into an electrical signal, and thus may be effectively used as a photoelectric conversion material for photoelectric devices.

Some example embodiments provide an infrared absorbing/blocking film (absorbing and/or blocking film) including the infrared absorber.

The infrared absorbing/blocking film may be applied to various fields requiring light absorption characteristics in an infrared wavelength region.

The infrared absorber has both light absorption characteristics and photoelectric characteristics in a near-infrared wavelength region/infrared wavelength region, and thus it may be effectively used as a photoelectric conversion material.

FIG. 1 is a cross-sectional view of a photoelectric device according to some example embodiments.

Referring to FIG. 1, a photoelectric device 100 according to some example embodiments includes a first electrode 10 and a second electrode 20 facing each other and a photoactive layer 30 between the first electrode 10 and the second electrode 20.

A substrate (not shown) may be disposed at the side of the first electrode 10 or the second electrode 20. The substrate may be for example made of (e.g., may at least partially comprise) an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 or the second electrode 20 is an anode and the other is a cathode. For example, the first electrode 10 may be a cathode and the second electrode 20 may be an anode.

At least one of the first electrode 10 or the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AITO), and/or fluorine doped tin oxide (FTO), or a metal thin layer of a single layer or a multilayer. When one of the first electrode 10 or the second electrode 20 is a non-light-transmitting electrode, it may be made of, for example, an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The photoactive layer 30 is a layer including a p-type semiconductor and an n-type semiconductor configured to provide a pn junction, which is a layer that may produce excitons by receiving light from outside (e.g., an exterior of the photoactive layer 30) and then separating holes and electrons from the produced excitons.

The p-type semiconductor and the n-type semiconductor may independently be a light absorbing material that is configured to absorb (e.g., selectively absorb) light in at least one portion of a wavelength region and the aforementioned infrared absorber may be a p-type semiconductor or an n-type semiconductor. For example, the aforementioned infrared absorber may be used for a p-type semiconductor and fullerene or a fullerene derivative may be included as an n-type semiconductor.

Accordingly, it will be understood that the photoactive layer 30 may at least partially comprise the aforementioned infrared absorber (e.g., may include the infrared absorber and either fullerene or a fullerene derivative). Additionally, it will be understood that the photoactive layer 30 may have a peak absorption wavelength ($\lambda_{max}$) of, for example, greater than or equal to about 750 nm, greater than or equal to about 770 nm, greater than or equal to about 780 nm, greater than or equal to about 790 nm, greater than or equal to about 800 nm, greater than or equal to about 810 nm, greater than or equal to about 820 nm, or greater than or equal to about 830 nm, and/or a peak absorption wavelength ($\lambda_{max}$) of about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm. The photoactive layer 30, and thus the photoelectric device 100 may have improved infrared light absorption characteristics (e.g., may have improved sensitivity to light in an infrared wavelength region, improved absorbance of light in the infrared wavelength region, etc.) and thus improved photoelectric conversion performance and/or efficiency and/or improved thermal stability based on the photoactive layer including the aforementioned infrared absorber. In some example embodiments, the photoactive layer 30 may be an infrared absorbing/blocking film that includes the infrared absorber.

The photoactive layer 30 may include an intrinsic layer in which the aforementioned infrared absorber (e.g., p-type semiconductor) and fullerene or a fullerene derivative (e.g., n-type semiconductor), which may be co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The photoactive layer 30 may further include a p-type layer and/or an n-type layer in addition to the intrinsic layer. The p-type layer may include the aforementioned infrared absorber (e.g., p-type semiconductor) and the n-type layer may include the aforementioned n-type semiconductor. For example, they may be included in various combinations of p-type layer/I layer, I layer/n-type layer, p-type layer/I layer/n-type layer, and the like.

The photoelectric device 100 may further include an auxiliary layer between the first electrode 10 and the photoactive layer 30 and/or the second electrode 20 and the photoactive layer 30. The auxiliary layer may be a charge auxiliary layer or an optical auxiliary layer.

Figure 2:
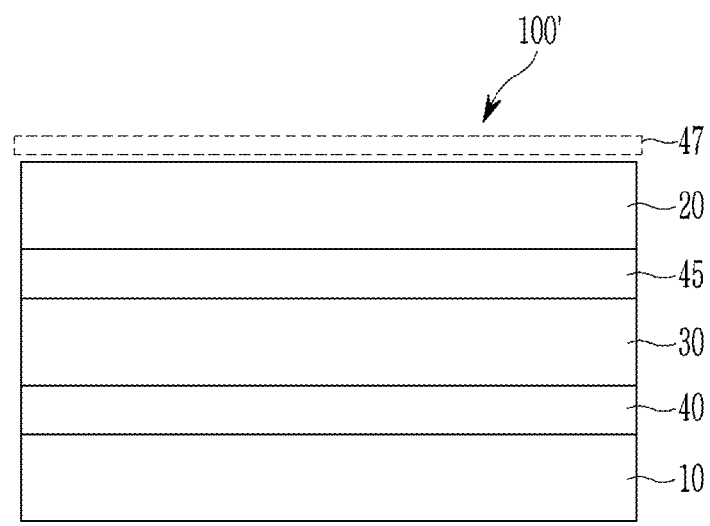
FIG. 2 is a cross-sectional view showing a photoelectric device according to some example embodiments.

This photoelectric device is shown in FIG. 2.

FIG. 2 is a cross-sectional view showing a photoelectric device according to some example embodiments.

Referring to FIG. 2, the photoelectric device 100' according to some example embodiments includes a first electrode 10 and a second electrode 20 facing each other, and a photoactive layer 30 between the first electrode 10 and the second electrode 20, like some example embodiments, including the example embodiments shown in FIG. 1.

In some example embodiments, including the example embodiments shown in FIG. 2, and unlike some example embodiments, including the example embodiments shown in FIG. 1, the photoelectric device 100' further includes charge auxiliary layers 40 and 45 (also referred to herein as first and second charge auxiliary layers, respectively) between the first electrode 10 and the photoactive layer 30, and between the second electrode 20 and the photoactive layer 30, respectively. The charge auxiliary layers 40 and 45 facilitate the movement of holes and electrons separated from the photoactive layer 30 to increase efficiency of the photoelectric device 100'. In some example embodiments, only one of the first auxiliary layer 40 or the second auxiliary layer 45 is included in the photoelectric device 100'.

The charge auxiliary layers 40 and 45 may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and/or 45 may include for example an organic material, an inorganic material, or an organic-inorganic material. The organic material may be an organic material having hole or electron characteristics and the inorganic material may be for example a metal oxide such as a molybdenum oxide, a tungsten oxide, or a nickel oxide.

The charge auxiliary layers 40 and 45 may include for example the aforementioned infrared absorber. In some example embodiments, the charge auxiliary layers 40 and/or 45 may include the aforementioned infrared absorber and the photoactive layer 30 may also include the aforementioned infrared absorber. In some example embodiments, the charge auxiliary layers 40 and/or 45 may include the aforementioned infrared absorber and the photoactive layer 30 may not include the aforementioned infrared absorber. The charge auxiliary layers 40 and/or 45, and thus the photoelectric device 100', may have improved infrared light absorption characteristics (e.g., may have improved sensitivity to light in an infrared wavelength region, improved absorbance of light in the infrared wavelength region, etc.) and thus improved photoelectric conversion performance and/or efficiency, based on the charge auxiliary layers 40 and/or 45 including the aforementioned infrared absorber. In some example embodiments, a photoelectric device 100' may include a first electrode 10 and a second electrode 20 facing each other, a photoactive layer 30 between the first electrode 10 and the second electrode 20, and one or more charge auxiliary layers 40 and/or 45, where the one or more charge auxiliary layers 40 and/or 45 may include a first charge auxiliary layer 40 that is between the photoactive layer 30 and the first electrode 10 and/or a second charge auxiliary layer 45 that is between the photoactive layer 30 and the second electrode 20, and wherein at least one of the photoactive layer 30 or the one or more charge auxiliary layers 40 and/or 45 include the aforementioned infrared absorber.

The optical auxiliary layer may be disposed in the light incident direction of the photoelectric device. For example, when the second electrode 20 is a light receiving electrode (e.g., the electrode proximate to a surrounding environment from which light is received at the photoelectric device 100'), the optical auxiliary layer may be disposed on the photoactive layer 30. For example, the optical auxiliary layer may be disposed between the second electrode 20 and the photoactive layer 30.

The photoelectric devices 100 and 100' may further include an anti-reflection layer 47 on one surface of the first electrode 10 or the second electrode 20. The anti-reflection layer 47 is disposed at a light incidence side and lowers reflectance of light of incident light and thereby light absorbance is further improved. For example, when light enters from the first electrode 10, the anti-reflection layer 47 may be disposed on the first electrode 10 while when light enters from the second electrode 20, the anti-reflection layer 47 may be disposed under the second electrode 20.

The anti-reflection layer 47 may include, for example a material having a refractive index of about 1.6 to about 2.5 and may include for example at least one of a metal oxide, a metal sulfide, or an organic material having a refractive index within the ranges. The anti-reflection layer 47 may include, for example a metal oxide or chalcogen oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as a zinc sulfide; or an organic material such as an amine derivative, but is not limited thereto.

In the photoelectric devices 100 and 100', when light enters said photoelectric device 100 and/or 100' and thus enters the photoactive layer 30 thereof from (e.g., via) the first electrode 10 or the second electrode 20 and the photoactive layer 30 thus absorbs the light in a particular (or, alternatively, predetermined) wavelength region, excitons may be generated thereinside. The excitons are separated into holes and electrons in the photoactive layer 30, and the separated holes are transported to an anode that is one of the first electrode 10 or the second electrode 20 and the separated electrons are transported to the cathode that is the other of the first electrode 10 and the second electrode 20 so as to flow (e.g., induce, generate, etc.) a current.

The photoelectric devices 100 and 100' may be applied to (e.g., included in) a sensor such as an image sensor (e.g., CMOS image sensor), a photodetector, an optical sensor (infrared light sensor), a solar cell, etc., but example embodiments are not limited thereto.

The photoelectric devices 100 and 100' may be applied to (e.g., included in) a sensor. The sensor may be an organic CMOS sensor, for example, an organic CMOS infrared sensor or an organic CMOS image sensor.

In some example embodiments, the photoelectric device 100 may include the infrared absorber in any of the elements thereof, including, in addition to or alternative to the photoactive layer 30, one or more of the first electrode 10 or the second electrode 20. In some example embodiments, the photoelectric device 100' may include the infrared absorber in any of the elements thereof, including, in addition to or alternative to the photoactive layer 30 and/or one or more of the charge auxiliary layers 40/45, one or more of the first electrode 10 or the second electrode 20.

Hereinafter, an image sensor including the photoelectric device will be described with reference to the drawings.

Figure 3:
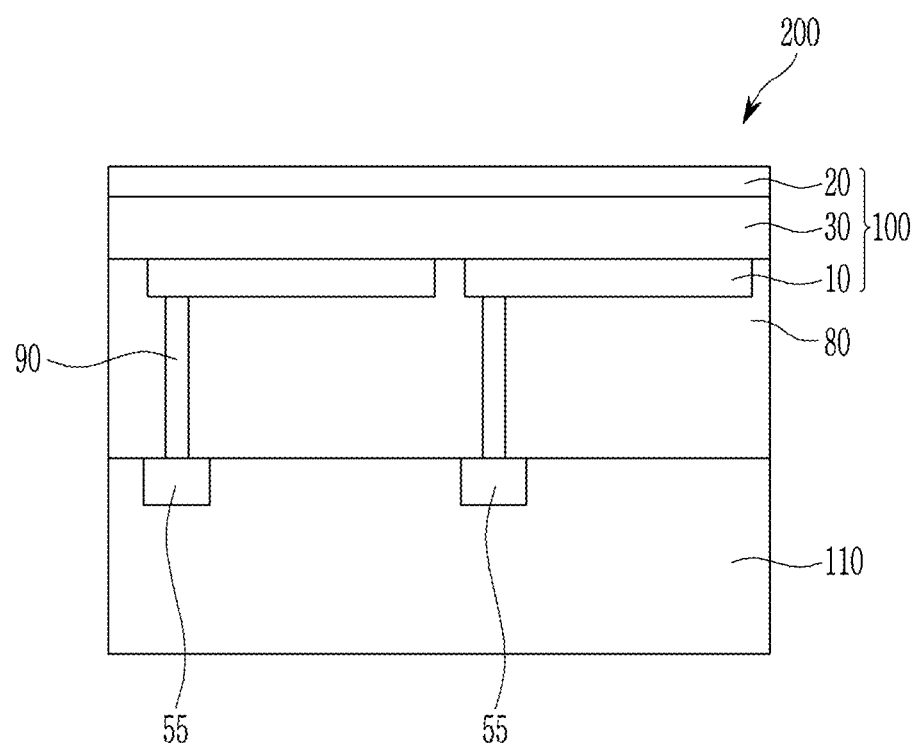
FIG. 3 is a cross-sectional view showing an image sensor according to some example embodiments.

FIG. 3 is a cross-sectional view showing an image sensor according to some example embodiments.

Referring to FIG. 3, the image sensor 200 according to some example embodiments includes a semiconductor substrate 110, an insulation layer 80, and a photoelectric device 100. FIG. 3 illustrates an image sensor 200 including the photoelectric device 100 of FIG. 1, but the image sensor 200 may also include the photoelectric device 100' of FIG. 2.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric device 100 and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal wire and pad. The insulation layer 80 may be made of an inorganic insulating material such as a silicon oxide and/or a silicon nitride, or a low dielectric constant (low K) material such as SiC, SiCOH, SiCO, and/or SiOF. The insulation layer 80 has a trench 90 exposing the charge storage 55. The trench 90 may be filled with fillers.

The aforementioned photoelectric device 100 is formed on the insulation layer 80. As described above, the photoelectric device 100 includes a first electrode 10, a photoactive layer 30, and a second electrode 20. Even though a structure in which the first electrode 10, the photoactive layer 30, and the second electrode 20 are sequentially stacked is shown as an example in the drawing, the present disclosure is not limited to this structure, and the second electrode 20, the photoactive layer 30, and the first electrode 10 may be arranged in this order.

The first electrode 10 and the second electrode 20 may both be transparent electrodes, and the photoactive layer 30 may be the same as described above with reference to FIGS. 1 and 2. The photoactive layer 30 may selectively absorb light in an infrared wavelength region. Incident light from the side of the second electrode 20 may be photoelectrically converted by mainly absorbing light in an infrared wavelength region in the photoactive layer 30. As noted above with reference to FIG. 1, the photoactive layer 30 may include the aforementioned infrared absorber and thus may have improved sensitivity to infrared light, such that the operational performance and/or efficiency of the image sensor 200 in absorbing and/or converting incident infrared light into electrical signals (e.g., photoelectric conversion performance and/or efficiency) may be improved.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

Figure 4:
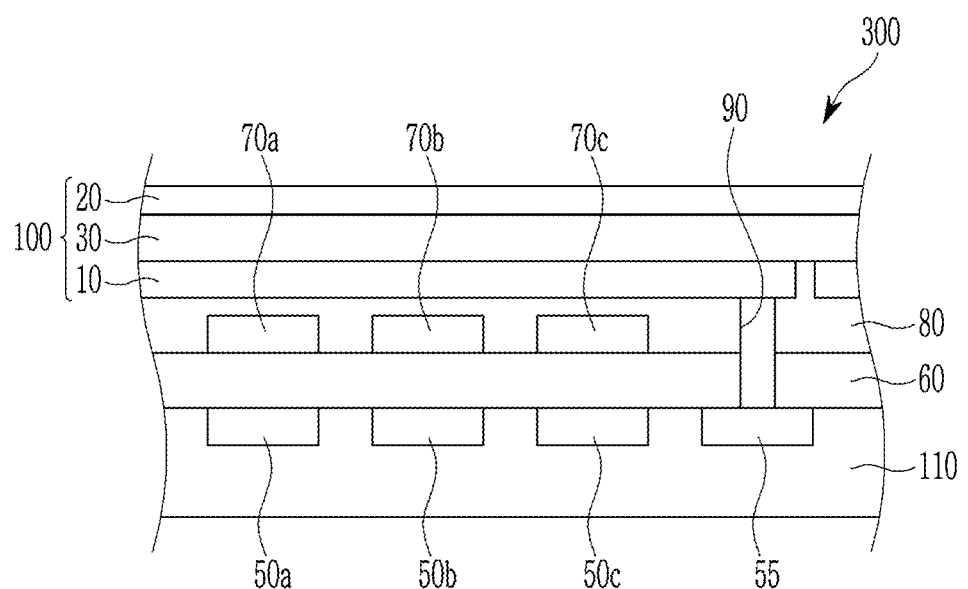
FIG. 4 is a cross-sectional view showing an image sensor according to some example embodiments.

FIG. 4 is a cross-sectional view showing an image sensor according to some example embodiments.

Referring to FIG. 4, an image sensor 300 according to some example embodiments includes a semiconductor substrate 110 integrated with photo-sensing devices (e.g., photodiodes, including silicon-based photodiodes) 50a, 50b, and 50c, a transmission transistor (not shown), and a charge storage 55, a lower insulation layer 60, color filter layers (also referred to herein as color filters) 70a, 70b, and 70c, an upper insulation layer 80, and a photoelectric device 100.

The semiconductor substrate 110 may be integrated with photo-sensing devices 50a, 50b, and 50c, a transmission transistor (not shown), and a charge storage 55. The photo-sensing devices 50a, 50b, and 50c may be photodiodes.

The photo-sensing devices 50a, 50b, and 50c, the transmission transistor, and/or the charge storage 55 may be integrated in each pixel. For example, the photo-sensing device 50a may be included in a red pixel, the photo-sensing device 50*b* may be included in a green pixel, and the photo-sensing device 50*c* may be included in a blue pixel.

The photo-sensing devices 50*a*, 50*b*, and 50*c* sense (e.g., selectively absorb and/or convert (into electrical signals, e.g., photoelectrically convert)) incident light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50*a* and 50*b*.

The lower insulation layer 60 is formed on the metal wire and the pad. The lower insulation layer 60 may include a same or different material composition as the insulation layer 80.

Color filters 70*a*, 70*b*, and 70*c* are formed on the lower insulation layer 60. The color filters 70*a*, 70*b*, and 70*c* includes a red filter 70*a* formed in a red pixel, a green filter 70*b* formed in a green pixel, and a blue filter 70*c* formed in a blue pixel.

The upper insulation layer 80 is formed on the color filters 70*a*, 70*b*, and 70*c*. The upper insulation layer 80 eliminates steps caused by the color filters 70*a*, 70*b*, and 70*c* and planarizes the surface.

The aforementioned photoelectric device 100 is formed on the upper insulation layer 80. As described above, the photoelectric device 100 includes a first electrode 10, a photoactive layer 30, and a second electrode 20. Even though a structure in which the first electrode 10, the photoactive layer 30, and the second electrode 20 are sequentially stacked is shown as an example in the drawing, the present disclosure is not limited to this structure, and the second electrode 20, the photoactive layer 30, and the first electrode 10 may be arranged in this order.

The first electrode 10 and the second electrode 20 may both be transparent electrodes, and the photoactive layer 30 is the same as described above. The photoactive layer 30 may selectively absorb light in a near-infrared/infrared wavelength region. As noted above with regard to photoelectric devices 100 and 100', any portion of the photoelectric device 100 (e.g., first electrode 10, second electrode 20, and/or photoactive layer 30) may include the aforementioned infrared absorber.

Incident light from the side of the second electrode 20 may be photoelectrically converted by mainly absorbing light in a near-infrared wavelength region in the photoactive layer 30. Light in the remaining wavelength region may pass through the first electrode 10 and the color filters 70*a*, 70*b*, and 70*c*, the light in a red wavelength region passing through the color filter 70*a* may be sensed by the photo-sensing device 50*a*, the light in a green wavelength region passing through the color filter 70*b* may be sensed by the photo-sensing device 50*b*, and the light in a blue wavelength region passing through the color filter 70*c* may be sensed by the photo-sensing device 50*c*.

As noted above with reference to FIG. 1, the photoactive layer 30 may include the aforementioned infrared absorber and thus may have improved sensitivity to near-infrared light, such that the operational performance and/or efficiency of the organic sensor 300 in absorbing and/or converting incident infrared light into electrical signals (e.g., photoelectric conversion performance and/or efficiency) may be improved.

Accordingly, where an image sensor 300 includes a photoelectric device 100 that includes the infrared absorber and is configured to selectively absorb and/or convert (into electrical signals, e.g., photoelectrically convert) light in a first infrared wavelength region, the image sensor may include an additional sensor that includes a plurality of photodiodes (e.g., photo-sensing devices 50*a*, 50*b*, 50*c*) at least partially embedded within the semiconductor substrate and configured to selectively absorb and/or convert (into electrical signals, e.g., photoelectrically convert) light in separate visible wavelength regions (e.g., red, green, and/or blue light).

Figure 5:
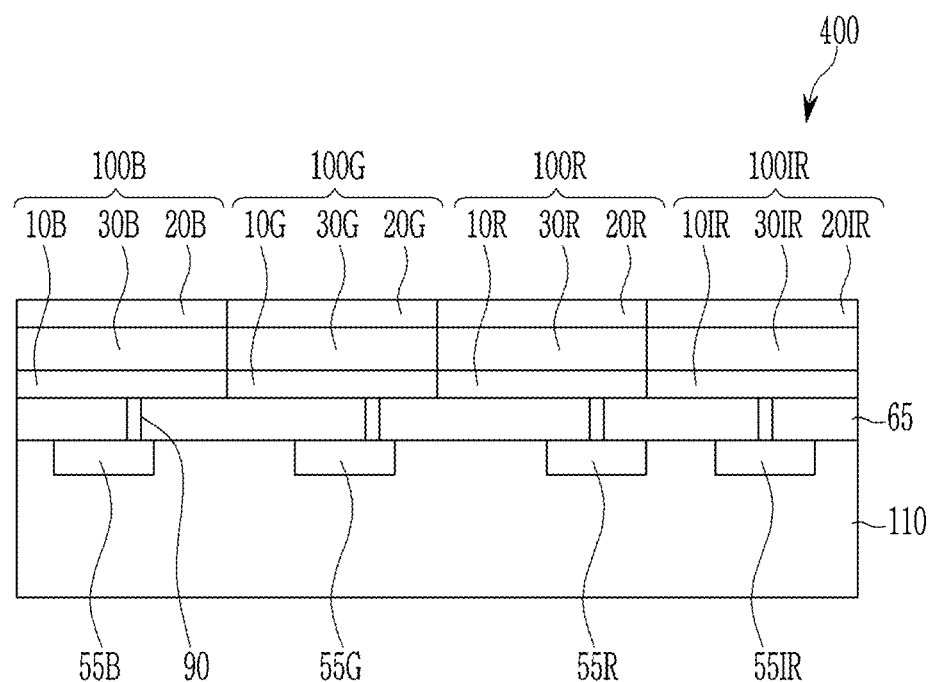
FIG. 5 is a cross-sectional view showing an image sensor according to some example embodiments.

FIG. 5 is a cross-sectional view showing an image sensor according to some example embodiments.

Referring to FIG. 5, an image sensor 400 according to some example embodiments includes a semiconductor substrate 110 integrated with an infrared light charge storage 55IR, a blue light charge storage 55B, a green light charge storage 55G, a red light charge storage 55R, and a transmission transistor (not shown), a lower insulation layer 65, a blue photo-sensing device 100B, a green photo-sensing device 100G, a red photo-sensing device 100R, and an infrared photo-sensing device 100IR.

The semiconductor substrate 110 may be a silicon substrate, and the infrared light charge storage 55IR, blue light charge storage 55B, the green light charge storage 55G, the red light charge storage 55R, and the transfer transistor (not shown) are integrated therein. The blue light charge storage 55B, the green light charge storage 55G, and the red light charge storage 55R may be integrated for each blue pixel, green pixel, and red pixel.

Charges absorbed in the infrared photo-sensing device 100IR, the blue photo-sensing device 100B, the green photo-sensing device 100G, and the red photo-sensing device 100R are collected in the infrared light charge storage 55IR, the blue light charge storage 55B, the green light charge storage 55G, and the red light charge storage 55R, which are electrically connected to each of the infrared photo-sensing device 100IR, the blue photo-sensing device 100B, the green photo-sensing device 100G, and the red photo-sensing device 100R.

A metal wire (not shown) and a pad (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The blue photo-sensing device 100B, the green photo-sensing device 100G, the red photo-sensing device 100R, and the infrared photo-sensing device 100IR are formed on the lower insulation layer 65. The blue photo-sensing device 100B may include a first electrode 10B, a second electrode 20B, and a photoactive layer 30B configured to selectively absorb light in a blue wavelength region, the green photo-sensing device 100G may include a first electrode 10G, a second electrode 20G, and a photoactive layer 30G configured to selectively absorb light in a green wavelength region, the red photo-sensing device 100R may include a first electrode 10R, a second electrode 20R, and a photoactive layer 30R configured to selectively absorb light in a red wavelength region, and the infrared photo-sensing device 100IR may include a first electrode 10IR, a second electrode 20IR, and a photoactive layer 30IR configured to selectively absorb light in an infrared light wavelength region.

The first electrodes 10B, 10G, 10R, and 10IR and the second electrodes 20B, 20G, 20R, and 20IR may be light-transmitting electrodes and may be made of, for example, a transparent conductor such as indium tin oxide (ITO), indium zinc oxide (IZO), zinc oxide (ZnO), tin oxide ($SnO_2$), aluminum tin oxide (AITO), and fluorine-doped tin oxide (FTO), or may be a metal thin film having a thin thickness of several nanometers to several tens of nanometers or a metal thin film having a thin thickness of several nanometers to several tens of nanometers doped with a metal oxide.

The photoactive layers 30B, 30G, 30R, and 30IR may include a p-type semiconductor material and an n-type semiconductor material. The photoactive layer 30B of the blue photo-sensing device 100B may include a p-type semiconductor material configured to selectively absorb light in a blue wavelength region and an n-type semiconductor material configured to selectively absorb light in a blue wavelength region, the photoactive layer 30G of the green photo-sensing device 100G may include a p-type semiconductor material configured to selectively absorb light in a green wavelength region and an n-type semiconductor material configured to selectively absorb light in a green wavelength region, the photoactive layer 30R of the red photo-sensing device 100R may include a p-type semiconductor material configured to selectively absorb light in a red wavelength region and an n-type semiconductor material configured to selectively absorb light in a red wavelength region, and the photoactive layer 30IR of the infrared photo-sensing device 100IR may include a p-type semiconductor material (the aforementioned infrared absorber) configured to selectively absorb light in an infrared region and an n-type semiconductor material configured to selectively absorb light in an infrared region. The infrared photo-sensing device 100IR may selectively absorb light in an infrared region of greater than or equal to about 800 nm and less than or equal to about 3000 nm without absorption of the visible light region.

Figure 6:
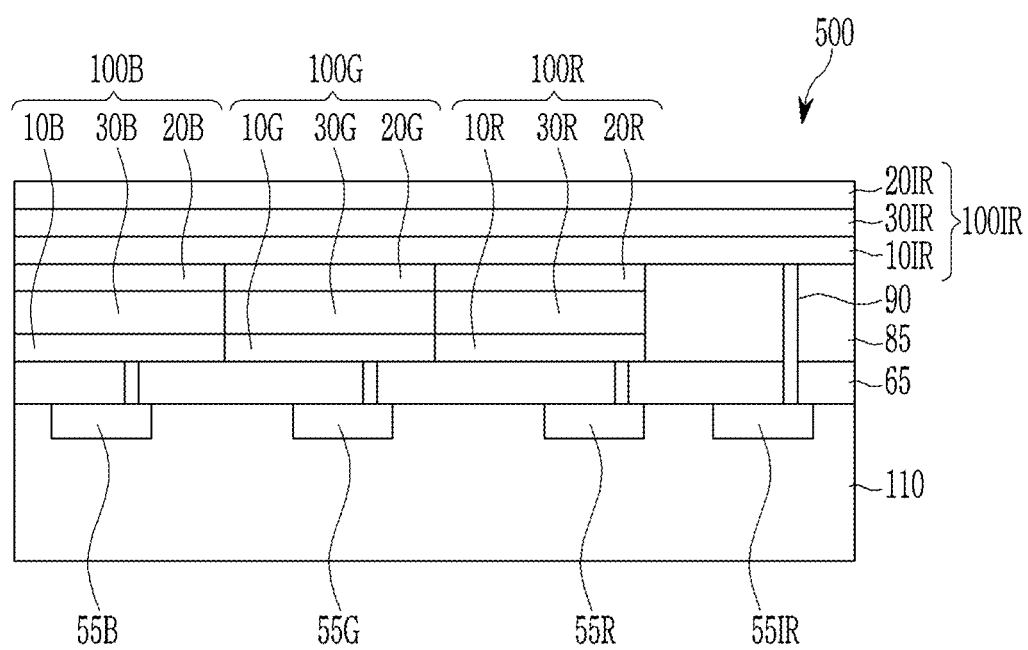
FIG. 6 is a cross-sectional view showing an image sensor according to some example embodiments.
Figure 7:
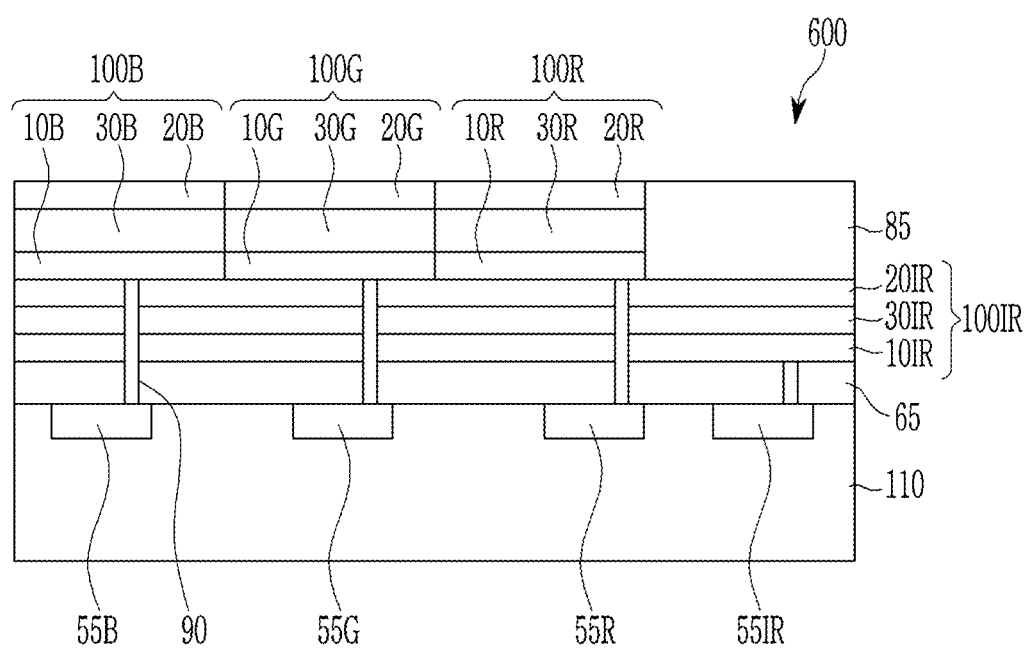
FIG. 7 is a cross-sectional view showing an image sensor according to some example embodiments.

FIG. 6 is a cross-sectional view showing an image sensor according to some example embodiments. FIG. 7 is a cross-sectional view showing an image sensor according to some example embodiments.

Referring to FIG. 6, an image sensor 500 may include an semiconductor substrate 110 integrated with an infrared light charge storage 55IR, a blue light charge storage 55B, a green light charge storage 55G, a red light charge storage 55R, and a transmission transistor (not shown), a lower insulation layer 65, a blue photo-sensing device 100B, a green photo-sensing device 100G, a red photo-sensing device 100R, and an infrared photo-sensing device 100IR. The infrared photo-sensing device 100IR is formed on is formed on the whole front surface of the blue photo-sensing device 100B, the green photo-sensing device 100G, and the red photo-sensing device 100R. The rest of the configuration is the same as that of the image sensor shown in FIG. 5, except the infrared photo-sensing device 100IR also extends on the upper insulation layer 85.

In the configuration of FIG. 6, the infrared photo-sensing device 100IR may be present on the lower insulation layer 65, and the blue photo-sensing device 100B, the green photo-sensing device 100G, the red photo-sensing device 100R may be disposed thereon. An image sensor 600 having such a configuration is shown in FIG. 7.

The infrared photo-sensing device 100IR may be configured to selectively absorb light in an infrared region of greater than or equal to about 800 nm and less than or equal to about 3000 nm, and have a large absorption area to improve efficiency.

The sensor according to some example embodiments may include a plurality of sensors having different functions. For example, at least one of the plurality of sensors having different functions may be a biometric sensor, and the biometric sensor may be for example an iris sensor, a depth sensor, a fingerprint sensor, a blood vessel distribution sensor, and the like, but is not limited thereto.

For example, one of the plurality of sensors having different functions may be an iris sensor and the other may be a depth sensor. The iris sensor identifies a person by using unique iris characteristics of every person and specifically, taking an image of an eye of a user within an appropriate distance, processing the image, and comparing it with his/her stored image. The depth sensor identifies a shape and a location of an object from its three-dimensional information by taking an image of the object within an appropriate distance with a user and processing the image. This depth sensor may be for example used as a face recognition sensor.

In some example embodiments, a plurality of sensors may include, for example a first infrared light sensor configured to sense light in an infrared region having a first wavelength ($\lambda_1$) in an infrared wavelength region and a second infrared light sensor configured to sense light in an infrared region having a second wavelength ($\lambda_2$) in an infrared wavelength region.

The first wavelength ($\lambda_1$) and the second wavelength ($\lambda_2$) may be for example different in a wavelength region of about 800 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

For example, one of the first wavelength ($\lambda_1$) or the second wavelength ($\lambda_2$) may belong to a wavelength region of about 780 nm to about 900 nm and the other of the first wavelength ($\lambda_1$) and the second wavelength ($\lambda_2$) may belong to a wavelength region of greater than about 900 nm and less than or equal to about 1000 nm.

For example, one of the first wavelength ($\lambda_1$) or the second wavelength ($\lambda_2$) may belong to a wavelength region of about 780 nm to about 840 nm and the other of the first wavelength ($\lambda_1$) and the second wavelength ($\lambda_2$) may belong to a wavelength region of about 910 nm to about 970 nm.

For example, one of the first wavelength ($\lambda_1$) or the second wavelength ($\lambda_2$) may belong to a wavelength region of about 800 nm to about 830 nm and the other of the first wavelength ($\lambda_1$) and the second wavelength ($\lambda_2$) may belong to a wavelength region of about 930 nm to about 950 nm.

For example, one of the first wavelength ($\lambda_1$) or the second wavelength ($\lambda_2$) may belong to a wavelength region of about 805 nm to about 815 nm and the other of the first wavelength ($\lambda_1$) and the second wavelength ($\lambda_2$) may belong to a wavelength region of about 935 nm to about 945 nm.

For example, one of the first wavelength ($\lambda_1$) or the second wavelength ($\lambda_2$) may about 810 nm and the other of the first wavelength ($\lambda_1$) and the second wavelength ($\lambda_2$) may be about 940 nm.

Figure 8:
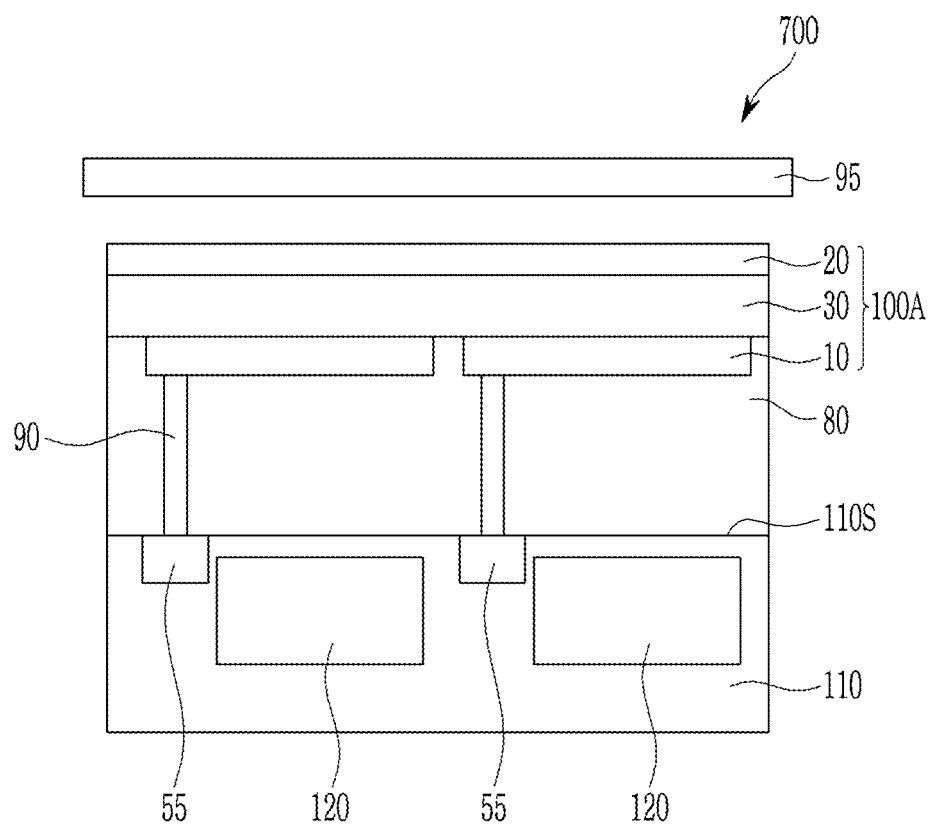
FIG. 8 is a cross-sectional view showing an image sensor according to some example embodiments.

FIG. 8 is a cross-sectional view illustrating an image sensor including a plurality of sensors according to some example embodiments.

The image sensor 700 according to some example embodiments includes a dual bandpass filter 95, a first infrared light sensor 100A, an insulation layer 80 (also referred to herein as an upper insulation layer), and a semiconductor substrate 110 integrated with a second infrared light sensor 120, such that the second infrared light sensor 120 is at least partially embedded within the semiconductor substrate 110. The first infrared light sensor 100A and the second infrared light sensor 120 are stacked, e.g., may overlap in a vertical direction that is perpendicular to the upper surface 110S of the semiconductor substrate 110.

The dual bandpass filter 95 may be disposed on a front side of the image sensor 400 and may selectively transmit infrared light including the first wavelength ($\lambda_1$) and infrared light including the second wavelength ($\lambda_2$) and may block and/or absorb other light. Herein, other light may include light in an ultraviolet (UV) and visible region.

The first infrared light sensor 100A includes a first electrode 10, a photoactive layer 30, and a second electrode 20. The first infrared light sensor 100A may be the same as the photoelectric device 100 according to some example embodiments, including the example embodiments described with reference to FIG. 1, but it will be understood that, in some example embodiments, the first infrared light sensor 100A may be the same as the photoelectric device 100' according to some example embodiments, including the example embodiments described with reference to FIG. 2.

The second infrared light sensor 120 may be integrated in the semiconductor substrate 110 (e.g., encompassed within a volume space defined by outer surfaces of the semiconductor substrate 110) and may be a photo-sensing device. The semiconductor substrate 110 may be for example a silicon substrate and may be integrated with the second infrared light sensor 120, the charge storage 55, and a transmission transistor (not shown).

The second infrared light sensor 120 may be a photodiode and may sense entered light, and sensed information is transferred by the transmission transistor. Herein, the light entered into the second infrared light sensor 120 is light that passes the dual bandpass filter 95 and the first infrared light sensor 100A and may be infrared light in a particular (or, alternatively, predetermined) region including the second wavelength ($\lambda_2$). All infrared light in a particular (or, alternatively, predetermined) region including the first wavelength ($\lambda_1$) may be absorbed by the photoactive layer 30 and may not reach the second infrared light sensor 120. In this case, a separate filter for wavelength selectivity with respect to the light entered into the second infrared light sensor 120 is not separately needed. However, for the time when all infrared light in a particular (or, alternatively, predetermined) region including the first wavelength ($\lambda_1$) is not absorbed by the photoactive layer 30, a filter between the first infrared light sensor 100A and the second infrared light sensor 120 may be further disposed.

Accordingly, in the image sensor 700, the first infrared light sensor 100A may be understood to include a photoelectric device (e.g., photoelectric device 100 and/or 200) configured to sense (e.g., selectively absorb and/or convert (into electrical signals, e.g., photoelectrically convert)) light in a first infrared wavelength region of incident light (e.g., a first infrared wavelength region including the first wavelength ($\lambda_1$)), and the second infrared light sensor 120 may be understood to be an additional sensor configured to selectively absorb and/or convert (into electrical signals, e.g., photoelectrically convert) light in a separate wavelength region of incident light (e.g., a second infrared wavelength region that is different from the first near-infrared wavelength region and includes the second wavelength ($\lambda_2$) and excludes the first wavelength ($\lambda_1$)).

As noted above with reference to FIG. 1, the photoactive layer 30, or any portion of the photoelectric device 100 and/or 100', may include the aforementioned infrared absorber and thus may have improved sensitivity to and/or absorbance of infrared light, such that the operational performance and/or efficiency of the image sensor 700 in absorbing and/or photoelectrically converting incident infrared light into electrical signals (e.g., photoelectric conversion performance and/or efficiency) may be improved. In some example embodiments, the second infrared light sensor 120 may include the aforementioned infrared absorber and thus may have improved sensitivity to and/or absorbance of infrared light, such that the operational performance and/or efficiency of the image sensor 700 in absorbing and/or converting incident infrared light into electrical signals (e.g., photoelectric conversion performance and/or efficiency) may be improved.

The sensor according to some example embodiments may include two infrared light sensors respectively performing separately functions and thus may work as a combination sensor. In addition, two sensors performing separately functions are stacked in each pixel, and thus the number of pixel performing functioning of each sensor is twice increased while maintaining a size and resultantly, sensitivity may be much improved.

The aforementioned sensor may be applied to various electronic devices, for example and the electronic devices may include for example a camera, a camcorder, a mobile phone internally having them, a display device, a security device, or a medical device, but are not limited thereto.

Figure 9:
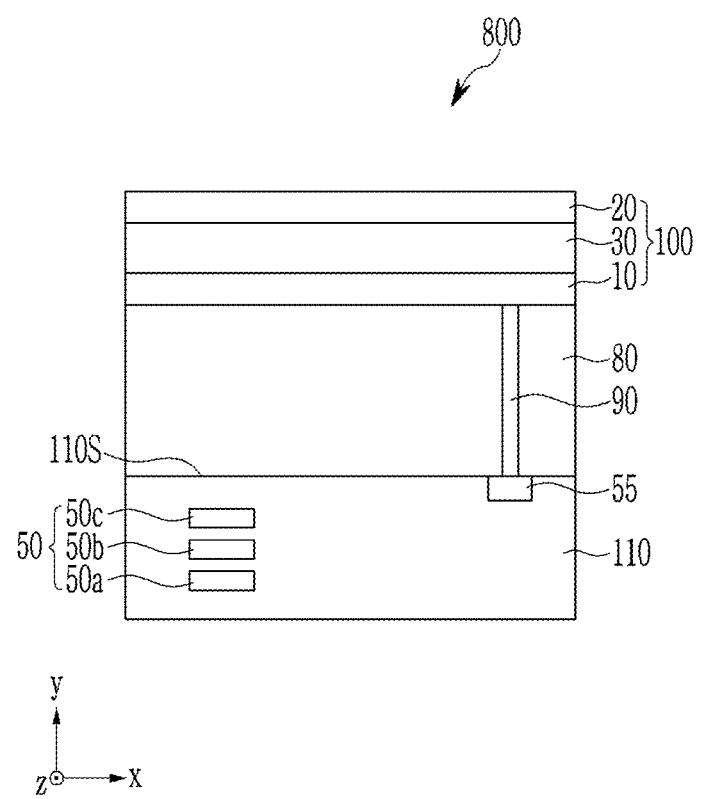
FIG. 9 is a cross-sectional view showing an image sensor according to some example embodiments.

FIG. 9 is a cross-sectional view showing an image sensor according to some example embodiments.

Referring to FIG. 9, the image sensor 800 according to some example embodiments includes the visible light sensor 50, and the photoelectric device 100 like that of some example embodiments. As shown in FIG. 9, the visible light sensor 50 includes a red photo-sensing device 50a, a green photo-sensing device 50b, and a blue photo-sensing device 50c integrated in (e.g., at least partially embedded within) the semiconductor substrate 110, wherein the red photo-sensing device 50a, the green photo-sensing device 50b, and the blue photo-sensing device 50c may be photodiodes and may be configured to selectively absorb light in separate visible wavelength regions.

In the image sensor 800 according to some example embodiments, the red photo-sensing device 50a, the green photo-sensing device 50b, and the blue photo-sensing device 50c integrated in the semiconductor substrate 110 are stacked (e.g., overlap with each other) in a vertical direction (e.g., the Y direction, extending perpendicular to the upper surface 110S of the semiconductor substrate 110) and overlap with the photoelectric device 100 in the vertical direction. The red photo-sensing device 50a, the green photo-sensing device 50b, and the blue photo-sensing device 50c may be configured to selectively absorb and/or convert (into electrical signals, e.g., photoelectrically convert) light in each wavelength region depending on a stacking depth from the upper surface 110S and thus sense it. In other words, the red photo-sensing device 50a configured to selectively absorb and/or convert (into electrical signals, e.g., photoelectrically convert) red light in a long wavelength region is disposed deeper from the upper surface 110S of the semiconductor substrate 110 than the blue photo-sensing device 50c configured to selectively absorb and/or convert (into electrical signals, e.g., photoelectrically convert) blue light in a short wavelength region, and the green photo-sensing device 50b configured to selectively absorb and/or convert (into electrical signals, e.g., photoelectrically convert) green light in a medium wavelength region is disposed deeper from the upper surface 110S of the semiconductor substrate 110 than the blue photo-sensing device 50c and closer to the upper surface 110S of the semiconductor substrate 110 than the red photo-sensing device 50a. In this way, the color filters 70a, 70b, and 70c may be omitted by separating absorption wavelengths depending on the stacking depth.

Figure 10:
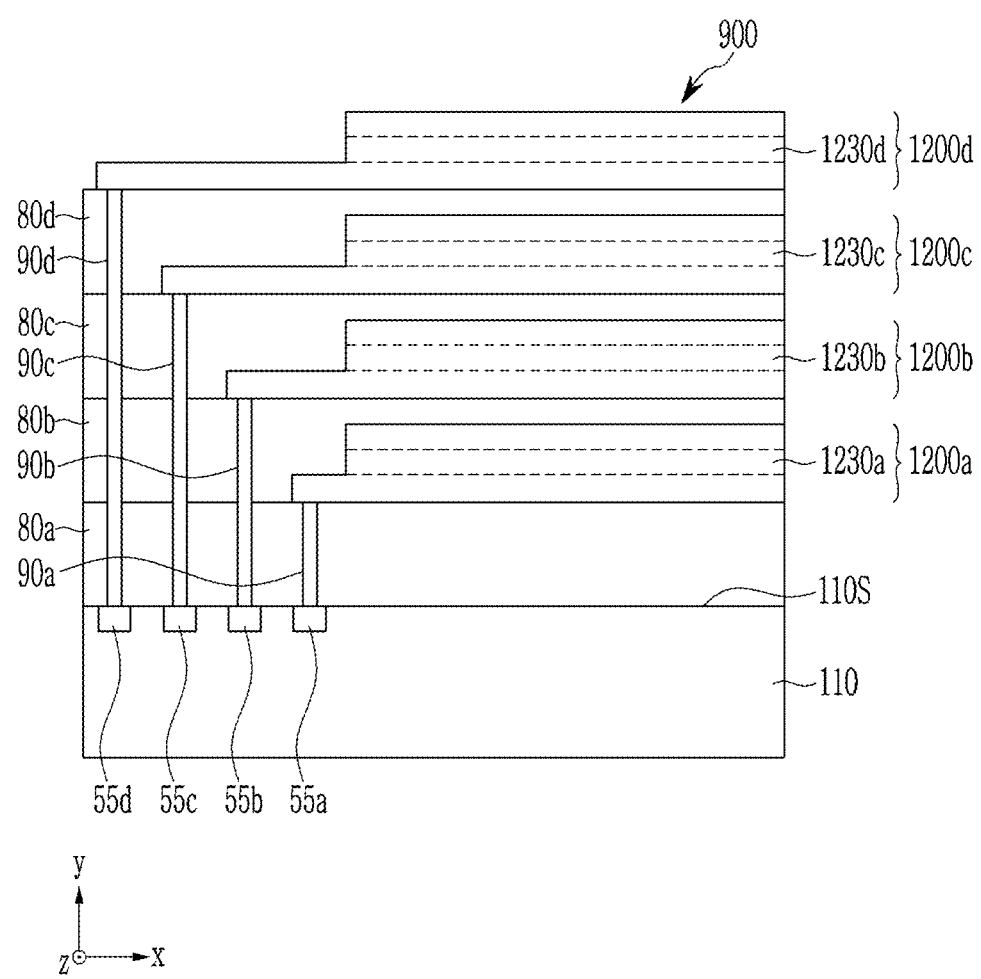
FIG. 10 is a cross-sectional view showing an image sensor according to some example embodiments.

FIG. 10 is a cross-sectional view showing an image sensor according to some example embodiments.

Referring to FIG. 10, the image sensor 900 according to some example embodiments includes a first photoelectric device (e.g., infrared/near infrared photoelectric device 1200d) configured to selectively absorb and/or convert (into electrical signals, e.g., photoelectrically convert) light in an infrared/near infrared wavelength spectrum of incident light (e.g., a first infrared wavelength region), and at least one additional photoelectric device (e.g., 1200a to 1200c) vertically stacked (e.g., in the vertical direction extending perpendicular to the upper surface 110S of the semiconductor substrate 110) between the first photoelectric device and a semiconductor substrate (e.g., 110), each separate photoelectric device of the at least one additional photoelectric device (e.g., 1200a to 1200c) including a separate photoelectric conversion layer and configured to selectively absorb and/or convert (into electrical signals, e.g., photoelectrically convert) a separate (e.g., respective) wavelength region of incident light that is different from the first infrared wavelength region and which may be a separate visible and/or non-visible wavelength region. For example, as shown in FIG. 10, the image sensor 900 may include additional photoelectric devices 1200a to 1200c that include a red photoelectric device 1200a configured to selectively absorb and/or convert (into electrical signals, e.g., photoelectrically convert) light in a red wavelength spectrum of incident light, a green photoelectric device 1200b configured to selectively absorb and/or convert (into electrical signals) light in a green wavelength spectrum of incident light, and a blue photoelectric device 1200c configured to selectively absorb and/or convert (into electrical signals) light in a blue wavelength spectrum of incident light, and they are stacked in the vertical direction that extends perpendicular to the upper surface 110S of the semiconductor substrate 110 (e.g., Y direction).

Accordingly, it will be understood that, as shown in FIG. 10, the image sensor 900 may include a plurality of photoelectric devices 1200a-1200d that are stacked vertically on the semiconductor substrate 110, such that the plurality of photoelectric devices 1200a-1200d overlap each other in a direction extending perpendicular to an upper surface 110S of the semiconductor substrate 110. While the image sensor 900 includes multiple additional photoelectric devices 1200a to 1200c in addition to the first photoelectric device (e.g., fourth photoelectric device 1200d) configured to selectively absorb and/or convert light in the first near-infrared wavelength region, it will be understood that in some example embodiments the image sensor 900 may be limited to a single additional photoelectric device (e.g., any of 1200a to 1200c) between the photoelectric device 1200d and the semiconductor substrate 110.

The image sensor 900 according to some example embodiments includes a semiconductor substrate 110, a lower insulation layer 80a, an intermediate insulation layer 80b, another intermediate insulation layer 80c, an upper insulation layer 80d, a first photoelectric device 1200a, a second photoelectric device 1200b, a third photoelectric device 1200c, and a fourth photoelectric device 1200d. Each given photoelectric device of the first to fourth photoelectric devices 1200a to 1200d may include first and second electrodes and a photoactive layer (e.g., 1230a to 1230d, respectively) between the respective first and second electrodes of the given photoelectric device. Each given photoelectric device of the first to fourth photoelectric devices 1200a to 1200d may have a same structure and/or material composition as any of the photoelectric devices of FIGS. 1-9 according to any of the example embodiments.

In some example embodiments, the fourth photoelectric device 1200d may be referred to as a first photoelectric device configured to selectively absorb and/or convert (into electrical signals, e.g., photoelectrically convert) light in a first near-infrared wavelength region, and the first to third photoelectric devices 1200a to 1200c may be collectively referred to as at least one additional photoelectric device configured to selectively absorb and/or convert (into electrical signals, e.g., photoelectrically convert) light in one or more separate wavelength regions different from the first near-infrared wavelength region. As shown, the first to fourth photoelectric devices 1200a to 1200d are stacked vertically on the semiconductor substrate 110, such that the first to fourth photoelectric devices 1200a to 1200d overlap each other in a direction extending perpendicular to an upper surface 110S of the semiconductor substrate 110.

The semiconductor substrate 110 may be a silicon substrate, and is integrated with the transmission transistor (not shown) and charge storages.

The first through third photoelectric devices 1200a to 1200c may have a same structure as any of the photoelectric devices according to any of the example embodiments herein, including without limitation the photo-sensing devices 100B, 100G, and 100R shown in any of FIGS. 5-7, except each separate photoelectric device 1200a to 1200c may be configured to photoelectrically convert a separate wavelength region of visible and/or non-visible (e.g., near-infrared) light, and the respective photoelectric conversion layers 1230a to 1230c of the first to third photoelectric devices 1200a to 1200c may have a same structure as any of the photoelectric devices according to any of the example embodiments herein, including without limitation the photoelectric device 100 of FIGS. 1 and 3-4, the photoelectric device 100' of FIG. 2, the photo-sensing devices 100B, 100G, 100R, and/or 100IR shown in any of FIGS. 5-7 and/or the first infrared light sensor 100A shown in FIG. 8. The photoelectric conversion layer 1230d may have a same structure and/or composition as the photoactive layer according to any of the example embodiments as described herein, including the photoactive layer 30, 30B, 30G, 30R, and/or 30IR as described herein so as to be configured to selectively absorb and/or convert (into electrical signals, e.g., photoelectrically convert) different visible and/or non-visible wavelength regions of light, and may include the infrared absorber.

The fourth photoelectric device 1200d may have a same structure as any of the photoelectric devices according to any of the example embodiments herein, including without limitation the photoelectric device 100 of FIGS. 1 and 3-4, the photoelectric device 100' of FIG. 2, the additional photoelectric devices 100B, 100G, 100R, and/or 100IR shown in any of FIGS. 5-7 and/or the first infrared light sensor 100A shown in FIG. 8. The photoelectric conversion layer 1230*d* may have a same structure and/or composition as the photoactive layer according to any of the example embodiments as described herein, including the photoactive layer 30, 30B, 30G, 30R, and/or 30IR as described herein so as to be configured to selectively absorb and/or convert (into electrical signals, e.g., photoelectrically convert) different visible and/or non-visible wavelength regions of light, and may include the infrared absorber.

The first photoelectric device 1200*a* is formed on the lower insulation layer 80*a*. The first photoelectric device 1200*a* includes a photoelectric conversion layer 1230*a*. The first photoelectric device 1200*a* may be any one of the photoelectric devices described herein according to any of the example embodiments. The photoelectric conversion layer 1230*a* may selectively absorb and/or convert (into electrical signals, e.g., photoelectrically convert) light in one of infrared, red, blue, and green wavelength spectra of incident light. For example, the first photoelectric device 1200*a* may be a blue photoelectric device.

An intermediate insulation layer 80*b* is formed on the first photoelectric device 1200*a*.

The second photoelectric device 1200*b* is formed on the intermediate insulation layer 80*b*. The second photoelectric device 1200*b* includes a photoelectric conversion layer 1230*b*. The second photoelectric device 1200*b* may be any one of the photoelectric devices described herein according to any of the example embodiments. The photoelectric conversion layer 1230*b* may selectively absorb and/or convert (into electrical signals, e.g., photoelectrically convert) light in one of infrared, red, blue, or green wavelength spectra of incident light. For example, the second photoelectric device 1200*b* may be a green photoelectric device.

Another intermediate insulation layer 80*c* is formed on the second photoelectric device 1200*b*.

The third photoelectric device 1200*c* is formed on the intermediate insulation layer 80*c*. The third photoelectric device 1200*c* includes a photoelectric conversion layer 1230*c*. The third photoelectric device 1200*c* any one of the photoelectric devices described herein according to any of the example embodiments. The photoelectric conversion layer 1230*c* may selectively absorb and/or convert (into electrical signals, e.g., photoelectrically convert) light in one of infrared, red, blue, or green wavelength spectra of incident light. For example, the third photoelectric device 1200*c* may be a red photoelectric device.

The upper insulation layer 80*d* is formed on the third photoelectric device 1200*c*.

The lower insulation layer 80*a*, the intermediate insulation layers 80*b* and 80*c*, and the upper insulation layer 80*d* have a plurality of through holes, or trenches 90*a*, 90*b*, 90*c*, and 90*d* exposing the charge storages 55*a*, 55*b*, 55*c*, and 55*d*, respectively, and said trenches may be partly or completely filled with a filler material (e.g., fillers).

The fourth photoelectric device 1200*d* is formed on the upper insulation layer 80*d*. The fourth photoelectric device 1200*d* includes a photoelectric conversion layer 1230*d*. The fourth photoelectric device 1200*d* may be any one of the photoelectric devices described herein according to any of the example embodiments. The photoelectric conversion layer 1230*d* may selectively absorb and/or convert (into electrical signals, e.g., photoelectrically convert) light in one of infrared, red, blue, or green wavelength spectra of light. For example, the fourth photoelectric device 1200*d* may be an infrared/near infrared photoelectric device that may include the infrared absorber.

In the drawing, the first photoelectric device 1200*a*, the second photoelectric device 1200*b*, the third photoelectric device 1200*c*, and the fourth photoelectric device 1200*d* are sequentially stacked, but the present disclosure is not limited thereto, and they may be stacked in various orders.

As described above, the first photoelectric device 1200*a*, the second photoelectric device 1200*b*, the third photoelectric device 1200*c*, and the fourth photoelectric device 1200*d* have a stack structure, and thus the size of an image sensor may be reduced to realize a down-sized image sensor.

Figure 11:
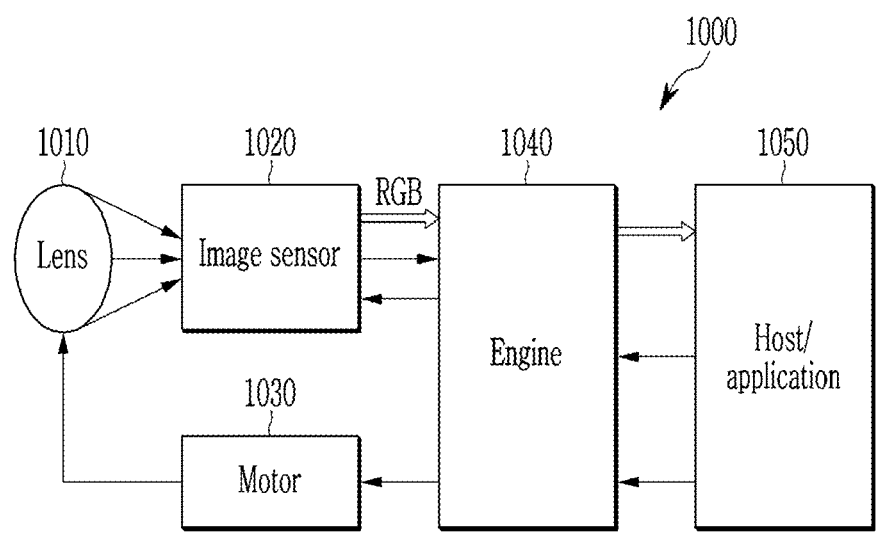
FIG. 11 is a block diagram of a digital camera including an image sensor some example embodiments.

FIG. 11 is a block diagram of a digital camera including an image sensor according to some example embodiments.

Referring to FIG. 11, a digital camera 1000 includes a lens 1010, an image sensor 1020, a motor 1030, and an engine 1040. The image sensor 1020 may be one of image sensors according to any of the example embodiments, including the example embodiments shown in FIGS. 3 to 10.

The lens 1010 concentrates incident light on the image sensor 1020. The image sensor 1020 generates RGB data for received light through the lens 1010.

In some example embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 12:
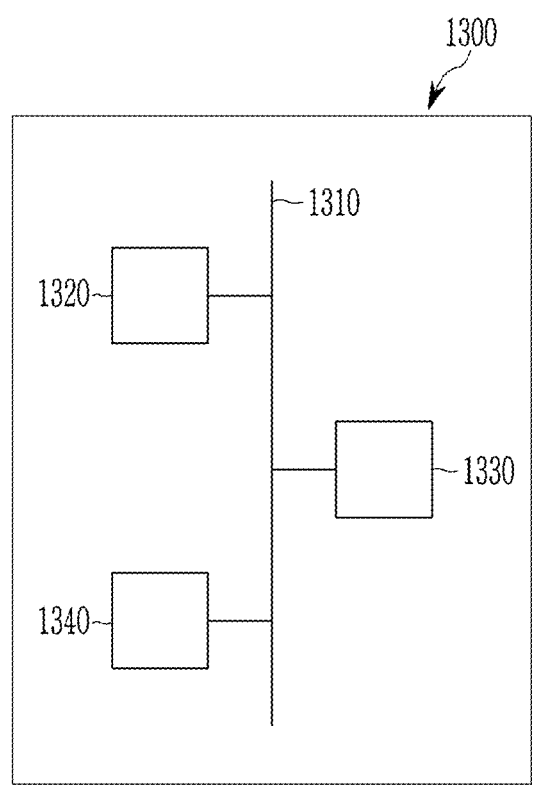
FIG. 12 is a schematic diagram showing an electronic device according to some embodiments.

FIG. 12 is a schematic diagram showing an electronic device 1300 according to some embodiments. Referring to FIG. 12, an electronic device 1300 may include a processor 1320, a memory 1330, and an image sensor 1340 that are electrically coupled together via a bus 1310. The image sensor 1340 may be an image sensor, photoelectric device, camera, or the like according to any of the example embodiments, including the example embodiments shown in FIGS. 3 to 11. The memory 1330, which may be a non-transitory computer readable medium and may store a program of instructions. The memory 1330 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1320 may execute the stored program of instructions to perform one or more functions. For example, the processor 1320 may be configured to process electrical signals generated by the image sensor 1340. The processor 1320 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1320 may be configured to generate an output (e.g., an image to be displayed on a display interface) based on such processing.

One or more of the processor 1320, memory 1330, motor 1030, engine 1040, or host/application 1050 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the processor 1320, memory 1330, motor 1030, engine 1040, or host/application 1050, or the like according to any of the example embodiments as described herein.

Hereinafter, some example embodiments are illustrated in more detail with reference to examples. However, the present scope of the example embodiments is not limited to these examples.

SYNTHESIS EXAMPLES

Synthesis Example 1: Synthesis of Compound Represented by Chemical Formula 1-1

[Chemical Formula 1-1]

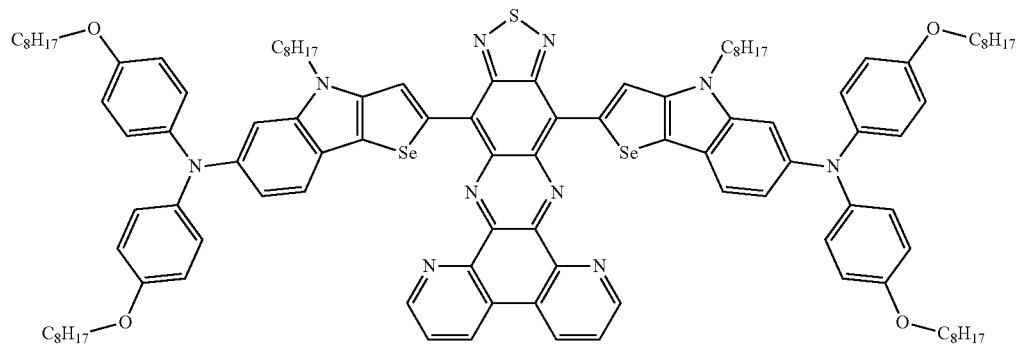

[Reaction Scheme 1-1]

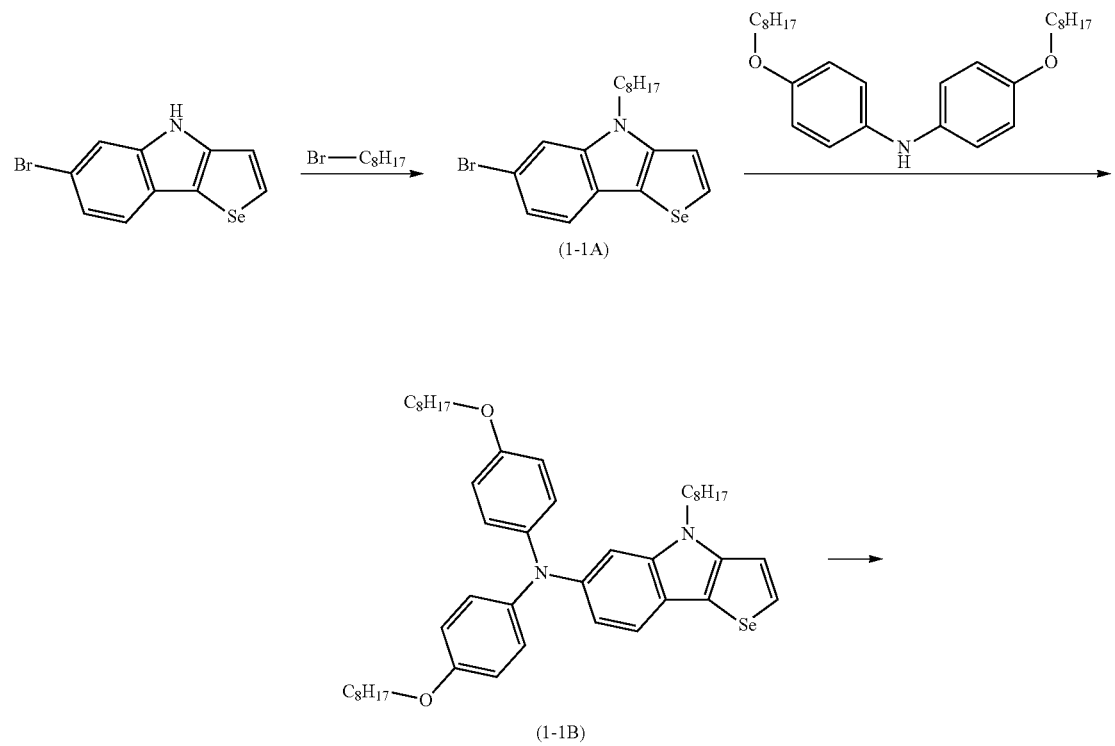

-continued

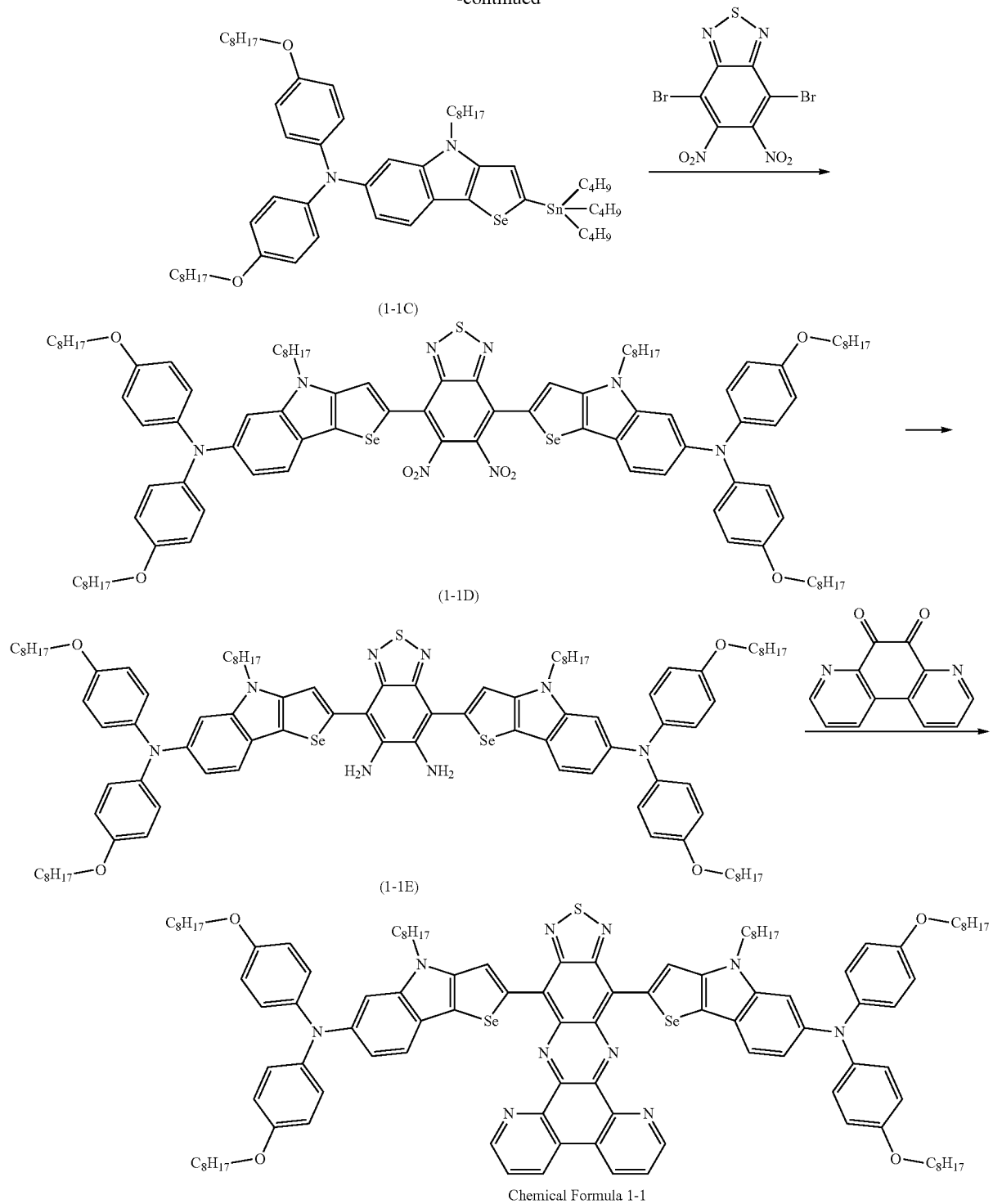

(1-1C)

(1-1D)

(1-1E)

Chemical Formula 1-1 i) First Step: Synthesis of Compound (1-1A)

6-bromo-4H-selenopheno[3,2-b]indole (3.0 g, 10.0 mmol) is dissolved in 50 ml of DMF at room temperature (24° C. to 25° C., the same as below). NaH (60% in mineral oil, 1.2 g, 30.1 mmol) is added thereto and then, stirred for 2 hours. 1-bromooctane (9.69 g, 50.1 mmol) is added thereto and then, stirred again for 2 hours. The obtained product is separated and purified through silica gel column chromatography (EA:n-Hex=1:30 v/v) to obtain 4.1 g (Yield: about 99%) of Compound (1-1A).

ii) Second Step: Synthesis of Compound (1-1B)

Compound (1-1A) (2.9 g, 7.1 mmol) and bis(4-(octyloxy)phenyl)amine (3 g, 7.1 mmol) are heated and refluxed in 100 ml of anhydrous toluene under Pd(dba)$_2$ (bis(dibenzylideneacetone)palladium (0), 5 mol %), P(tBu)$_3$ (tri-tert-butylphosphine, 5 mol %), and NaOtBu (sodium tert-butoxide, 0.81 g, 8.5 mmol) for 12 hours. The obtained product is separated and purified through silica gel column chromatography (EA:n-Hex=1:20 v/v) to obtain 4.1 g (Yield: 77%) of Compound (1-1B).

NMR (300 MHz, CD$_2$Cl$_2$): 7.86 (d, 1H), 7.48 (d, 1H), 7.34 (d, 1H), 7.01-6.98 (m, 5H), 6.79-6.76 (m, 5H), 4.81 (t, 2H), 3.90 (t, 4H), 1.76-1.72 (m, 6H), 1.51-1.20 (m, 30H), 0.87-0.82 (m, 9H).

LC-MS: 757.35 m/z confirmation of molecular weight iii) Third Step: Synthesis of Compound (1-1C)

Compound (1-1B) (4.1 g, 5.4 mmol) is dissolved in anhydrous tetrahydrofuran (THF) and then, stirred at −78° C. 2.5 M n-BuLi (in n-Hex, 2.17 ml, 5.4 mmol) is slowly added thereto and then, stirred for 3 hours, and tributyltin chloride (1.77 g, 5.4 mmol) is added thereto and then, heated up to room temperature. The obtained product is extracted with chloroform to obtain 5.6 g (Yield: about 99%) of Compound (1-1C). Compound (1-1C) is used for the fourth step reaction without additional purification.

LC-MS: 1045.46 m/z confirmation of molecular weight.

iv) Fourth Step: Synthesis of Compound (1-1D)

4,8-dibromobenzo[1,2-c;4,5-c']bis[1,2,5]thiadiazole (0.41 g, 1.1 mmol), Compound (1-1C) (2.25 g, 2.2 mmol), and tetrakis(triphenylphosphine)palladium (0) (5 mol %) are dissolved in 50 ml of toluene and then, stirred at 110° C. for 18 hours. When a reaction is completed, after evaporating and removing the toluene, the residue is separated and purified through silica gel column chromatography (methylene chloride (MC):n-hexane (n-Hex)=1:1 in a volume ratio) to obtain 0.54 g (Yield: 30%) of Compound (1-1D).

LC-MS: 1734.64 m/z confirmation of molecular weight.

v) Fifth Step: Synthesis of Compound (1-1E)

Compound (1-1D) (0.2 g, 0.12 mmol) and ammonium formate (0.73 g, 11.5 mmol) are dissolved in ethanol/ethylacetate (EA) (10 ml/10 ml), and Pd/C (10 wt %, 0.06 g, 0.06 mmol) is added thereto and then, stirred at 70° C. When a reaction is completed, the resultant is separated and purified through silica gel column chromatography (MC:n-Hex=1:1 in a volume ratio) to obtain 0.1 g (Yield: 52%) of Compound (1-1E).

LC-MS: 1674.20 m/z confirmation of molecular weight.

vi) Sixth Step: Synthesis of Compound Represented by Chemical Formula 1-1

Compound (1-1E) (0.1 g, 0.06 mmol) and 4,7-phenanthroline-5,6-dione (0.015 g, 0.07 mmol) are dissolved in chloroform/acetic acid (5/1 ml) and then, stirred at room temperature for 12 hours. When a reaction is completed, the resultant is precipitated in methanol to obtain 0.07 g (Yield: 63%) of a compound represented by Chemical Formula 1-1.

MALDI-TOF-MS: 1848.73 m/z confirmation of molecular weight.

Synthesis Example 2: Synthesis of Compound Represented by Chemical Formula 1-2

[Chemical Formula 1-2]

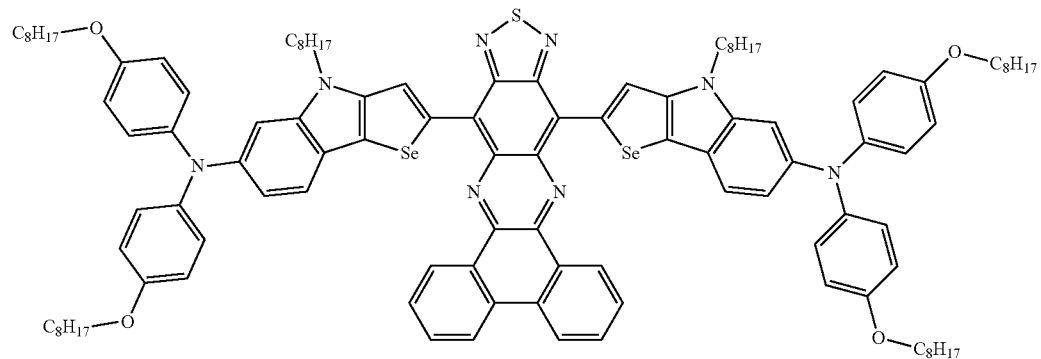

[Reaction Scheme 1-2]

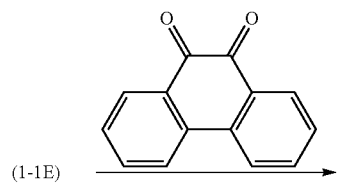

-continued

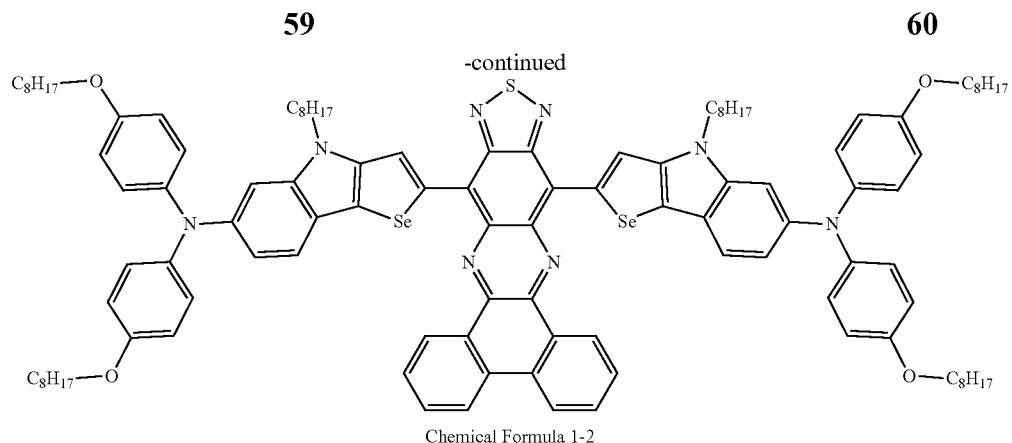

Chemical Formula 1-2 i) First Step: Synthesis of Compound Represented by Chemical Formula 1-2

Compound (1-1E) of Synthesis Example 1 (0.1 g, 0.06 mmol) and phenanthrene-9,10-dione (0.015 g, 0.07 mmol) are dissolved in chloroform/acetic acid (5/1 ml) and then, stirred at room temperature for 12 hours. When a reaction is completed, the resultant is precipitated in methanol to obtain 0.08 g (Yield: 73%) of a compound represented by Chemical Formula 1-2.

MALDI-TOF-MS: 1846.76 m/z confirmation of molecular weight.

Synthesis Example 3: Synthesis of Compound Represented by Chemical Formula 1-3

[Chemical Formula 1-3]

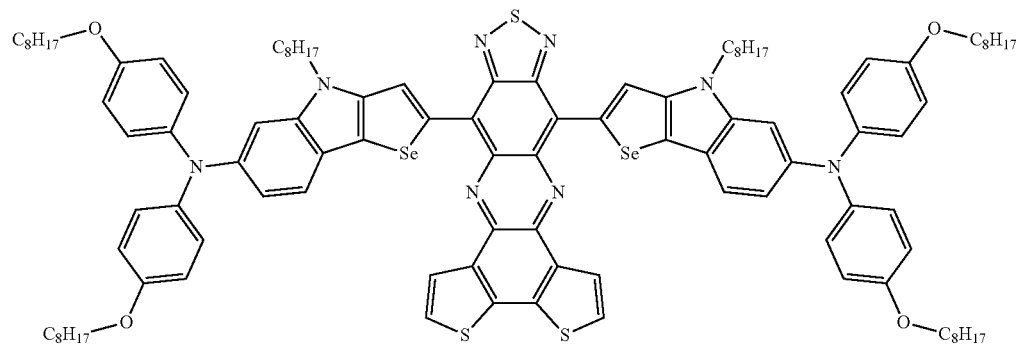

[Reaction Scheme 1-3]

(1-1E)

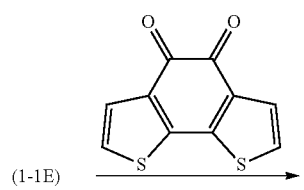

→

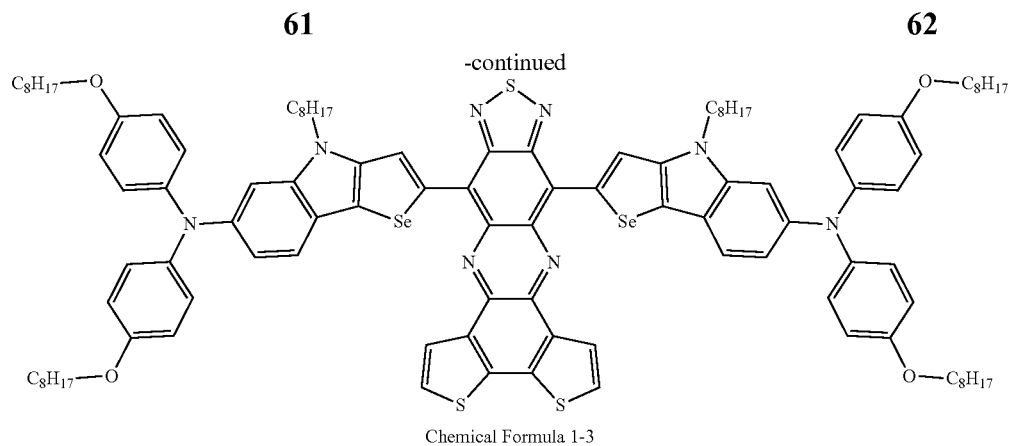

Chemical Formula 1-3 i) First Step: Synthesis of Compound Represented by Chemical Formula 1-3

Compound (1-1E) of Synthesis Example 1 (0.1 g, 0.06 mmol) and benzo[1,2-b:6,5-b']dithiophene-4,5-dione (0.015 g, 0.07 mmol) are dissolved in chloroform/acetic acid (5 ml/1 ml) and then, stirred at room temperature for 12 hours. When a reaction is completed, the resultant is precipitated in methanol to obtain 0.04 g (Yield: 36%) of a compound represented by Chemical Formula 1-3.

MALDI-TOF-MS: 1858.75 m/z confirmation of molecular weight.

Synthesis Example 4: Synthesis of Compound Represented by Chemical Formula 1-4

[Chemical Formula 1-4]

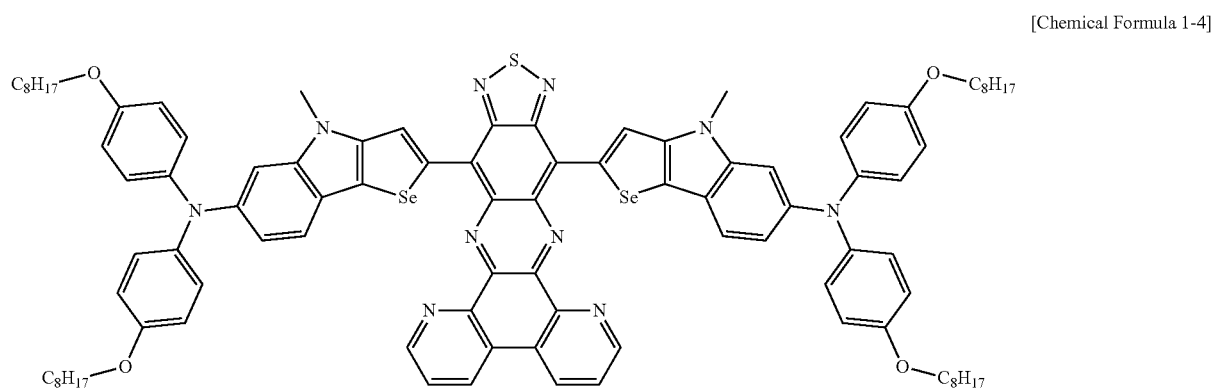

[Reaction Scheme 1-4]

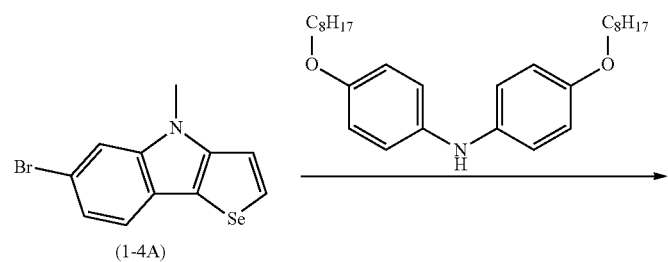

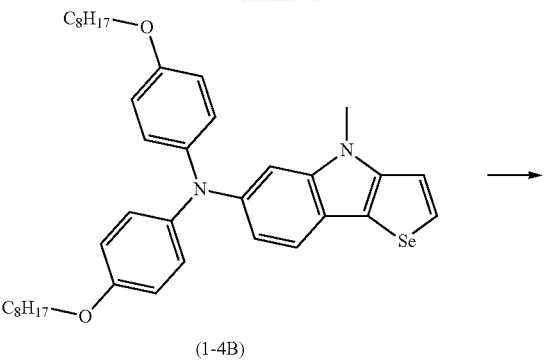
(1-4B)
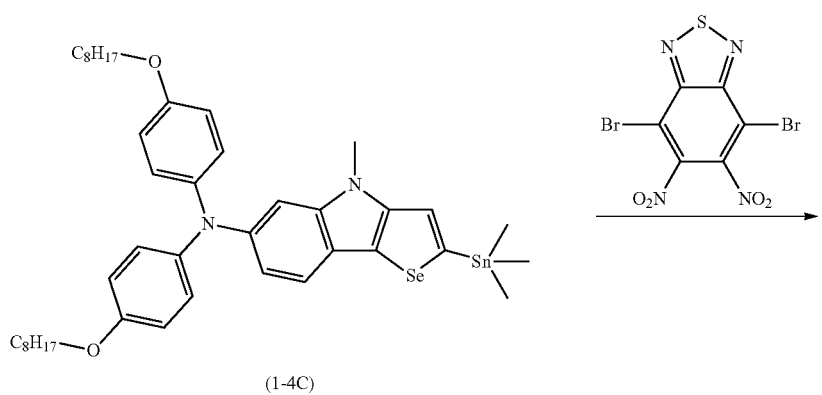
(1-4C)
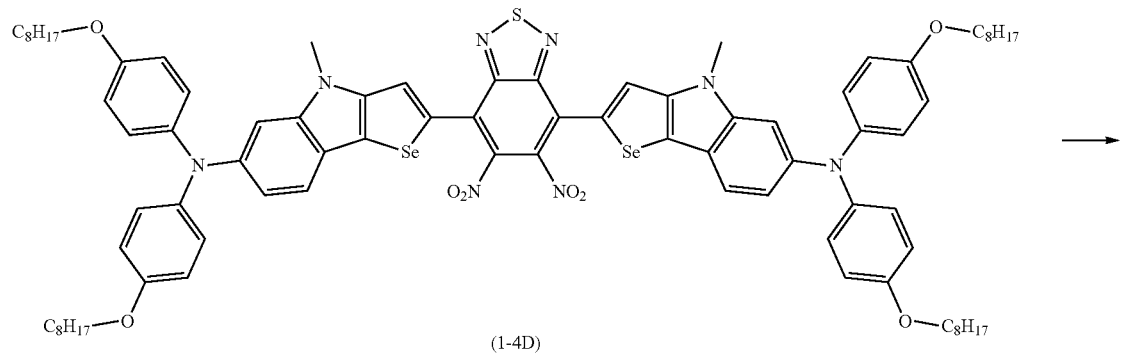
(1-4D)
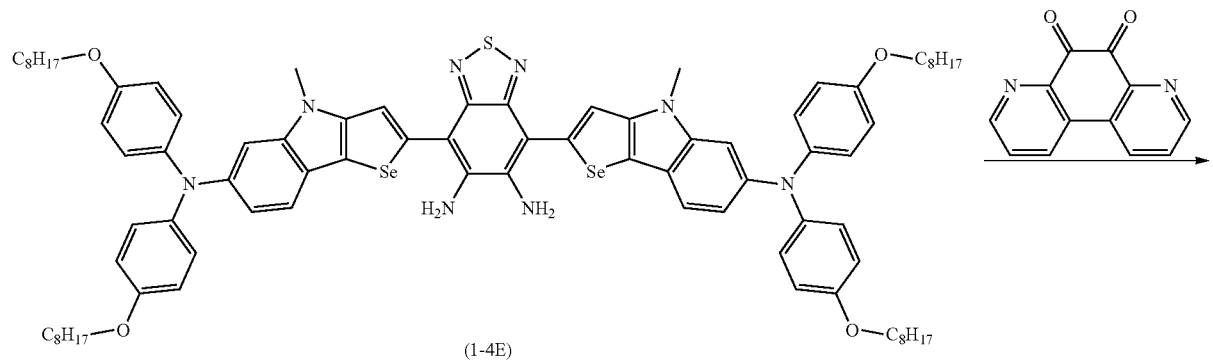
(1-4E)

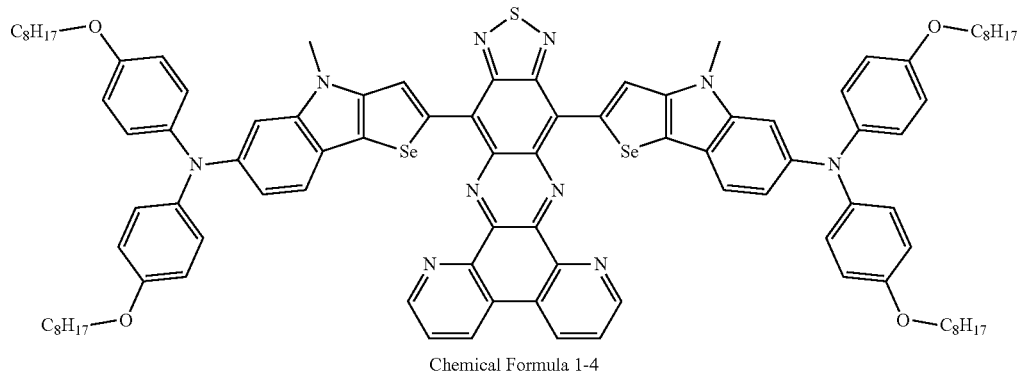

Chemical Formula 1-4 i) First Step: Synthesis of Compound (1-4B)

6-bromo-4-methyl-4H-selenopheno[3,2-b]indole (Compound (1-4A)) (3.4 g, 10.9 mmol) and bis(4-(octyloxy)phenyl)amine (4.6 g, 10.9 mmol) are dissolved in 100 ml of anhydrous toluene and then, heated and refluxed under Pd(dba)$_2$ (5 mol %), P(tBu)$_3$ (5 mol %), and NaOtBu (1.3 g, 13.0 mmol) for 12 hours. The obtained product is separated and purified through silica gel column chromatography (EA:n-Hex=1:20 v/v) to obtain 7.0 g (Yield: 98%) of Compound (1-4B).

LC-MS: 659.32 m/z confirmation of molecular weight.

ii) Second Step: Synthesis of Compound (1-4C)

Compound (1-4B) (4.5 g, 6.8 mmol) is dissolved in anhydrous THF and then, stirred at −78° C. 2.5 M n-BuLi (in n-Hex, 2.7 ml, 6.8 mmol) is slowly added thereto and then, stirred for 3 hours, and then, 1 M trimethyltin chloride (in THF, 6.8 ml, 6.8 mmol) is added thereto and then, heated up to room temperature. The obtained product is extracted with chloroform to obtain 5.6 g (Yield: about 99%) of Compound (1-4C). Compound (1-4C) may be used for the third step reaction without additional purification.

LC-MS: 823.30 m/z confirmation of molecular weight.

iii) Third Step: Synthesis of Compound (1-4D)

4,8-dibromobenzo[1,2-c;4,5-c']bis[1,2,5]thiadiazole (0.9 g, 2.4 mmol), Compound (1-4C) (4 g, 4.9 mmol), and tetrakis(triphenylphosphine)palladium (0) (5 mol %) are dissolved in 100 ml of toluene and then, stirred at 110° C. for 18 hours. When a reaction is completed, after evaporating and removing the toluene, the residue is separated and purified through silica gel column chromatography (MC:n-Hex=1:1 in a volume ratio) to obtain 1.3 g (Yield: 36%) of Compound (1-4D).

LC-MS: 1539.66 m/z confirmation of molecular weight.

iv) Fourth Step: Synthesis of Compound (1-4E)

Compound (1-4D) (1 g, 0.65 mmol) and ammonium formate (2.1 g, 32.5 mmol) are dissolved in ethanol/EA (30/30 ml), and Pd/C (10 wt %, 0.35 g, 0.33 mmol) is added thereto and then, stirred at 70° C. When a reaction is completed, the resultant is separated and purified through silica gel column chromatography (MC:n-Hex=1:1 in a volume ratio) to obtain 0.43 g (Yield: 45%) of Compound (1-4E).

LC-MS: 1477.86 m/z confirmation of molecular weight.

vi) Sixth Step: Synthesis of Compound Represented by Chemical Formula 1-4

Compound (1-4E) (0.1 g, 0.07 mmol) and 4,7-phenanthroline-5,6-dione (0.017 bg, 0.08 mmol) are dissolved in chloroform/acetic acid (5/1 ml) and then, stirred at room temperature for 12 hours. When a reaction is completed, the resultant is precipitated in methanol to obtain 0.07 g (Yield: 63%) of a compound represented by Chemical Formula 1-4.

MALDI-TOF-MS: 1653.66 m/z confirmation of molecular weight.

Synthesis Example 5: Synthesis of Compound Represented by Chemical Formula 1-5
[Chemical Formula 1-5]
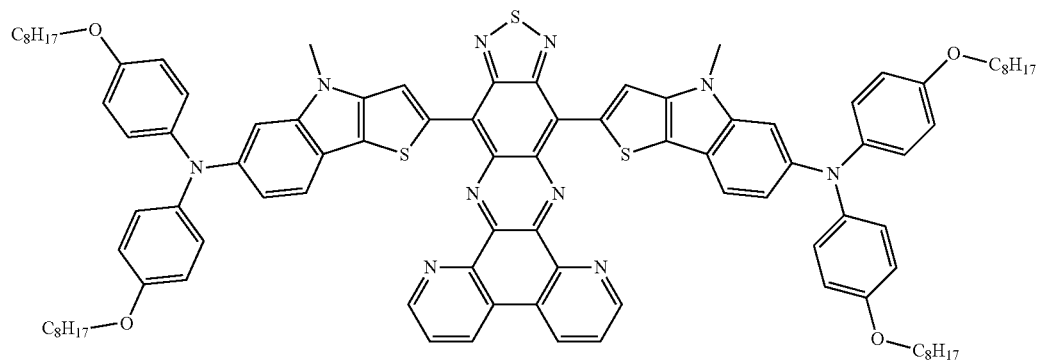
[Reaction Scheme 1-5]
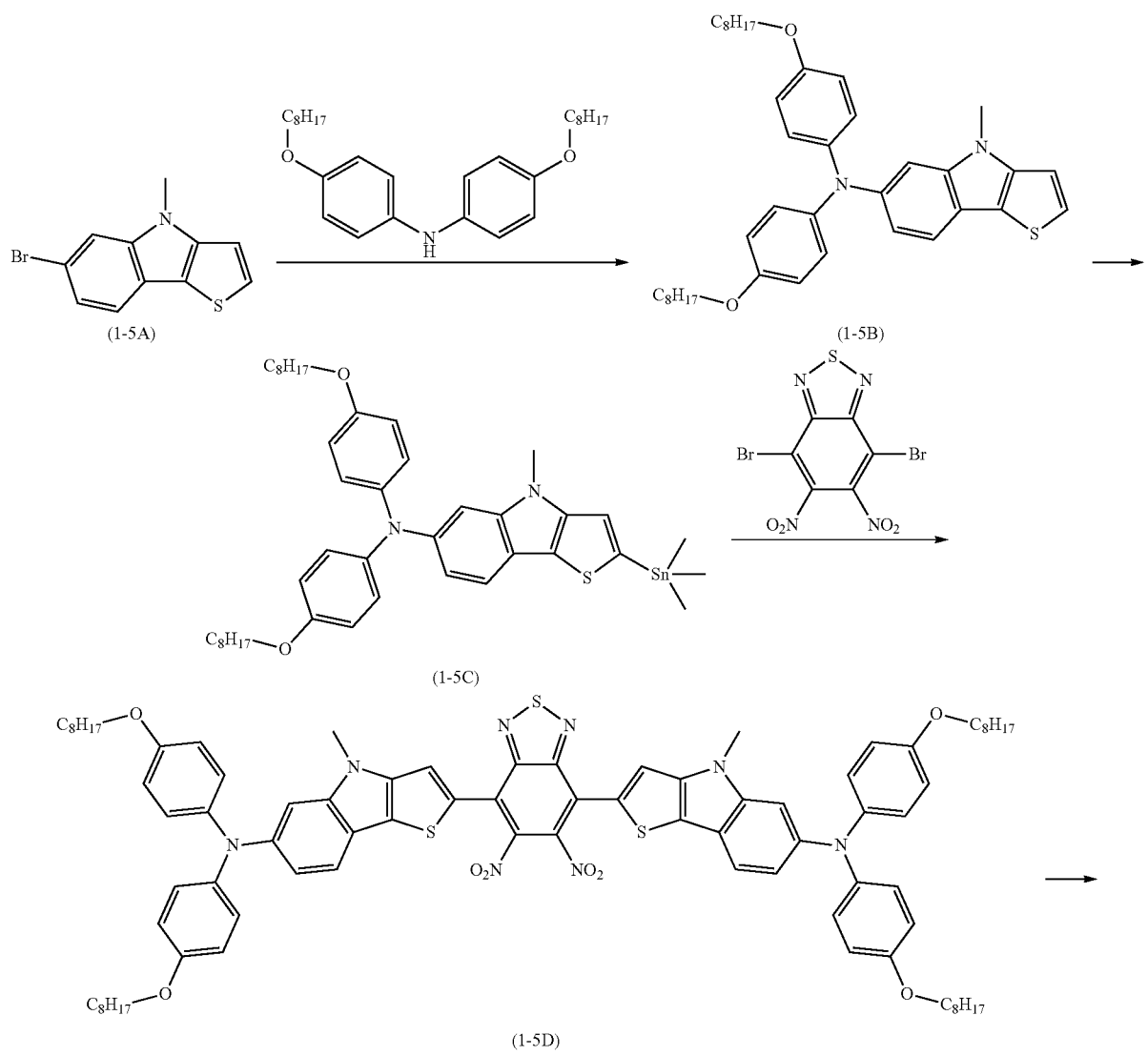

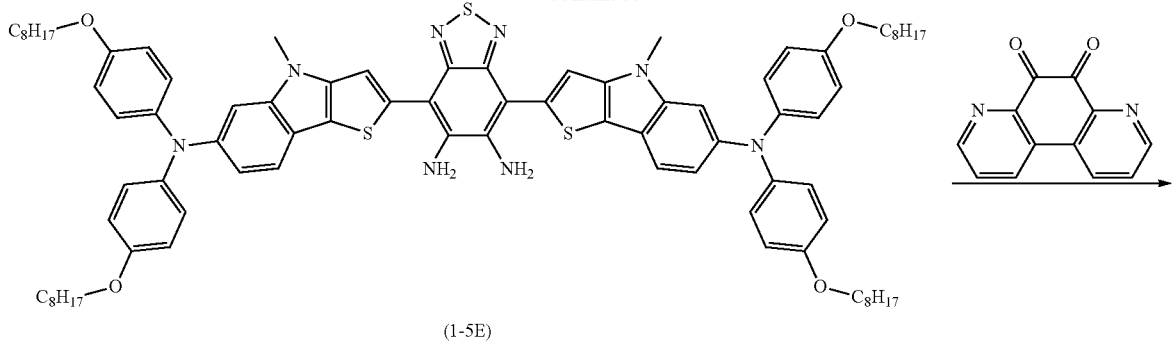

(1-5E)

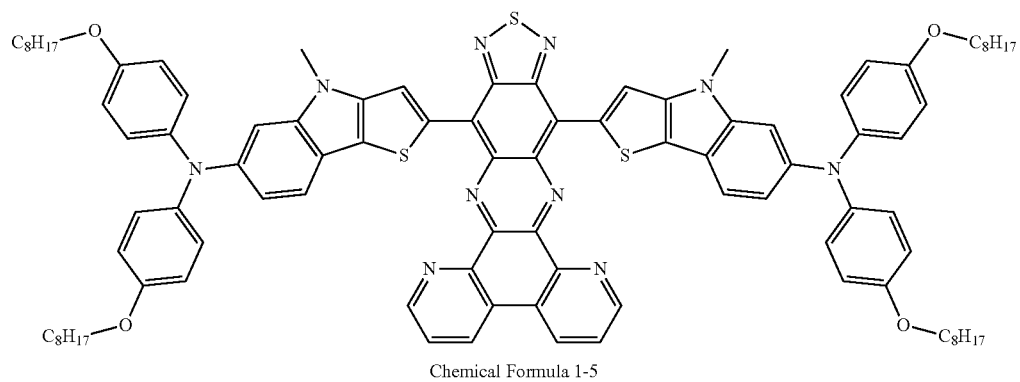

Chemical Formula 1-5 i) First Step: Synthesis of Compound (1-5B)

6-bromo-4-methyl-4H-thieno[3,2-b]indole (Compound (1-5A)) (2.0 g, 7.5 mmol) and bis(4-(octyloxy)phenyl)amine (3.2 g, 7.5 mmol) are heated and refluxed in 100 ml of anhydrous toluene under Pd(dba)$_2$ (5 mol %), P(tBu)$_3$ (5 mol %), and NaOtBu (0.9 g, 9.0 mmol) for 12 hours. The obtained product is separated and purified though silica gel column chromatography (EA:n-Hex=1:20 v/v) to obtain 3.8 g (Yield: 82%) of Compound (1-5B).

LC-MS: 611.35 m/z confirmation of molecular weight.

ii) Second Step: Synthesis of Compound (1-5C)

Compound (1-5B) (3.8 g, 6.2 mmol) is dissolved in anhydrous THF and then, stirred at −78° C. 2.5 M n-BuLi (in n-Hex, 2.5 ml, 6.2 mmol) is slowly added thereto and then, stirred for 3 hours, and 1 M trimethyltin chloride (in THF, 6.2 ml, 6.2 mmol) is added thereto and then, heated up to room temperature. The obtained product is extracted with chloroform to obtain 4.8 g (Yield: about 99%) of Compound (1-5C). Compound (1-5C) may be used without additional purification in the third step reaction.

LC-MS: 775.34 m/z confirmation of molecular weight.

iii) Third Step: Synthesis of Compound (1-5D)

4,8-dibromobenzo[1,2-c;4,5-c']bis[1,2,5]thiadiazole (1.0 g, 2.5 mmol), Compound (1-5C) (4 g, 5.2 mmol), and tetrakis(triphenylphosphine)palladium (0) (5 mol %) are dissolved in 100 ml of toluene and then, stirred at 110° C. for 18 hours. When a reaction is completed, after evaporating and removing the toluene, the residue is separated and purified through silica gel column chromatography (MC:n-Hex=1:1 in a volume ratio) to obtain 2.0 g (Yield: 55%) of Compound (1-5D).

LC-MS: 1443.60 m/z confirmation of molecular weight.

iv) Fourth Step: Synthesis of Compound (1-5E)

Compound (1-5D) (1 g, 0.69 mmol) and ammonium formate (2.2 g, 34.6 mmol) are dissolved in ethanol/ethylacetate (EA) (30 ml/30 ml), and Pd/C (10 wt %, 0.37 g, 0.35 mmol) is added thereto and then, stirred at 70° C. When a reaction is completed, the resultant is separated and purified through silica gel column chromatography (MC:n-Hex=1:1 in a volume ratio) to obtain 0.38 g (Yield: 40%) of Compound (1-5E).

LC-MS: 1383.71 m/z confirmation of molecular weight.

vi) Sixth Step: Synthesis of Compound represented by Chemical Formula 1-5

Compound (1-5E) (0.1 g, 0.07 mmol) and 4,7-phenanthroline-5,6-dione (0.017 g, 0.08 mmol) are dissolved in chloroform/acetic acid (5 ml/1 ml) and then, stirred at room temperature for 12 hours. When a reaction is completed, the resultant is precipitated in methanol to obtain 0.06 g (Yield: 53%) of a compound represented by Chemical Formula 1-5.

MALDI-TOF-MS: 1557.71 m/z confirmation of molecular weight.

Synthesis Example 6: Synthesis of Compound represented by Chemical Formula 1-6
[Chemical Formula 1-6]
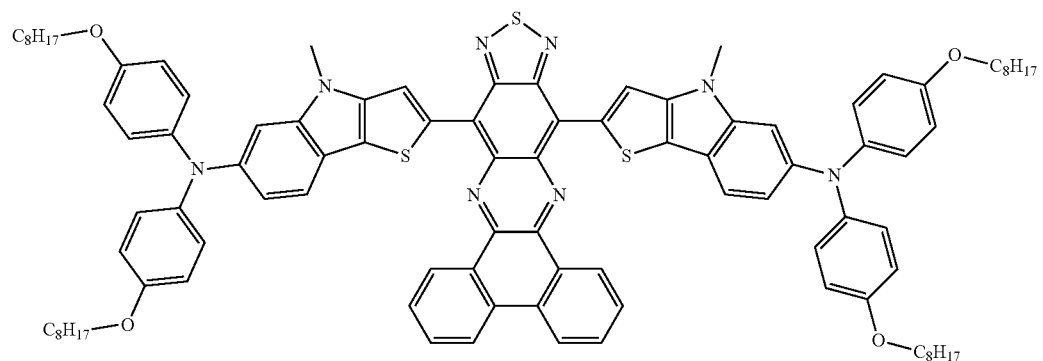
[Reaction Scheme 1-6]
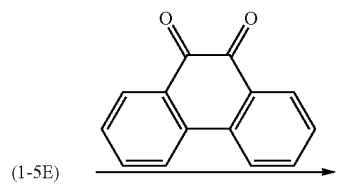
(1-5E)
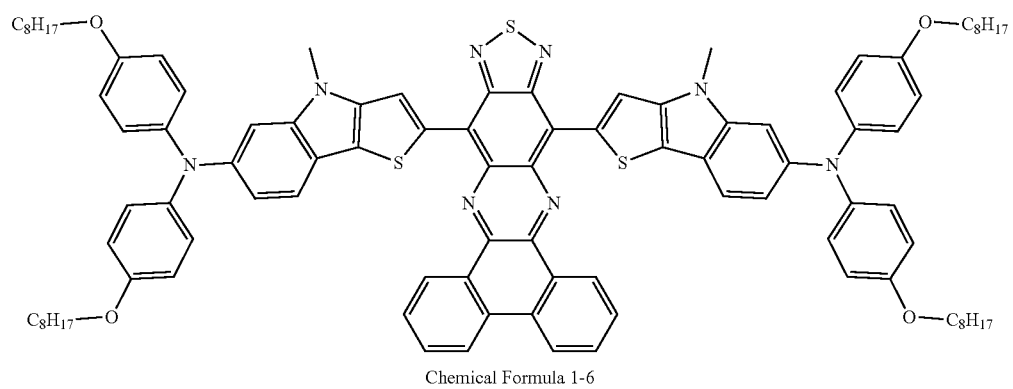
Chemical Formula 1-6 vi) First Step: Synthesis of Compound Represented by Chemical Formula 1-6

Compound (1-5E) (0.1 g, 0.07 mmol) and phenanthrene-9,10-dione (0.017 g, 0.08 mmol) are dissolved in chloroform/acetic acid (5/1 ml) and then, stirred at room temperature for 12 hours. When a reaction is completed, the resultant is precipitated in methanol to obtain a material. 0.06 g (Yield: 53%) of a compound represented by Chemical Formula 1-6 is obtained.

MALDI-TOF-MS: 1555.69 m/z confirmation of molecular weight.

Comparative Synthesis Example 1: Synthesis of Compound Represented by Chemical Formula 2-1

[Chemical Formula 2-1]

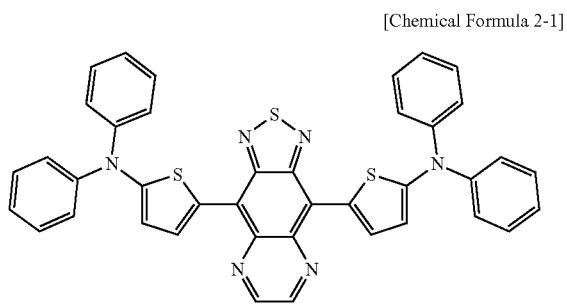 [SMILES: c1ccc(N(c2ccccc2)c2ccc(-c3c4nccnc4c(-c4ccc(N(c5ccccc5)c5ccccc5)s4)c4nsnc34)s2)cc1]

In a round-bottomed flask, 4,9-dibromo-[1,2,5]thiadiazolo[3,4-g]quinoxaline (Compound (2-1A)) (1.13 g, 3.26 mmol) and N,N-diphenyl-5-(tributylstannyl)thiophen-2-amine (Compound (2-1B)) (4.4 g, 8.14 mmol) are dissolved in toluene (15 ml) under a nitrogen pressure, and tetrakis(triphenylphosphine)-palladium (0) (0.376 g, 0.326 mmol) is added thereto. Subsequently, the obtained mixture is heated up to 110° C. and refluxed and stirred for 24 hours. The reactant is cooled down to room temperature (24° C.) and concentrated, and ethylacetate is added thereto. Subsequently, a solid produced therein is filtered and washed with n-hexane/ethylacetate/methanol. The obtained solid is vacuum-dried to obtain a compound represented by Chemical Formula 2-1 (1.5 g) as a green solid.

$^1$H NMR (500 MHz, CDCl$_3$): d 8.92 (d, 2H), d 8.75 (s, 2H), d 7.35 (t, 8H), d 7.30 (d, 8H), d 7.14 (t, 4H), d 6.75 (d, 2H).

UPLC-MS: [M+H]$^+$ 687.06.

Comparative Synthesis Example 2: Synthesis of Compound Represented by Chemical Formula 2-2

A method described in an article (D. Ma, Z. Y. Wang et al. J. Phys. Chem. C, 2009, 113, 1589-1595) is used to synthesize a compound represented by Chemical Formula 2-2.

[Chemical Formula 2-2]

Comparative Synthesis Example 3: Synthesis of Compound Represented by Chemical Formula 2-3

[Chemical Formula 2-3]

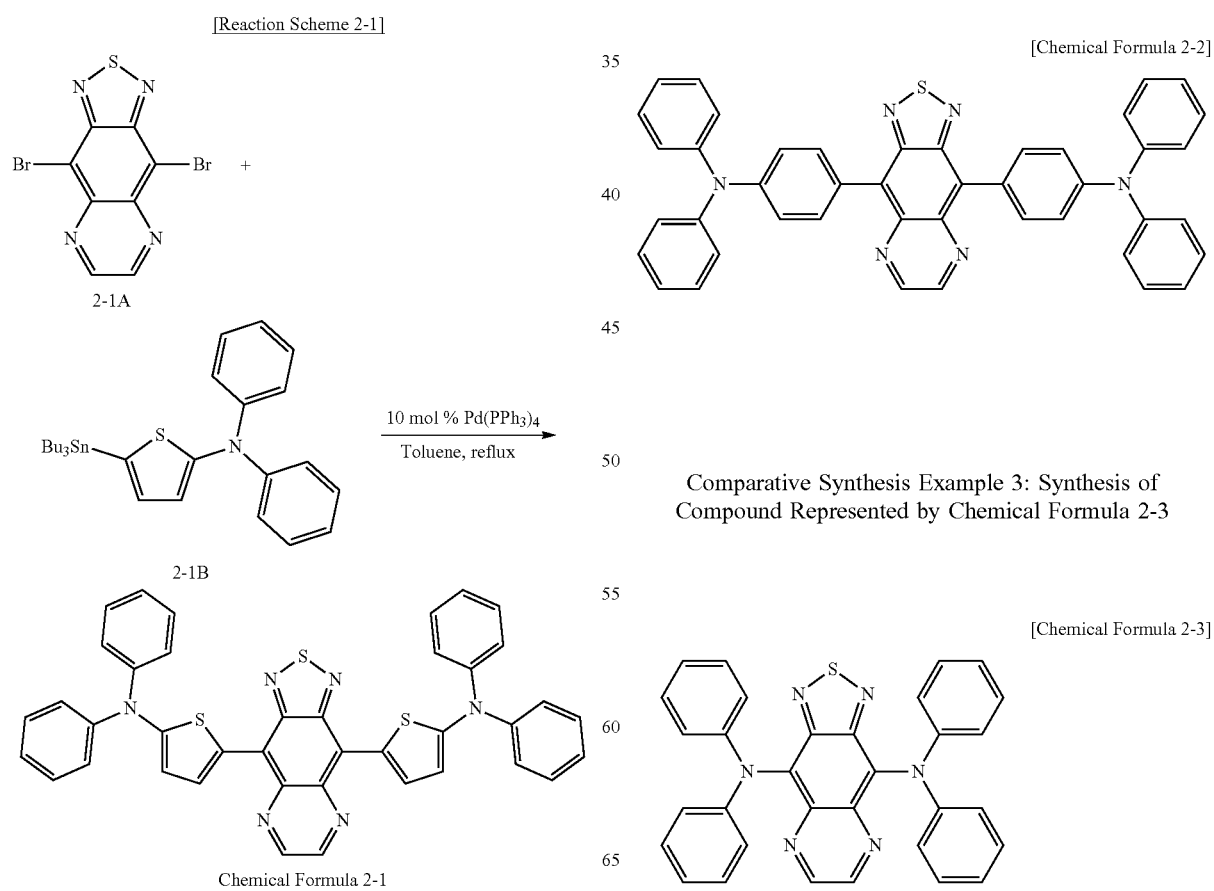

[Reaction Scheme 2-1]

Chemical Formula 2-1

[Reaction Scheme 2-3]

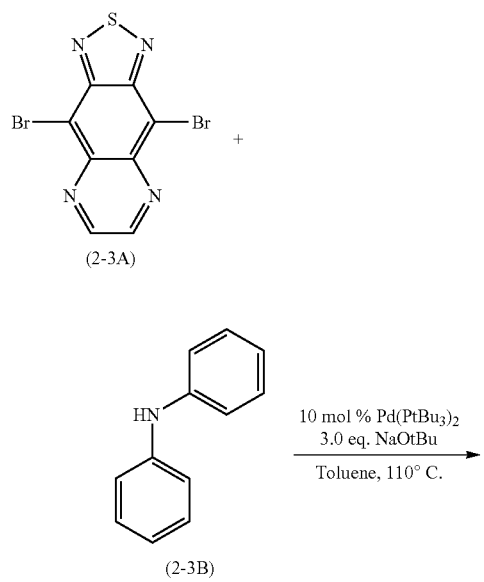

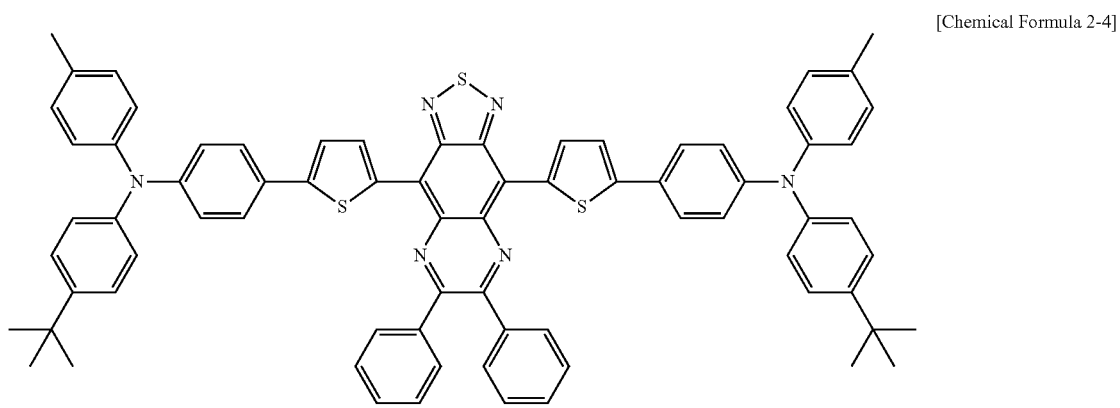 [SMILES: Cc1ccc(N(c2ccc(-c3ccc(-c4c5nsnc5c(-c5ccc(-c6ccc(N(c7ccc(C)cc7)c7ccc(C(C)(C)C)cc7)cc6)s5)c5nc(-c6ccccc6)c(-c6ccccc6)nc45)s3)cc2)c2ccc(C(C)(C)C)cc2)cc1]

[Chemical Formula 2-4]

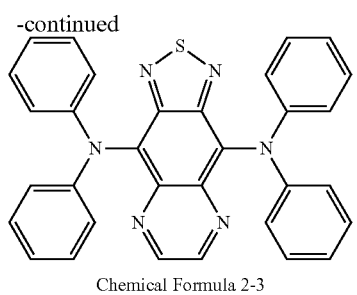

Chemical Formula 2-3

In a round-bottomed flask, 4,9-dibromo-[1,2,5]thiadiazolo[3,4-g]quinoxaline (Compound (2-3A)) (530 mg, 1.53 mmol), diphenylamine (Compound (2-3B)) (646 mg, 3.82 mmol), and sodium tert-butoxide (317 mg, 4.59 mmol) are dissolved in toluene (10 ml) under a nitrogen pressure, and bis(tri-tert-butylphosphine)palladium (0) (78 mg, 0.153 mmol) is added thereto. Subsequently, the mixture is heated up to 110° C. and then, refluxed and stirred for 24 hours. The reactant is cooled down to room temperature (24° C.) and concentrated, and then, ethylacetate, distilled water, and an ammonium chloride aqueous solution in order are added thereto. An organic layer is extracted therefrom by using ethyl acetate and dried with MgSO$_4$. After filtering out MgSO$_4$, the solution is concentrated and then, treated through silica chromatography (ethyl acetate:n-hexane=1:4 in a volume ratio). The purified material is vacuum-dried to obtain 120 mg (Yield: 15%) of a green solid.

$^1$H NMR (300 MHz, CD$_2$Cl$_2$): d 8.57 (s, 2H), d 7.19 (d, 8H), d 7.06 (d, 8H), d 6.98 (t, 4H).

UPLC-MS: [M+H]$^+$ 523.14.

Comparative Synthesis Example 4: Synthesis of Compound Represented by Chemical Formula 2-4

A method of Scheme 1 described in an article (ACS Nano, Highly Stable Organic Small Molecular Nanoparticles as an Advanced and Biocompatible Phototheranostic Agent of Tumor in Living Mice, 2017, 7177-7188) is used to synthesize a compound represented by Chemical Formula 2-4.

Evaluation I: Light Absorption Characteristics

The compounds according to Synthesis Examples 1 to 6 and Comparative Synthesis Examples 1 to 4 are respectively dissolved in a solvent at a concentration of 1×10$^{-5}$ M to prepare solutions, and light absorption characteristics of the compounds in a solution state are evaluated. The light absorption characteristics are evaluated by measuring a maximum absorption wavelength ($\lambda_{max}$) with a UV-Vis-NIR spectrometer of Shimadzu UV-3600 Plus. On the other hand, DFT, TD-DFT (wB97X-D function with 6-311G(d,p) basis set) of the compounds of Synthesis Examples 1 to 6 and Comparative Synthesis Examples 1 to 4 are calculated by using a Gaussian09 (G09) program assuming that the samples are toluene solutions to obtain oscillator strengths. The results are shown in Table 1.

TABLE 1

|  | $\lambda_{max}$ (nm) | Oscillator Strength (a.u.) |
| --- | --- | --- |
| Synthesis Example 1 | 1260 | 0.91 |
| Synthesis Example 2 | 1120 | 0.99 |
| Synthesis Example 3 | 1170 | 0.97 |
| Synthesis Example 4 | 1260 | 0.91 |
| Synthesis Example 5 | 1170 | 0.94 |
| Synthesis Example 6 | 1030 | 1.00 |
| Comparative Synthesis Example 1 | 829 | 0.77 |
| Comparative Synthesis Example 2 | 594 | 0.55 |
| Comparative Synthesis Example 3 | 692 | 0.25 |
| Comparative Synthesis Example 4 | 780 | 0.78 |

Referring to Table 1, the compounds of Synthesis Examples 1 to 60j exhibit satisfactory wavelength absorptions in an infrared wavelength region compared with the compounds of Comparative Synthesis Examples 1 to 4. In addition, the compounds according to Synthesis Examples 1 to 6 exhibit high oscillator strength and thus may be expected to have a high absorption coefficient, compared with the compounds according to Comparative Synthesis Examples 1 to 4.

Evaluation II: Energy Level and Bandgap

HOMO energy levels, LUMO energy levels, and bandgaps are calculated by using a theory of B3LYP/6-31 G(d) level described by M. J. Frisch, et al., Gaussian 09, Revision D.01; Gaussian, Inc.: Wallingford, Conn. 2009]. The results are shown in Table 2.

TABLE 2

|  | HOMO (eV) | LUMO (eV) | Bandgap energy (eV) |
| --- | --- | --- | --- |
| Synthesis Example 1 | −4.16 | −3.27 | 0.89 |
| Synthesis Example 2 | −4.28 | −3.26 | 1.02 |
| Synthesis Example 3 | −4.27 | −3.33 | 0.94 |
| Synthesis Example 4 | −4.16 | −3.27 | 0.89 |
| Synthesis Example 5 | −4.20 | −3.23 | 0.97 |
| Synthesis Example 6 | −4.31 | −3.22 | 1.09 |
| Comparative Synthesis Example 1 | −4.61 | −3.11 | 1.50 |
| Comparative Synthesis Example 2 | −5.26 | −3.70 | 1.56 |
| Comparative Synthesis Example 3 | −5.03 | −3.24 | 1.79 |
| Comparative Synthesis Example 4 | −4.66 | −3.20 | 1.46 |

Referring to Table 2, the compounds of Synthesis Examples 1 to 6 exhibit reduced bandgap energies and thus may not effectively absorb light in an infrared wavelength region, compared with the compounds of Comparative Synthesis Examples 1 to 4.

Examples 1 to 6: Production of Photoelectric Device

A 150 nm-thick anode is formed by sputtering ITO on a glass substrate. Each of the compounds according to Synthesis Examples 1 to 6 and PCBM ([6,6]-phenyl-C6i-butyric acid methyl ester) are mixed in chloroform in a 1:1 volume ratio, and then spin-coated on the anode to produce a 150 nm-thick photoactive layer (photoelectric conversion layer). Subsequently, C60 is deposited on the photoactive layer to form a 30 nm-thick auxiliary layer. Then, ITO is sputtered on the auxiliary layer to form a 7 nm-thick cathode. Then, aluminum oxide ($Al_2O_3$) was deposited on the cathode to form a 50 nm-thick anti-reflection layer and sealed with a glass plate to produce the photoelectric devices according to Examples 1 to 6.

Comparative Examples 1 to 4: Production of Photoelectric Device

A 150 nm-thick anode is formed by sputtering ITO on a glass substrate. Subsequently, each of the compounds obtained in Comparative Synthesis Examples 1 to 4 and C60 are co-deposited on the anode in a volume ratio of 1:1, respectively, to form a 150 nm-thick photoactive layer (photoelectric conversion layer). Subsequently, C60 is deposited on the photoactive layer to form an auxiliary layer. Then, ITO is sputtered on the auxiliary layer to form a 7 nm-thick cathode. Then, aluminum oxide ($Al_2O_3$) was deposited on the cathode to form a 50 nm-thick anti-reflection layer and sealed with a glass plate to produce the photoelectric devices according to Comparative Examples 1 to 4.

Evaluation III: Photoelectric Conversion Efficiency

Photoelectric conversion efficiency of the photoelectric devices according to Examples 1 to 6 and Comparative Examples 1 to 4 is evaluated. The photoelectric conversion efficiency is measured by using an IPCE measurement system (TNE Technology Co., Ltd., Korea). First, the system is calibrated by using a Si photodiode (Hamamatsu Photonics K.K., Japan) and then, mounted on a photoelectric device to measure the photoelectric conversion efficiency in a wavelength range of about 400 nm to about 1600 nm. The results of Example 1 and Comparative Example 3 are shown in FIG. 13.

Figure 13:
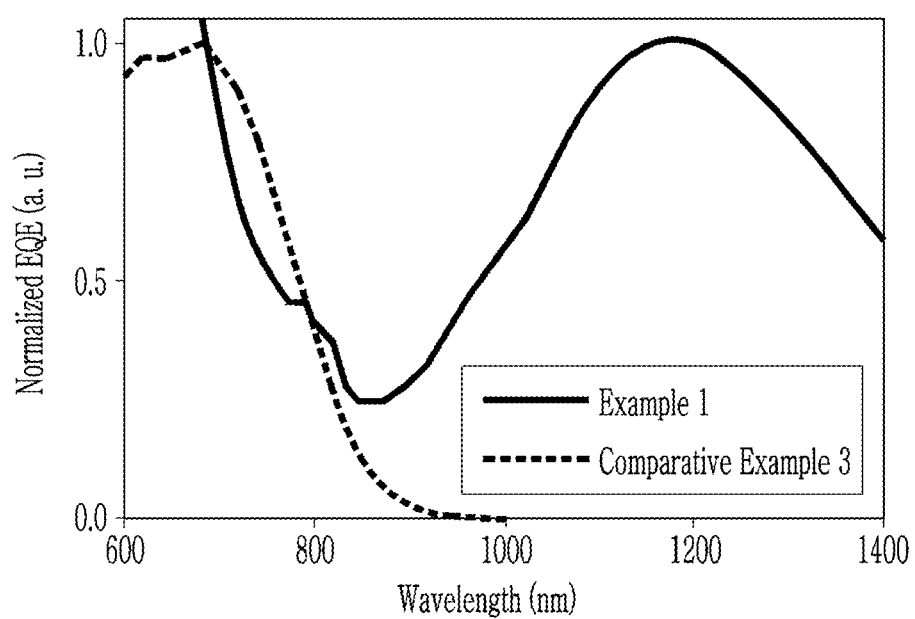
FIG. 13 is a graph showing the results of measuring the photoelectric conversion efficiency of the photoelectric devices according to Example 1 and Comparative Example 3.

FIG. 13 is a graph showing the results of measuring the photoelectric conversion efficiency of the photoelectric devices according to Example 1 and Comparative Example 3.

Referring to FIG. 13, the photoelectric device according to Example 1 exhibits superior photoelectric conversion efficiency in a long wavelength region of about 1200 nm compared with the photoelectric device according to Comparative Example 3.

While this disclosure has been described in connection with what is presently considered to be practical example embodiments, it is to be understood that the inventive concepts are not limited to the described example embodiments. On the contrary, the inventive concepts are intended to cover various modifications and equivalent arrangements included within the spirit and scope of the appended claims,

DESCRIPTION OF SYMBOLS

| | |
| --- | --- |
| 10: first electrode | 20: second electrode |
| 30: photoactive layer | 50a, 50b, 50c: photodiode |
| 55: charge storage | 70a, 70b, 70c: color filter |
| 80: insulation layer | 100: photoelectric device |
| 10B, 10G, 10R, 10IR: first electrode | |
| 20B, 20G, 20R, 20IR: second electrode | |
| 30B, 30G, 30R, 30IR: photoactive layer | |
| 50B: blue light charge storage | |
| 50G: green light charge storage | |
| 50R: red light charge storage | |
| 50IR: infrared light charge storage | |
| 110: semiconductor substrate | 65: lower insulation layer |
| 70a, 70b, 70c: color filter layer | 85: upper insulation layer |
| 100B: blue photo-sensing device | 100G: green photo-sensing device |
| 100R: red photo-sensing device | 100IR: infrared photo-sensing device |
| 300, 400, 500, 600, 700: image sensor | |

What is claimed is:

1. An infrared absorber, comprising:
a compound represented by Chemical Formula 1:

[Chemical Formula 1]

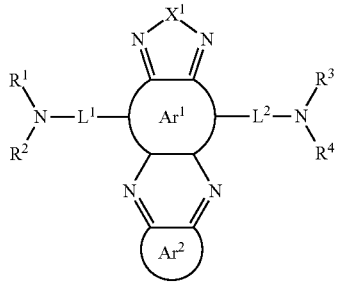

wherein, in Chemical Formula 1,
$Ar^1$ is a substituted or unsubstituted C6 to C30 aromatic ring, a substituted or unsubstituted C3 to C30 heteroaromatic ring, or a combination thereof,
$Ar^2$ is a substituted or unsubstituted C6 to C30 aromatic ring, a substituted or unsubstituted C3 to C30 heteroaromatic ring, or a combination thereof,
$X^1$ is O, S, Se, Te, S(=O), S(=O)$_2$, NR$^a$, CR$^b$R$^c$, or SiR$^d$R$^e$, wherein R$^a$, R$^b$, R$^c$, R$^d$, and R$^e$ are each independently hydrogen, deuterium, a C1 to C6 alkyl group, a C1 to C6 haloalkyl group, a C6 to C12 aryl group, a C3 to C12 heteroaryl group, a halogen, a cyano group, or a combination thereof,
$R^1$, $R^2$, $R^3$, and $R^4$ are each independently hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof,
$R^1$ and $R^2$ each independently exist or are linked to each other to form a first ring, and $R^3$ and $R^4$ each independently exist or are linked to each other to form a second ring, and
$L^1$ is represented by Chemical Formula 1A or Chemical Formula 1B, and $L^2$ is represented by Chemical Formula 1C or Chemical Formula 1D:

[Chemical Formula 1A]

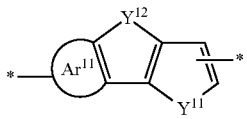

[Chemical Formula 1B]

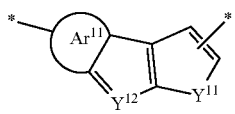

wherein, in Chemical Formula 1A and Chemical Formula 1B,
$Y^{11}$ and $Y^{12}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof,
$Ar^{11}$ is a substituted or unsubstituted C6 to C30 aromatic ring, a substituted or unsubstituted C3 to C30 heteroaromatic ring, or a combination thereof, and
* on a left side of Chemical Formula 1A and Chemical Formula 1B is a portion that is bound to N of —N(R$^1$)(R$^2$) of Chemical Formula 1, and * on a right side of Chemical Formula 1A and Chemical Formula 1B is a portion that is bound to Ar$^1$ of Chemical Formula 1,

[Chemical Formula 1C]

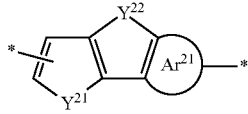

[Chemical Formula 1D]

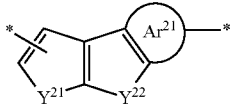

wherein, in Chemical Formula 1C and Chemical Formula 1D,
$Y^{21}$ and $Y^{22}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof,
$Ar^{21}$ is a substituted or unsubstituted C6 to C30 aromatic ring, a substituted or unsubstituted C3 to C30 heteroaromatic ring, or a combination thereof, and
* on a left side of Chemical Formula 1C and Chemical Formula 1D is a portion that is bound to Ar$^1$ of Chemical Formula 1, and * on a right side of Chemical Formula 1C and Chemical Formula 1D is a portion that is bound to N of —N(R$^3$)(R$^4$) of Chemical Formula 1.

2. The infrared absorber of claim 1, wherein in Chemical Formula 1, Ar$^1$ is a substituted or unsubstituted benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

3. The infrared absorber of claim 1, wherein in Chemical Formula 1, Ar$^1$ is a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

4. The infrared absorber of claim 1, wherein in Chemical Formula 1, Ar$^1$ is one moiety of a set of moieties represented by Chemical Formula A-1, each moiety including at least one aromatic ring and left and right linking groups:

[Chemical Formula A-1]

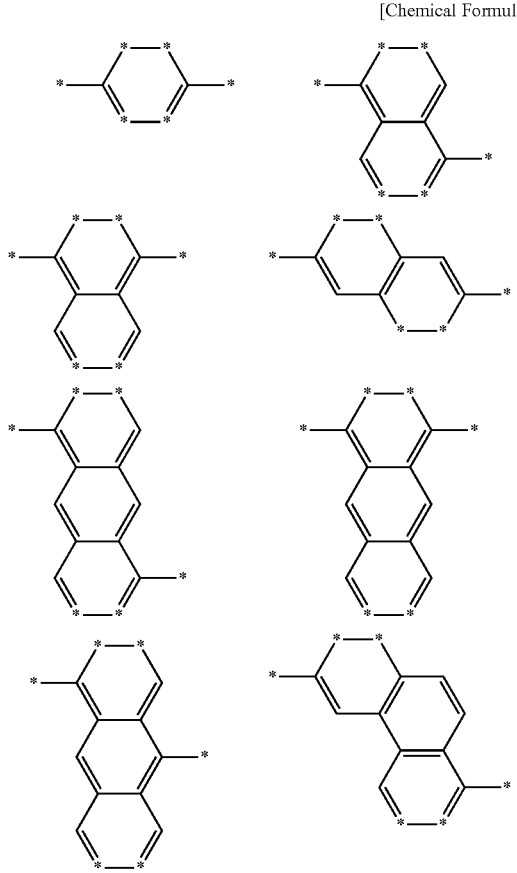

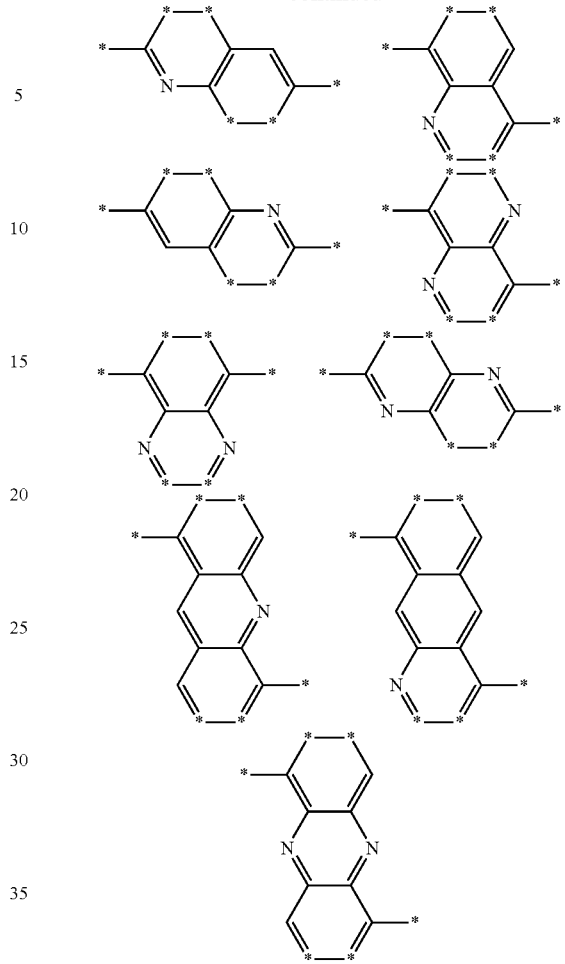

wherein, in Chemical Formula A-1,
   hydrogen of each aromatic ring is optionally replaced by deuterium, a halogen, a cyano group, a C1 to C10 alkyl group, a C1 to C10 haloalkyl group, a silyl group, or a C1 to C10 alkylsilyl group,
   separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and
   *'s of the left and right linking groups are linking portions linked to separate, respective ones of $L^1$ and $L^2$ of Chemical Formula 1.

5. The infrared absorber of claim 1, wherein in Chemical Formula 1, $Ar^1$ is one moiety of a set of moieties represented by Chemical Formula A-2, each moiety including at least one aromatic ring and left and right linking groups:

[Chemical Formula A-2]

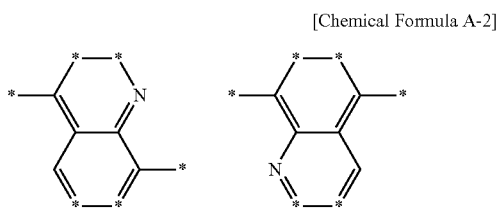

wherein, in Chemical Formula A-2,
   hydrogen of each aromatic ring is optionally replaced by deuterium, a halogen, a cyano group, a C1 to C10 alkyl group, a C1 to C10 haloalkyl group, a silyl group, or a C1 to C10 alkylsilyl group,
   separate adjacent pairs of *'s inside the at least one aromatic ring are linking portions with separate, respective ones of an N—$X^1$—N-containing pentagonal ring of Chemical Formula 1 and an N-containing hexagonal ring of Chemical Formula 1, and
   *'s of the left and right linking groups are linking portions linked to separate, respective ones of $L^1$ and $L^2$ of Chemical Formula 1.

6. The infrared absorber of claim 1, wherein in Chemical Formula 1, $Ar^2$ is a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring, or a substituted or unsubstituted pyrene ring.

7. The infrared absorber of claim 1, wherein in Chemical Formula 1, $Ar^2$ is a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

8. The infrared absorber of claim 1, wherein in Chemical Formula 1, $Ar^2$ is one moiety of a set of moieties represented by Chemical Formula B-1, each moiety including at least one aromatic ring:

[Chemical Formula B-1]

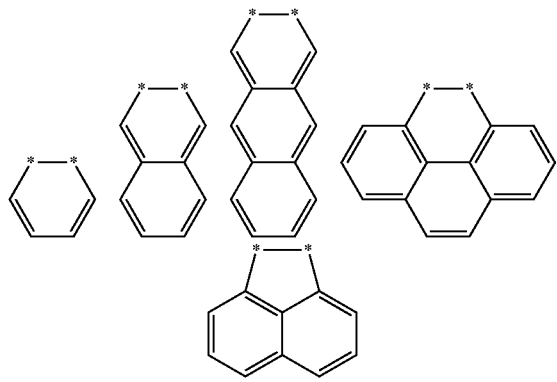

wherein, in Chemical Formula B-1,
hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and
adjacent pairs of *'s inside the at least one aromatic ring are linking portions with an N-containing hexagonal ring of Chemical Formula 1.

9. The infrared absorber of claim 1, wherein in Chemical Formula 1, $Ar^2$ is one moiety of a set of moieties represented by Chemical Formula B-2, each moiety including at least one aromatic ring:

[Chemical Formula B-2]

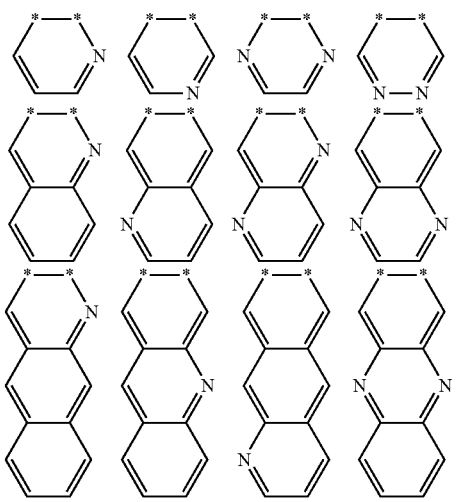

wherein, in Chemical Formula B-2,
hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and
adjacent pairs of *'s inside the at least one aromatic ring are linking portions with an N-containing hexagonal ring of Chemical Formula 1.

10. The infrared absorber of claim 1, wherein in Chemical Formula 1, $Ar^2$ is one moiety of a set of moieties represented by Chemical Formula B-3-1 or Chemical Formula B-3-2, each moiety including at least one aromatic ring:

[Chemical Formula B-3-1]

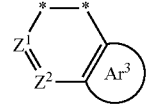

[Chemical Formula B-3-2]

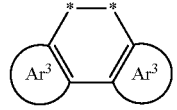

wherein, in Chemical Formula B-3-1 and Chemical Formula B-3-2,
$Ar^3$ and $Ar^4$ are each independently a substituted or unsubstituted C6 to C30 arene group or a substituted or unsubstituted C3 to C30 heteroarene group,
in Chemical Formula B-3-1 $Z^1$ and $Z^2$ are each independently $CR^a$ or N, wherein $R^a$ is hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, and
adjacent pairs of *'s inside the at least one aromatic ring are linking portions with an N-containing hexagonal ring of Chemical Formula 1.

11. The infrared absorber of claim 10, wherein the moiety represented by Chemical Formula B-3-1 is one moiety of a set of moieties represented by Chemical Formula B-3-11:

[Chemical Formula B-3-11]

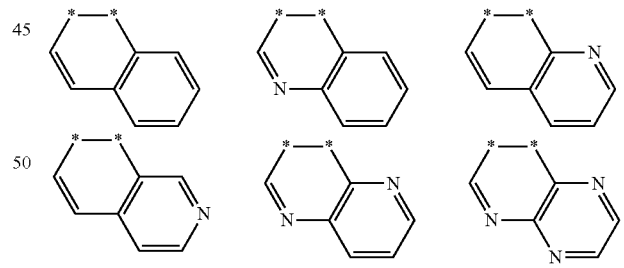

wherein, in Chemical Formula B-3-11,
hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, and
adjacent pairs of *'s inside the at least one aromatic ring are linking portions with an N-containing hexagonal ring of Chemical Formula 1.

12. The infrared absorber of claim 10, wherein the moiety represented by Chemical Formula B-3-2 is one moiety of a set of moieties represented by Chemical Formula B-3-21:

[Chemical Formula B-3-21]

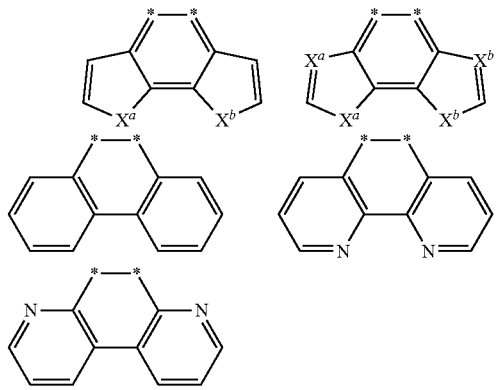

wherein, in Chemical Formula B-3-21, hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, adjacent pairs of *'s inside the at least one aromatic ring are linking portions with an N-containing hexagonal ring of Chemical Formula 1, and $X^a$ and $X^b$ are each independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are each independently hydrogen, deuterium, a halogen, a substituted or unsubstituted C1 to C10 alkyl group, or a substituted or unsubstituted C6 to C10 aryl group.

13. The infrared absorber of claim 1, wherein in Chemical Formula 1, $L^1$ is represented by Chemical Formula 1A-1 or Chemical Formula 1B-1:

[Chemical Formula 1A-1]

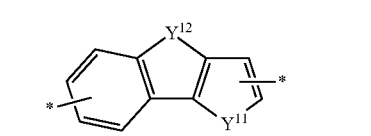
(1A-1a)

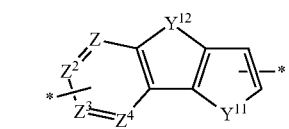
(1A-1b)

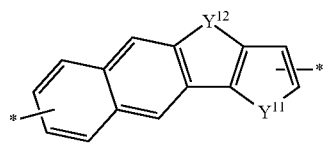
(1A-1c)

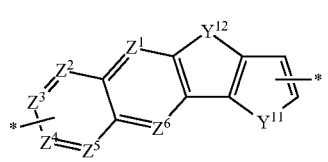
(1A-1d)

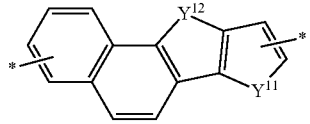
(1A-1e)

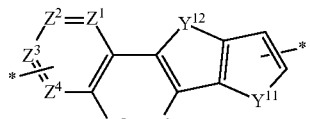
(1A-1f)

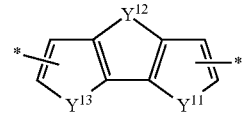
(1A-1g)

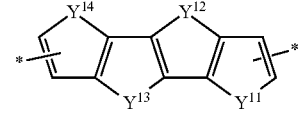
(1A-1h)

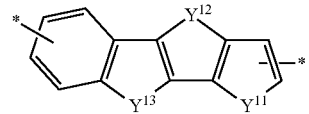
(1A-1i)

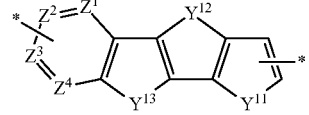
(1A-1j)

wherein, in Chemical Formula 1A-1, hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{11}$, $Y^{12}$, $Y^{13}$, and $Y^{14}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ are each independently N or CR$^x$, wherein R$^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1A-1b and Chemical Formula 1A-1 j is N, and at least one of $Z^1$ to $Z^6$ in Chemical Formula 1A-1d and Chemical Formula 1A-1 f is N, and

* on a left side of Chemical Formula 1A-1 is a portion that is bound to N of —N(R$^1$)(R$^2$) of Chemical Formula 1, and * on a right side of Chemical Formula 1A-1 is a portion that is bound to Ar$^1$ of Chemical Formula 1,

[Chemical Formula 1B-1]

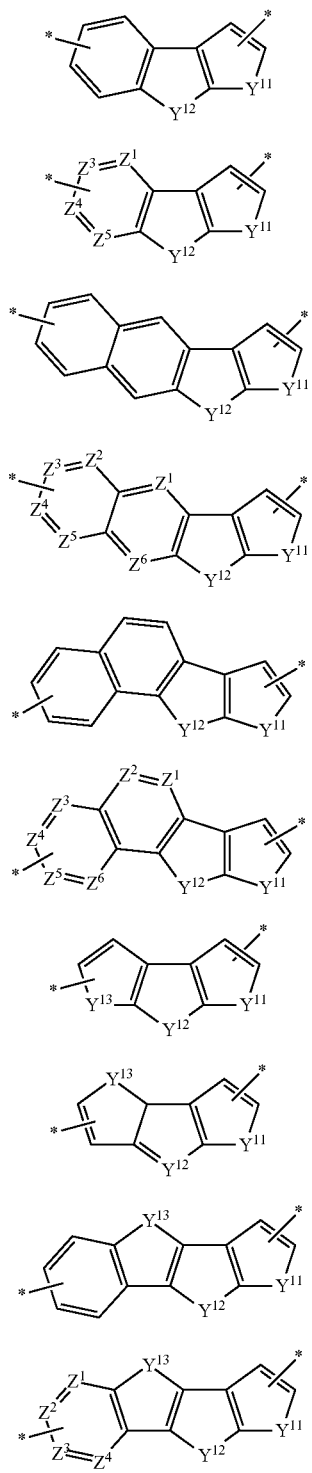

(1B-1a)
(1B-1b)
(1B-1c)
(1B-1d)
(1B-1e)
(1B-1f)
(1B-1g)
(1B-1h)
(1B-1i)
(1B-1j)

wherein, in Chemical Formula 1B-1, hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{11}$, $Y^{12}$, and $Y^{13}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ are each independently N or CR$^x$, wherein R$^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1B-1 b and Chemical Formula 1B-1 j is N, and at least one of $Z^1$ to $Z^6$ in Chemical Formula 1B-1 d and Chemical Formula 1B-1 f is N, and

* on a left side of Chemical Formula 1B-1 is a portion that is bound to N of —N(R$^1$)(R$^2$) of Chemical Formula 1, and * on a right side of Chemical Formula 1B-1 is a portion that is bound to Ar$^1$ of Chemical Formula 1.

14. The infrared absorber of claim 1, wherein in Chemical Formula 1, L$^2$ is represented by Chemical Formula 1C-1 or Chemical Formula 1D-1:

[Chemical Formula 1C-1]

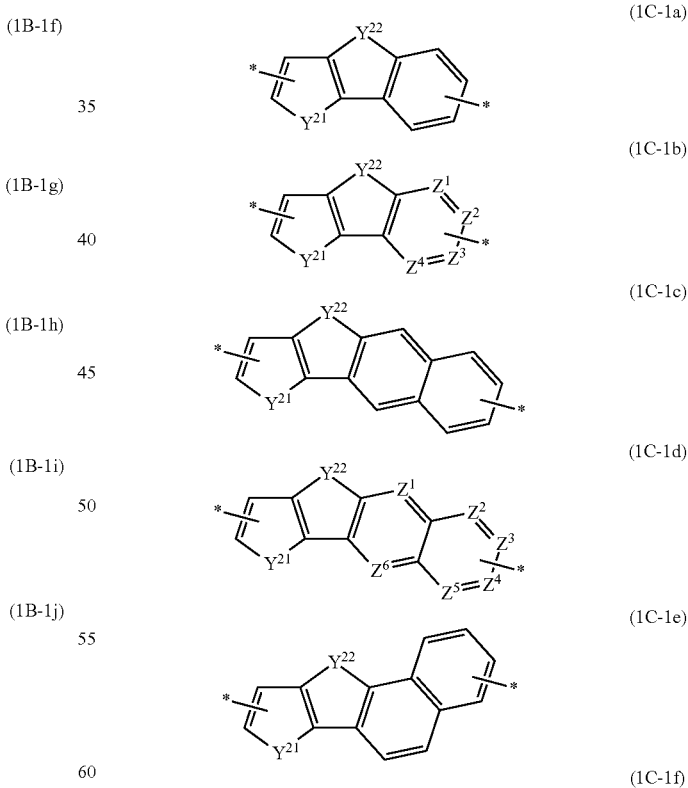

(1C-1a)
(1C-1b)
(1C-1c)
(1C-1d)
(1C-1e)
(1C-1f)

-continued

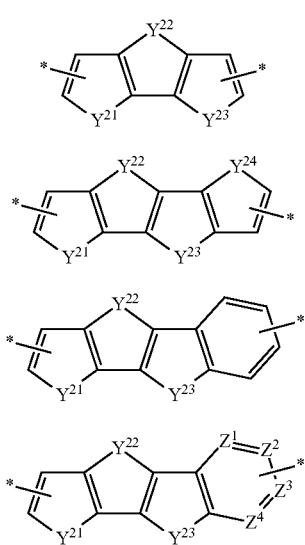

(1C-1g)

(1C-1h)

(1C-1i)

(1C-1j)

wherein, in Chemical Formula 1C-1,
hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, $Y^{23}$, and $Y^{24}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ are each independently N or CR$^x$, wherein R$^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1C-1b and Chemical Formula 1C-1 j is N, and at least one of $Z^1$ to $Z^6$ in Chemical Formula 1C-1d and Chemical Formula 1C-1 f is N, and

* on a left side of Chemical Formula 1C-1 is a portion that is bound to Ar$^1$ of Chemical Formula 1, and * on a right side of Chemical Formula 1C-1 is a portion that is bound to N of —N(R$^3$)(R$^4$) of Chemical Formula 1,

[Chemical Formula 1D-1]

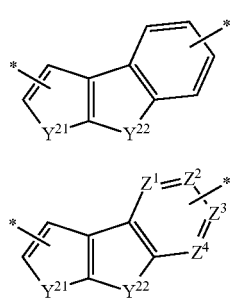

(1D-1a)

(1D-1b)

-continued

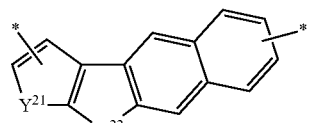

(1D-1c)

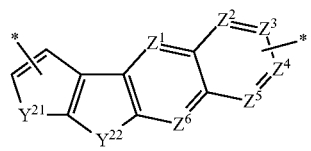

(1D-1d)

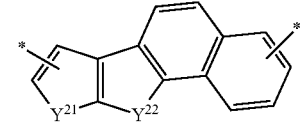

(1D-1e)

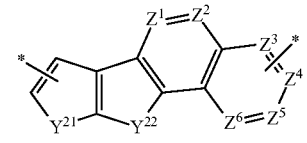

(1D-1f)

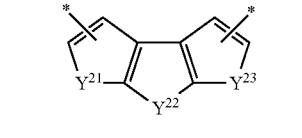

(1D-1g)

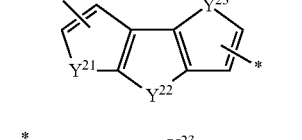

(1D-1h)

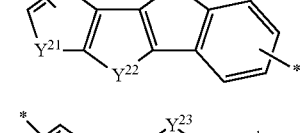

(1D-1i)

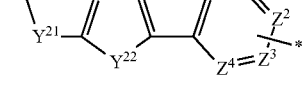

(1D-1j)

wherein, in Chemical Formula 1 D-1,
hydrogen of each aromatic ring is optionally replaced by deuterium, a halogen, a cyano group, a C1 to C10 alkyl group, a C1 to C10 haloalkyl group, a silyl group, a C1 to C10 alkylsilyl group, a C6 to C20 aryl group, or a C3 to C20 heteroaryl group, $Y^{21}$, $Y^{22}$, and $Y^{23}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Z^1$, $Z^2$, $Z^3$, $Z^4$, $Z^5$, and $Z^6$ are each independently N or CR$^x$, wherein R$^x$ is hydrogen, deuterium, a C1 to C6 alkyl group, a C1 to C6 haloalkyl group, a C6 to C12 aryl group, a C3 to C12 heteroaryl group, a halogen, a cyano group, or a combination thereof, wherein at least one of $Z^1$ to $Z^4$ in Chemical Formula 1D-1 b and Chemical Formula 1D-1j is N and $Z^1$ to $Z^6$ in Chemical Formula 1 D-1 d and Chemical Formula 1 D-1 f is N, and

* on a left side of Chemical Formula 1 D-1 is a portion that is bound to $Ar^1$ of Chemical Formula 1, and * on a right side of Chemical Formula 1 D-1 is a portion that is bound to N of —$N(R^3)(R^4)$ of Chemical Formula 1.

15. The infrared absorber of claim 1, wherein in Chemical Formula 1, *—$N(R^1)(R^2)$ and *—$N(R^3)(R^4)$ are each independently represented by Chemical Formula D:

[Chemical Formula D]

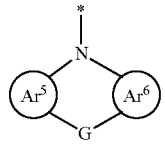

wherein, in Chemical Formula D,
  $Ar^5$ and $Ar^6$ are each independently a substituted or unsubstituted C6 to C30 arene group or a substituted or unsubstituted C3 to C30 heteroarene group,
  G is a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ are each independently hydrogen, deuterium, a halogen, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ each independently exist or are linked to each other to provide a ring, and n of —$(CR^fR^g)_n$— is an integer of 1 or 2, and
  * is a linking point with Chemical Formula 1.

16. The infrared absorber of claim 1, wherein the infrared absorber has a peak absorption wavelength in a wavelength region of about 750 nm to about 3000 nm.

17. An infrared absorbing/blocking film comprising the infrared absorber of claim 1.

18. A photoelectric device, comprising
a first electrode and a second electrode facing each other, and
a photoactive layer between the first electrode and the second electrode,
wherein the photoactive layer comprises an infrared absorber including a compound represented by Chemical Formula 1:

[Chemical Formula 1]

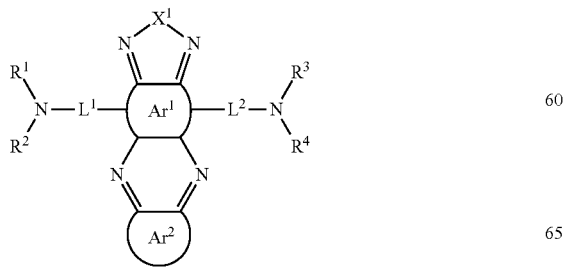

wherein, in Chemical Formula 1,
  $Ar^1$ is a substituted or unsubstituted C6 to C30 aromatic ring, a substituted or unsubstituted C3 to C30 heteroaromatic ring, or a combination thereof,
  $Ar^2$ is a substituted or unsubstituted C6 to C30 aromatic ring, a substituted or unsubstituted C3 to C30 heteroaromatic ring, or a combination thereof,
  $X^1$ is O, S, Se, Te, S(=O), S(=O)$_2$, $NR^a$, $CR^bR^c$, or $SiR^dR^e$, wherein $R^a$, $R^b$, $R^c$, $R^d$, and $R^e$ are each independently hydrogen, deuterium, a C1 to C6 alkyl group, a C1 to C6 haloalkyl group, a C6 to C12 aryl group, a C3 to C12 heteroaryl group, a halogen, a cyano group, or a combination thereof,
  $R^1$, $R^2$, $R^3$, and $R^4$ are each independently hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof,
  $R^1$ and $R^2$ each independently exist or are linked to each other to form a first ring, and $R^3$ and $R^4$ each independently exist or are linked to each other to form a second ring, and
  $L^1$ is represented by Chemical Formula 1A or Chemical Formula 1B, and $L^2$ is represented by Chemical Formula 1C or Chemical Formula 1D:

[Chemical Formula 1A]

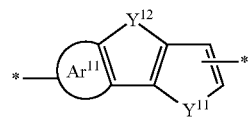

[Chemical Formula 1B]

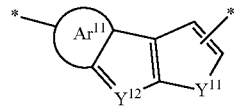

wherein, in Chemical Formula 1A and Chemical Formula 1B,
  $Y^{11}$ and $Y^{12}$ are each independently O, S, Se, Te, S(=O), S(=O)$_2$, $NR^a$, or $SiR^bR^c$, wherein $R^a$, $R^b$, and $R^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof,
  $Ar^{11}$ is a substituted or unsubstituted C6 to C30 aromatic ring, a substituted or unsubstituted C3 to C30 heteroaromatic ring, or a combination thereof, and
  * on a left side of Chemical Formula 1A and Chemical Formula 1B is a portion that is bound to N of —$N(R^1)(R^2)$ of Chemical Formula 1, and * on a right side of Chemical Formula 1A and Chemical Formula 1B is a portion that is bound to $Ar^1$ of Chemical Formula 1,

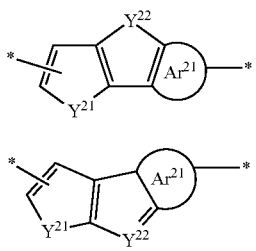

[Chemical Formula 1C]

[Chemical Formula 1D]

wherein, in Chemical Formula 1C and Chemical Formula 1D, $Y^{21}$ and $Y^{22}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, Ar$^{21}$ is a substituted or unsubstituted C6 to C30 aromatic ring, a substituted or unsubstituted C3 to C30 heteroaromatic ring, or a combination thereof, and

* on a left side of Chemical Formula 1C and Chemical Formula 1D is a portion that is bound to Ar$^1$ of Chemical Formula 1, and * on a right side of Chemical Formula 1C and Chemical Formula 1D is a portion that is bound to N of —N(R$^3$)(R$^4$) of Chemical Formula 1.

19. The photoelectric device of claim 18, wherein the photoactive layer further includes fullerene or a fullerene derivative.

20. The photoelectric device of claim 18, wherein the infrared absorber has a peak absorption wavelength in a wavelength region of about 750 nm to about 3000 nm.

21. A photoelectric device, comprising:

a first electrode and a second electrode facing each other;

a photoactive layer between the first electrode and the second electrode; and a charge auxiliary layer between the photoactive layer and the first electrode, or the photoactive layer and the second electrode, wherein at least one of the photoactive layer or the charge auxiliary layer includes the infrared absorber of claim 1.

22. A sensor comprising the photoelectric device of claim 21.

23. An image sensor, comprising:

a semiconductor substrate;

a first photoelectric device on the semiconductor substrate, the first photoelectric device configured to selectively absorb light in a first infrared wavelength region; and an additional sensor configured to selectively absorb light in a separate wavelength region that is different from the first infrared wavelength region, wherein the first photoelectric device includes an infrared absorber that includes a compound represented by Chemical Formula 1:

[Chemical Formula 1]

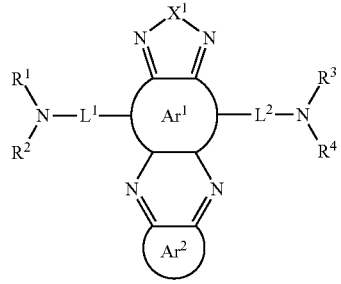

wherein, in Chemical Formula 1,

Ar$^1$ is a substituted or unsubstituted C6 to C30 aromatic ring, a substituted or unsubstituted C3 to C30 heteroaromatic ring, or a combination thereof, Ar$^2$ is a substituted or unsubstituted C6 to C30 aromatic ring, a substituted or unsubstituted C3 to C30 heteroaromatic ring, or a combination thereof, X$^1$ is O, S, Se, Te, S(=O), S(=O)$_2$, NR$^a$, CR$^b$R$^c$, or SiR$^d$R$^e$, wherein R$^a$, R$^b$, R$^c$, R$^d$, and R$^e$ are each independently hydrogen, deuterium, a C1 to C6 alkyl group, a C1 to C6 haloalkyl group, a C6 to C12 aryl group, a C3 to C12 heteroaryl group, a halogen, a cyano group, or a combination thereof, R$^1$, R$^2$, R$^3$, and R$^4$ are each independently hydrogen, deuterium, a substituted or unsubstituted C1 to C30 alkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C3 to C30 heteroaryl group, a substituted or unsubstituted silyl group, a halogen, or a combination thereof, R$^1$ and R$^2$ each independently exist or are linked to each other to form a first ring, and R$^3$ and R$^4$ each independently exist or are linked to each other to form a second ring, and L$^1$ is represented by Chemical Formula 1A or Chemical Formula 1B, and L$^2$ is represented by Chemical Formula 1C or Chemical Formula 1D:

[Chemical Formula 1A]

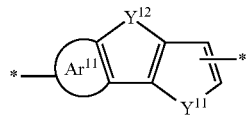

[Chemical Formula 1B]

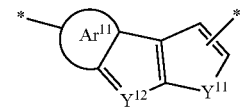

wherein, in Chemical Formula 1A and Chemical Formula 1B, $Y^{11}$ and $Y^{12}$ are each independently O, S, Se, Te, S(=O), S(=O)$_2$, NR$^a$, or SiR$^b$R$^c$, wherein R$^a$, R$^b$, and R$^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Ar^{11}$ is a substituted or unsubstituted C6 to C30 aromatic ring, a substituted or unsubstituted C3 to C30 heteroaromatic ring, or a combination thereof, and

* on a left side of Chemical Formula 1A and Chemical Formula 1B is a portion that is bound to N of —N($R^1$)($R^2$) of Chemical Formula 1, and * on a right side of Chemical Formula 1A and Chemical Formula 1B is a portion that is bound to $Ar^1$ of Chemical Formula 1,

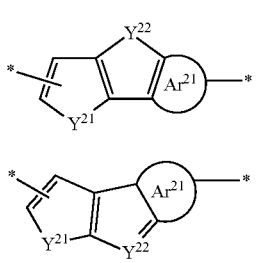

[Chemical Formula 1C]

[Chemical Formula 1D]

wherein, in Chemical Formula 1C and Chemical Formula 1D, $Y^{21}$ and $Y^{22}$ are each independently O, S, Se, Te, S(=O), S(=O)$_2$, $NR^a$, or $SiR^bR^c$, wherein $R^a$, $R^b$, and $R^c$ are each independently hydrogen, deuterium, a C1 to C6 alkyl group, a C1 to C10 haloalkyl group, a silyl group, a C1 to C10 alkylsilyl group, an amine group, a C1 to C10 alkylamine group, a C6 to C12 aryl group, a C3 to C12 heteroaryl group, a halogen, a cyano group, or a combination thereof, $Ar^{21}$ is a substituted or unsubstituted C6 to C30 aromatic ring, a substituted or unsubstituted C3 to C30 heteroaromatic ring, or a combination thereof, and

* on a left side of Chemical Formula 1C and Chemical Formula 1D is a portion that is bound to $Ar^1$ of Chemical Formula 1, and * on a right side of Chemical Formula 1C and Chemical Formula 1D is a portion that is bound to N of —N($R^3$)($R^4$) of Chemical Formula 1.

24. The image sensor of claim 23, wherein the additional sensor is an infrared light sensor at least partially embedded within the semiconductor substrate, and the separate wavelength region is a separate infrared wavelength region that is different from the first infrared wavelength region, and the first photoelectric device and the infrared light sensor overlap in a vertical direction that is perpendicular to an upper surface of the semiconductor substrate.

25. The image sensor of claim 24, wherein the additional sensor includes a plurality of photodiodes at least partially embedded within the semiconductor substrate, the plurality of photodiodes configured to selectively absorb light in separate visible wavelength regions, and the first photoelectric device and the plurality of photodiodes overlap in the vertical direction that is perpendicular to the upper surface of the semiconductor substrate.

26. The image sensor of claim 23, wherein the additional sensor includes at least one additional photoelectric device vertically stacked between the first photoelectric device and the semiconductor substrate, each separate photoelectric device of the at least one additional photoelectric device including a separate photoelectric conversion layer and configured to selectively absorb light in a separate, respective wavelength region that is different from the first infrared wavelength region.

27. The image sensor of claim 23, wherein the first photoelectric device includes a first electrode and a second electrode facing each other; and a photoactive layer between the first electrode and the second electrode, wherein the photoactive layer includes the infrared absorber.

28. The image sensor of claim 23, wherein the first photoelectric device includes a first electrode and a second electrode facing each other;

a photoactive layer between the first electrode and the second electrode; and a charge auxiliary layer between the photoactive layer and the first electrode, or the photoactive layer and the second electrode, wherein the charge auxiliary layer includes the infrared absorber.

29. An electronic device comprising the sensor of claim 22.

30. An electronic device comprising the photoelectric device of claim 18.

* * * * *